US012594063B2

(12) United States Patent
Chen

(10) Patent No.: US 12,594,063 B2
(45) Date of Patent: *Apr. 7, 2026

(54) TISSUE IMAGING IN PRESENCE OF FLUID DURING BIOPSY PROCEDURE

(71) Applicant: Hologic, Inc., Marlborough, MA (US)

(72) Inventor: Biao Chen, Newark, DE (US)

(73) Assignee: Hologic, Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/635,235

(22) Filed: Apr. 15, 2024

(65) Prior Publication Data

US 2024/0315676 A1     Sep. 26, 2024

Related U.S. Application Data

(63) Continuation of application No. 17/417,642, filed as application No. PCT/US2019/067427 on Dec. 19, 2019, now Pat. No. 11,986,170.

(60) Provisional application No. 62/784,935, filed on Dec. 26, 2018.

(51) Int. Cl.
*A61B 10/02*     (2006.01)
*A61B 10/00*     (2006.01)
*G06T 7/10*     (2017.01)

(52) U.S. Cl.
CPC ...... *A61B 10/0266* (2013.01); *A61B 10/0096* (2013.01); *G06T 7/10* (2017.01)

(58) Field of Classification Search
None
See application file for complete search history.

(56) References Cited

U.S. PATENT DOCUMENTS

| | | | |
|---|---|---|---|
| 4,038,988 A | 8/1977 | Perisse | |
| 4,134,012 A | 1/1979 | Smallbone et al. | |
| 4,306,570 A | 12/1981 | Matthews | |
| 4,549,554 A | 10/1985 | Markham | |

(Continued)

FOREIGN PATENT DOCUMENTS

| | | |
|---|---|---|
| CN | 104583754 A | 4/2015 |
| CN | 204489169 U | 7/2015 |

(Continued)

OTHER PUBLICATIONS

European Extended Search Report in Application 22217130.8, mailed Mar. 30, 2023, 6 pages.

(Continued)

*Primary Examiner* — Yi-Shan Yang
(74) *Attorney, Agent, or Firm* — Merchant & Gould P.C.

(57)     ABSTRACT

A hybrid image based on different tissue specimen images is generated to compensate for blood and other fluids that interfere with imaging. Specimen is deposited into tray with fluid. X-ray and camera imaging devices acquire images of specimen and fluid. X-ray and optical images are processed for generation of hybrid image. Transparency modifications allow for multiple and different images to contribute to depiction of specimen edges or boundaries that would otherwise appear less clear in x-ray image due to interfering fluid. Transparency modifications in hybrid image also provide for sufficiently high transparency in certain optical image portions that would otherwise be opaque so that objects of interest depicted in x-ray image but not optical image are visible.

21 Claims, 23 Drawing Sheets

(56) References Cited

U.S. PATENT DOCUMENTS

| | | | |
|---|---|---|---|
| 4,658,834 A | 4/1987 | Blankenship et al. |
| 4,802,195 A | 1/1989 | Wojciechowski |
| 4,803,639 A | 2/1989 | Steele |
| 4,837,795 A | 6/1989 | Garrigus |
| 4,852,560 A | 8/1989 | Hermann, Jr. |
| 5,023,894 A | 6/1991 | Yamashita |
| 5,023,895 A | 6/1991 | McCroskey |
| 5,256,160 A | 10/1993 | Clement |
| 5,427,742 A | 6/1995 | Holland |
| 5,456,689 A | 10/1995 | Kresch et al. |
| 5,491,344 A | 2/1996 | Kenny et al. |
| 5,505,210 A | 4/1996 | Clement |
| 5,526,822 A | 6/1996 | Burbank et al. |
| 5,541,856 A | 7/1996 | Hammermeister |
| 5,575,293 A | 11/1996 | Miller et al. |
| 5,609,827 A | 3/1997 | Russell |
| 5,754,621 A | 5/1998 | Suzuki |
| 5,983,125 A | 11/1999 | Alfano et al. |
| 6,017,316 A | 1/2000 | Ritchart et al. |
| 6,032,673 A | 3/2000 | Savage et al. |
| 6,058,159 A | 5/2000 | Conway |
| 6,163,590 A | 12/2000 | Wilkins |
| 6,207,111 B1 | 3/2001 | Weinberg |
| 6,225,107 B1 | 5/2001 | Nagle |
| 6,234,672 B1 | 5/2001 | Tomasetti et al. |
| 6,322,522 B1 | 11/2001 | Zimmon |
| 6,403,035 B1 | 6/2002 | Caratsch et al. |
| 6,485,436 B1 | 11/2002 | Truckai et al. |
| 6,535,284 B1 | 3/2003 | Hajduk et al. |
| 6,646,721 B2 | 11/2003 | Compter |
| 6,899,850 B2 | 5/2005 | Haywood |
| 7,166,113 B2 | 1/2007 | Arambula |
| 7,175,612 B2 | 2/2007 | Felix et al. |
| 7,397,894 B2 | 7/2008 | Nakai |
| 7,546,925 B1 | 6/2009 | Zuk, Jr. |
| 7,616,801 B2 | 11/2009 | Gkanatsios et al. |
| 7,662,109 B2 | 2/2010 | Hibner |
| 7,692,144 B2 | 4/2010 | Watanabe |
| 7,715,523 B2 | 5/2010 | Lafferty |
| 7,753,857 B2 | 7/2010 | Hibner |
| 7,758,601 B2 | 7/2010 | Heywang-Koebrunner et al. |
| 7,826,588 B2 | 11/2010 | Eliasson |
| 7,854,705 B2 | 12/2010 | Pawluczyk et al. |
| 7,856,081 B2 | 12/2010 | Peschmann |
| 7,858,038 B2 | 12/2010 | Andreyko et al. |
| 7,867,173 B2 | 1/2011 | Hibner et al. |
| 7,869,563 B2 | 1/2011 | DeFreitas et al. |
| 7,881,427 B2 | 2/2011 | Kalender et al. |
| 7,881,428 B2 | 2/2011 | Jing et al. |
| 7,972,062 B2 | 7/2011 | Nicolosi |
| 8,038,347 B2 | 10/2011 | Manak |
| 8,038,627 B2 | 10/2011 | Hibner |
| 8,050,735 B2 | 11/2011 | Feke |
| 8,052,616 B2 | 11/2011 | Andrisek et al. |
| 8,162,140 B2 | 4/2012 | Hansen |
| 8,177,728 B2 | 5/2012 | Hibner et al. |
| 8,213,570 B2 | 7/2012 | Panesar |
| 8,217,357 B2 | 7/2012 | Stein et al. |
| 8,235,913 B2 | 8/2012 | Hibner et al. |
| 8,284,896 B2 | 10/2012 | Singh |
| 8,532,745 B2 | 9/2013 | DeFreitas et al. |
| 8,565,374 B2 | 10/2013 | DeFreitas et al. |
| 8,702,623 B2 | 4/2014 | Parihar |
| 8,741,232 B2 | 6/2014 | Baysal |
| 8,764,679 B2 | 7/2014 | Miller et al. |
| 8,787,522 B2 | 7/2014 | Smith et al. |
| 8,838,207 B2 | 9/2014 | Nakayama et al. |
| 8,873,716 B2 | 10/2014 | Ren et al. |
| 8,911,381 B2 | 12/2014 | Hibner et al. |
| 8,923,603 B2 | 12/2014 | Weston |
| 8,956,306 B2 | 2/2015 | Hibner |
| 8,971,484 B2 | 3/2015 | Beckmann |
| 8,983,030 B2 | 3/2015 | Ookawa |
| 9,020,579 B2 | 4/2015 | Smith et al. |
| 9,066,706 B2 | 6/2015 | DeFreitas et al. |
| 9,068,920 B2 | 6/2015 | Churilla |
| 9,129,715 B2 | 9/2015 | Adler |
| 9,188,696 B2 | 11/2015 | Schafer |
| 9,234,855 B2 | 1/2016 | Watanabe |
| 9,277,895 B2 | 3/2016 | Hara |
| 9,322,790 B2 | 4/2016 | Ookawa |
| 9,326,755 B2 | 5/2016 | Fiebig |
| 9,329,139 B2 | 5/2016 | Itou |
| 9,341,546 B2 | 5/2016 | Stuke |
| 9,347,894 B2 | 5/2016 | Sims |
| 9,492,130 B2 * | 11/2016 | Flagle ................ A61B 6/4405 |
| 9,498,175 B2 | 11/2016 | Stein et al. |
| 9,549,709 B2 | 1/2017 | DeFreitas et al. |
| 9,557,281 B2 | 1/2017 | Badawi et al. |
| 9,642,581 B2 | 5/2017 | Lowe |
| 9,668,711 B2 | 6/2017 | Smith et al. |
| 9,733,167 B2 | 8/2017 | Wismueller |
| 9,750,484 B2 | 9/2017 | Finke et al. |
| 9,861,327 B2 | 1/2018 | Yasuda et al. |
| 9,865,424 B2 | 1/2018 | Ikeda |
| 9,901,320 B2 | 2/2018 | DeFreitas et al. |
| 9,943,850 B2 | 4/2018 | Purdy |
| 9,953,799 B2 | 4/2018 | Hakoda |
| 10,008,298 B2 | 6/2018 | King |
| 10,010,296 B2 | 7/2018 | Basu |
| 10,078,093 B2 | 9/2018 | Flagle |
| 10,098,216 B2 | 10/2018 | Kabumoto |
| 10,105,709 B2 | 10/2018 | Purdy |
| 10,145,806 B2 | 12/2018 | Tanaka |
| 10,190,997 B2 | 1/2019 | Aoki |
| 10,194,875 B2 | 2/2019 | DeFreitas et al. |
| 10,201,331 B2 | 2/2019 | Fleming |
| 10,322,412 B2 | 6/2019 | Purdy |
| 10,393,678 B2 | 8/2019 | Watanabe |
| 10,488,351 B2 | 11/2019 | Butani |
| 10,489,964 B2 | 11/2019 | Wang |
| 10,542,951 B2 | 1/2020 | Klausz et al. |
| 10,561,387 B2 | 2/2020 | Smith et al. |
| 10,631,809 B2 | 4/2020 | Noh |
| 10,705,030 B2 | 7/2020 | Watanabe |
| 10,709,396 B2 | 7/2020 | Lou |
| 10,729,403 B2 | 8/2020 | DeFreitas et al. |
| 10,753,836 B2 | 8/2020 | O'Driscoll |
| 10,792,003 B2 | 10/2020 | Smith et al. |
| 10,809,208 B2 | 10/2020 | Yashima |
| 10,827,989 B2 | 11/2020 | Vancamberg et al. |
| 10,905,385 B2 | 2/2021 | DeFreitas et al. |
| 11,083,426 B2 | 8/2021 | DeFreitas |
| 11,191,502 B2 | 12/2021 | Smith et al. |
| 11,246,551 B2 | 2/2022 | Butani |
| 11,478,206 B2 | 10/2022 | Smith et al. |
| 11,617,548 B2 | 4/2023 | DeFreitas et al. |
| 11,730,434 B2 | 8/2023 | DeFreitas |
| 11,877,877 B2 | 1/2024 | Purdy |
| 11,986,170 B2 | 5/2024 | Chen |
| 12,030,058 B2 | 7/2024 | Purdy |
| 2002/0007188 A1 | 1/2002 | Arambula |
| 2002/0145722 A1 | 10/2002 | Compter |
| 2002/0193656 A1 | 12/2002 | Ravins et al. |
| 2003/0087423 A1 | 5/2003 | Haywood |
| 2003/0216730 A1 | 11/2003 | Barry et al. |
| 2004/0022350 A1 | 2/2004 | Gregerson et al. |
| 2004/0174031 A1 | 9/2004 | Rasmussen |
| 2004/0218716 A1 | 11/2004 | Freifeld |
| 2005/0051723 A1 | 3/2005 | Neagle et al. |
| 2005/0065453 A1 | 3/2005 | Shabaz et al. |
| 2005/0112034 A1 | 5/2005 | McCormick |
| 2005/0124913 A1 | 6/2005 | Damarati |
| 2005/0148842 A1 | 7/2005 | Wang |
| 2006/0074343 A1 | 4/2006 | Hibner |
| 2006/0116603 A1 | 6/2006 | Shibazaki et al. |
| 2006/0173266 A1 | 8/2006 | Pawluczyk et al. |
| 2007/0106176 A1 | 5/2007 | Mark et al. |
| 2007/0116612 A1 | 5/2007 | Williamson |
| 2007/0166834 A1 | 7/2007 | Williamson, IV et al. |
| 2007/0237684 A1 | 10/2007 | Hansen |
| 2007/0239067 A1 | 10/2007 | Hibner et al. |
| 2007/0270714 A1 | 11/2007 | Cushner et al. |
| 2008/0004545 A1 | 1/2008 | Garrison |

(56) References Cited

U.S. PATENT DOCUMENTS

| | | |
|---|---|---|
| 2008/0082021 A1 | 4/2008 | Ichikawa |
| 2008/0132805 A1 | 6/2008 | Heywang-Koebrunner et al. |
| 2008/0137935 A1 | 6/2008 | Spahn |
| 2008/0214955 A1 | 9/2008 | Speeg et al. |
| 2008/0221480 A1 | 9/2008 | Hibner et al. |
| 2008/0228103 A1 | 9/2008 | Ritchie et al. |
| 2008/0249434 A1 | 10/2008 | Hashimshony et al. |
| 2009/0088663 A1 | 4/2009 | Miller et al. |
| 2009/0088666 A1 | 4/2009 | Miller et al. |
| 2009/0131818 A1 | 5/2009 | Speeg et al. |
| 2009/0131820 A1 | 5/2009 | Speeg |
| 2009/0131823 A1 | 5/2009 | Andreyko et al. |
| 2009/0171243 A1 | 7/2009 | Hibner et al. |
| 2009/0171244 A1 | 7/2009 | Ning |
| 2009/0213987 A1 | 8/2009 | Stein |
| 2010/0080346 A1 | 4/2010 | Kalender et al. |
| 2010/0081964 A1 | 4/2010 | Mark |
| 2010/0152611 A1 | 6/2010 | Parihar |
| 2010/0160824 A1 | 6/2010 | Parihar |
| 2010/0160826 A1 | 6/2010 | Parihar |
| 2010/0191145 A1 | 7/2010 | Lafferty |
| 2010/0317997 A1 | 12/2010 | Hibner |
| 2011/0123074 A1 | 5/2011 | Nie |
| 2011/0142201 A1 | 6/2011 | Eberhard et al. |
| 2011/0285837 A1 | 11/2011 | Bello |
| 2012/0014504 A1 | 1/2012 | Jang et al. |
| 2012/0051514 A1 | 3/2012 | Sims et al. |
| 2012/0053484 A1 | 3/2012 | Parks |
| 2012/0065542 A1 | 3/2012 | Hibner et al. |
| 2012/0116246 A1 | 5/2012 | Hibner |
| 2012/0123295 A1 | 5/2012 | Sanbuichi |
| 2012/0245485 A1 | 9/2012 | Hibner |
| 2013/0053724 A1 | 2/2013 | Fiebig |
| 2013/0101089 A1* | 4/2013 | Cho .................... A61B 6/5241 |
| | | 378/62 |
| 2013/0231585 A1 | 9/2013 | Flagle |
| 2014/0039343 A1 | 2/2014 | Mescher |
| 2014/0051986 A1* | 2/2014 | Zhao ................ A61B 1/000094 |
| | | 600/424 |
| 2014/0065656 A1 | 3/2014 | Baysal |
| 2014/0072104 A1 | 3/2014 | Jacobsen et al. |
| 2014/0198893 A1 | 7/2014 | Badawi et al. |
| 2014/0257135 A1 | 9/2014 | DeFreitas |
| 2014/0276209 A1 | 9/2014 | Hibner |
| 2015/0083893 A1 | 3/2015 | Wismueller |
| 2015/0131773 A1 | 5/2015 | Lowe et al. |
| 2015/0209017 A1 | 7/2015 | Fleming |
| 2016/0073988 A1* | 3/2016 | Nagai .................... A61B 6/482 |
| | | 378/62 |
| 2016/0151054 A1 | 6/2016 | An |
| 2016/0211045 A1 | 7/2016 | Jeon et al. |
| 2017/0131311 A1 | 5/2017 | Flagle |
| 2017/0309063 A1 | 10/2017 | Wang |
| 2017/0336706 A1* | 11/2017 | Wang ................... A61B 5/0071 |
| 2018/0168523 A1 | 6/2018 | Vancamberg et al. |
| 2018/0249985 A1 | 9/2018 | DeFreitas et al. |
| 2019/0054217 A1 | 2/2019 | Axon |
| 2019/0072463 A1 | 3/2019 | O'Driscoll |
| 2019/0130563 A1 | 5/2019 | Vecchio et al. |
| 2019/0167869 A1 | 6/2019 | Willard |
| 2019/0195754 A1 | 6/2019 | Keller |
| 2019/0269376 A1* | 9/2019 | Butani .................... A61B 6/025 |
| 2019/0285558 A1 | 9/2019 | DeFreitas |
| 2019/0346471 A1 | 11/2019 | Flagle |
| 2020/0029927 A1 | 1/2020 | Wilson et al. |
| 2020/0061622 A1 | 2/2020 | Purdy |
| 2020/0085393 A1 | 3/2020 | Zhang et al. |
| 2020/0160522 A1* | 5/2020 | Merlo ........................ B01L 9/52 |
| 2020/0187923 A1 | 6/2020 | Safir |
| 2020/0268331 A1 | 8/2020 | Purdy |
| 2020/0352543 A1 | 11/2020 | DeFreitas et al. |
| 2020/0386657 A1 | 12/2020 | O'Driscoll |
| 2022/0015729 A1 | 1/2022 | Purdy et al. |
| 2022/0015731 A1 | 1/2022 | Liu |
| 2022/0039766 A1 | 2/2022 | DeFreitas |
| 2022/0110597 A1 | 4/2022 | Chen |
| 2022/0133252 A1 | 5/2022 | Smith et al. |
| 2022/0296189 A1 | 9/2022 | Purdy |
| 2022/0331808 A1 | 10/2022 | Purdy |
| 2023/0012310 A1 | 1/2023 | Stango |
| 2023/0014922 A1 | 1/2023 | DeFreitas |
| 2023/0121010 A1 | 4/2023 | Smith et al. |
| 2023/0136395 A1 | 5/2023 | Chen |
| 2023/0172572 A1 | 6/2023 | Bumdra |
| 2023/0204473 A1 | 6/2023 | O'Driscoll |
| 2023/0355200 A1 | 11/2023 | Ren |
| 2023/0404499 A1 | 12/2023 | DeFreitas |
| 2024/0016461 A1 | 1/2024 | Wolff |
| 2024/0148348 A1 | 5/2024 | Purdy |
| 2024/0219276 A1 | 7/2024 | DeFreitas |
| 2024/0359187 A1 | 10/2024 | Purdy |
| 2025/0166798 A1* | 5/2025 | Tripathi ................ G06T 7/0014 |

FOREIGN PATENT DOCUMENTS

| | | |
|---|---|---|
| CN | 110023994 A | 7/2019 |
| CN | 110393553 A | 11/2019 |
| DE | 20 2019 106 995 | 1/2020 |
| EP | 2277445 | 1/2011 |
| EP | 2007287 | 6/2016 |
| EP | 3143937 | 3/2017 |
| GB | 2018601 | 10/1979 |
| JP | 2006-346179 | 12/2006 |
| JP | 2014-526937 | 10/2014 |
| JP | 2015-085056 | 5/2015 |
| JP | 2015-520402 | 7/2015 |
| JP | 2016-154878 | 9/2016 |
| JP | 2017099928 | 6/2017 |
| JP | 6320717 B2 | 5/2018 |
| WO | 8101363 | 5/1981 |
| WO | 2007021905 | 2/2007 |
| WO | 2008/025146 | 3/2008 |
| WO | 2009/120206 | 10/2009 |
| WO | 2010/028208 | 3/2010 |
| WO | 2011/140374 | 11/2011 |
| WO | 2012/074885 | 6/2012 |
| WO | 2013/166497 | 11/2013 |
| WO | 2017/060726 | 4/2017 |
| WO | 2018/183086 | 10/2018 |
| WO | 2018/204710 | 11/2018 |
| WO | 2019/051496 | 3/2019 |
| WO | 2019/085342 | 5/2019 |
| WO | 2019/216766 | 11/2019 |
| WO | 2020/106888 | 5/2020 |
| WO | 2021/202455 | 10/2021 |

OTHER PUBLICATIONS

PCT International Search Report and Written Opinion in Application PCT/US2019/067427, mailed May 28, 2020, 8 pages.

PCT Preliminary Report on Patentability in Application PCT/US2019/067427, mailed Jul. 8, 2021, 7 pages.

Watanabe, M. et al., "The quantitative analysis of thin specimens: a review of progress from the Cliff-Lorimer to the new zeta-factor methods", Journal of Microscopy, vol. 221, No. 2, Feb. 1, 2006, p. 91.

Basak Erguvan-Dogan et al., "Specimen Radiography in Confirmation of MRI-Guided Needle Localization and Surgical Excision of Breast Lesions", American Journal of Roentgenology, American Roentgen Ray Society, vol. 187, No. 2: 339-344 (2006).

* cited by examiner

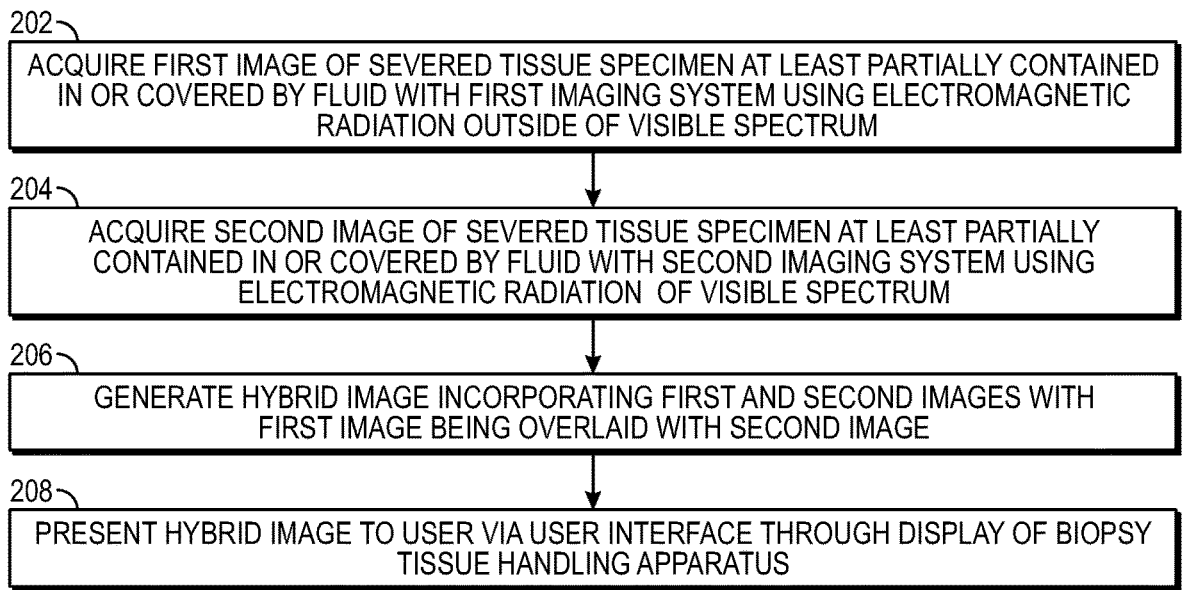

202
ACQUIRE FIRST IMAGE OF SEVERED TISSUE SPECIMEN AT LEAST PARTIALLY CONTAINED IN OR COVERED BY FLUID WITH FIRST IMAGING SYSTEM USING ELECTROMAGNETIC RADIATION OUTSIDE OF VISIBLE SPECTRUM

204
ACQUIRE SECOND IMAGE OF SEVERED TISSUE SPECIMEN AT LEAST PARTIALLY CONTAINED IN OR COVERED BY FLUID WITH SECOND IMAGING SYSTEM USING ELECTROMAGNETIC RADIATION OF VISIBLE SPECTRUM

206
GENERATE HYBRID IMAGE INCORPORATING FIRST AND SECOND IMAGES WITH FIRST IMAGE BEING OVERLAID WITH SECOND IMAGE

208
PRESENT HYBRID IMAGE TO USER VIA USER INTERFACE THROUGH DISPLAY OF BIOPSY TISSUE HANDLING APPARATUS

FIG. 2

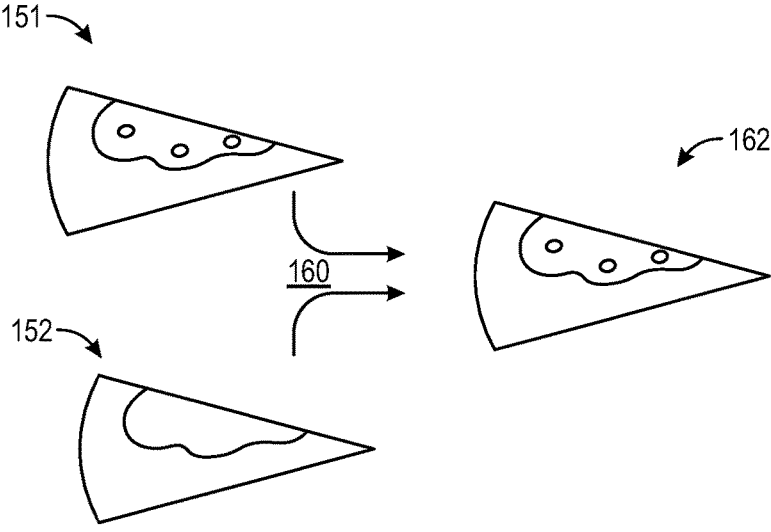

FIG. 3

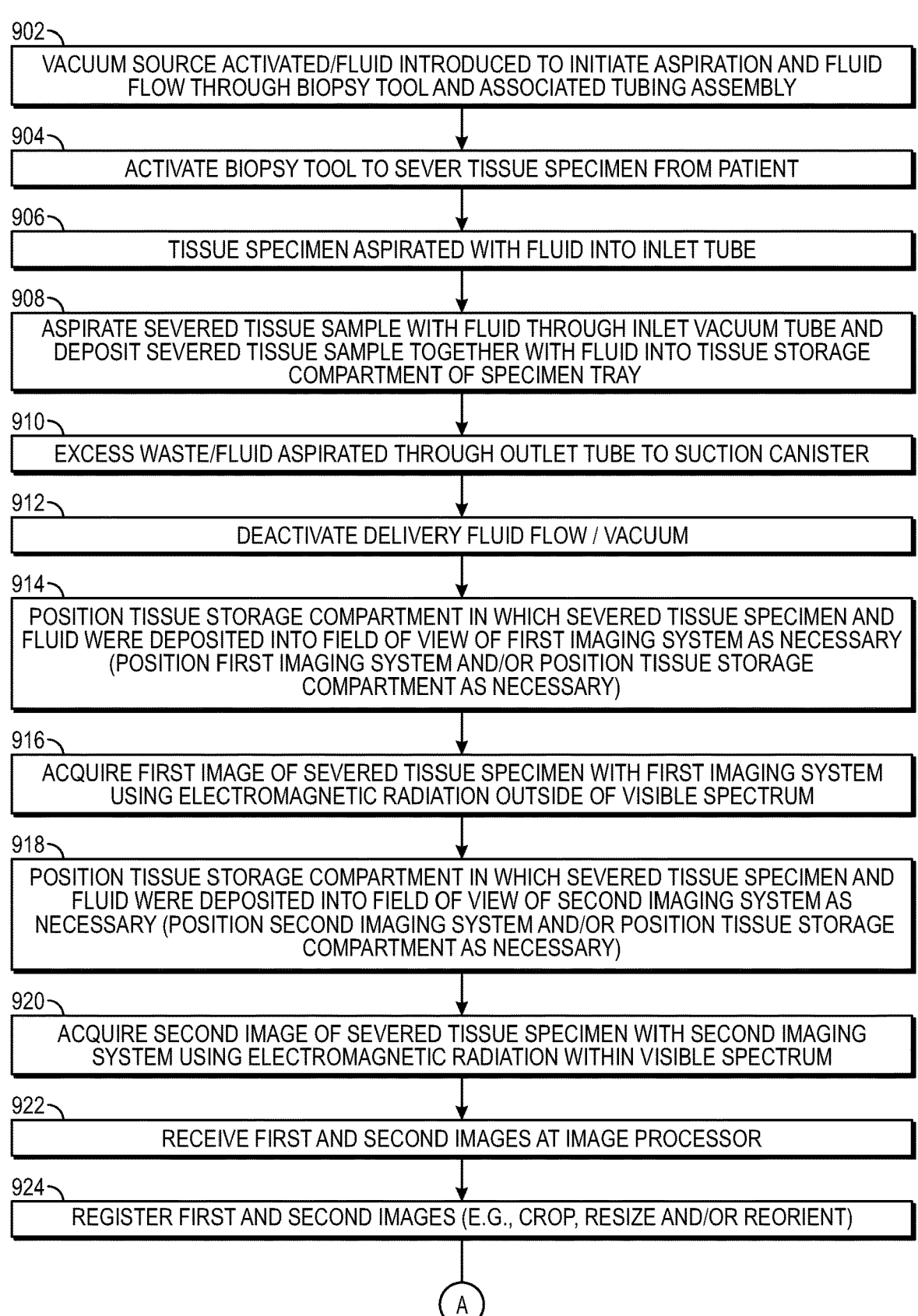

902 — VACUUM SOURCE ACTIVATED/FLUID INTRODUCED TO INITIATE ASPIRATION AND FLUID FLOW THROUGH BIOPSY TOOL AND ASSOCIATED TUBING ASSEMBLY

904 — ACTIVATE BIOPSY TOOL TO SEVER TISSUE SPECIMEN FROM PATIENT

906 — TISSUE SPECIMEN ASPIRATED WITH FLUID INTO INLET TUBE

908 — ASPIRATE SEVERED TISSUE SAMPLE WITH FLUID THROUGH INLET VACUUM TUBE AND DEPOSIT SEVERED TISSUE SAMPLE TOGETHER WITH FLUID INTO TISSUE STORAGE COMPARTMENT OF SPECIMEN TRAY

910 — EXCESS WASTE/FLUID ASPIRATED THROUGH OUTLET TUBE TO SUCTION CANISTER

912 — DEACTIVATE DELIVERY FLUID FLOW / VACUUM

914 — POSITION TISSUE STORAGE COMPARTMENT IN WHICH SEVERED TISSUE SPECIMEN AND FLUID WERE DEPOSITED INTO FIELD OF VIEW OF FIRST IMAGING SYSTEM AS NECESSARY (POSITION FIRST IMAGING SYSTEM AND/OR POSITION TISSUE STORAGE COMPARTMENT AS NECESSARY)

916 — ACQUIRE FIRST IMAGE OF SEVERED TISSUE SPECIMEN WITH FIRST IMAGING SYSTEM USING ELECTROMAGNETIC RADIATION OUTSIDE OF VISIBLE SPECTRUM

918 — POSITION TISSUE STORAGE COMPARTMENT IN WHICH SEVERED TISSUE SPECIMEN AND FLUID WERE DEPOSITED INTO FIELD OF VIEW OF SECOND IMAGING SYSTEM AS NECESSARY (POSITION SECOND IMAGING SYSTEM AND/OR POSITION TISSUE STORAGE COMPARTMENT AS NECESSARY)

920 — ACQUIRE SECOND IMAGE OF SEVERED TISSUE SPECIMEN WITH SECOND IMAGING SYSTEM USING ELECTROMAGNETIC RADIATION WITHIN VISIBLE SPECTRUM

922 — RECEIVE FIRST AND SECOND IMAGES AT IMAGE PROCESSOR

924 — REGISTER FIRST AND SECOND IMAGES (E.G., CROP, RESIZE AND/OR REORIENT)

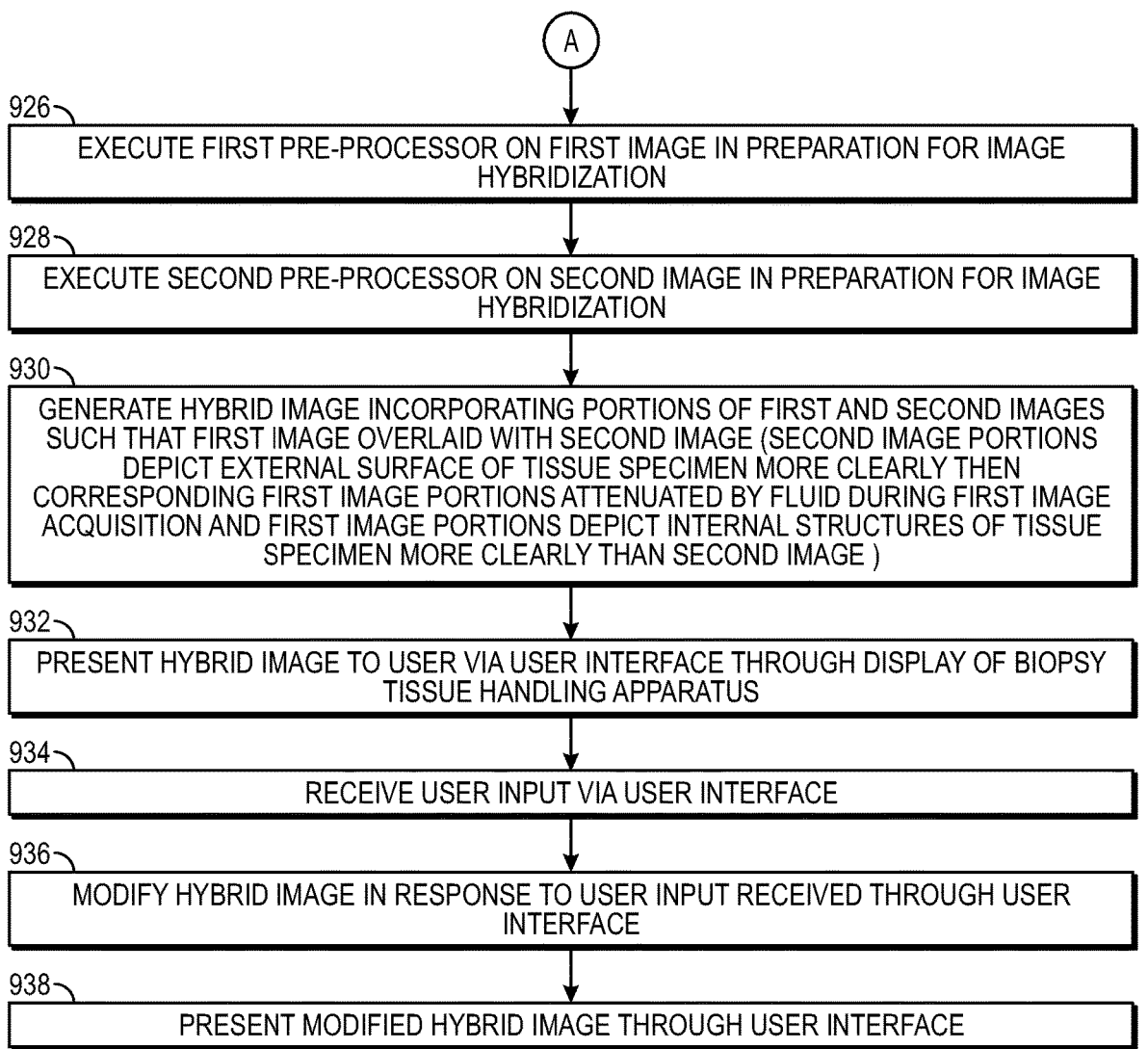

926 — EXECUTE FIRST PRE-PROCESSOR ON FIRST IMAGE IN PREPARATION FOR IMAGE HYBRIDIZATION

928 — EXECUTE SECOND PRE-PROCESSOR ON SECOND IMAGE IN PREPARATION FOR IMAGE HYBRIDIZATION

930 — GENERATE HYBRID IMAGE INCORPORATING PORTIONS OF FIRST AND SECOND IMAGES SUCH THAT FIRST IMAGE OVERLAID WITH SECOND IMAGE (SECOND IMAGE PORTIONS DEPICT EXTERNAL SURFACE OF TISSUE SPECIMEN MORE CLEARLY THEN CORRESPONDING FIRST IMAGE PORTIONS ATTENUATED BY FLUID DURING FIRST IMAGE ACQUISITION AND FIRST IMAGE PORTIONS DEPICT INTERNAL STRUCTURES OF TISSUE SPECIMEN MORE CLEARLY THAN SECOND IMAGE )

932 — PRESENT HYBRID IMAGE TO USER VIA USER INTERFACE THROUGH DISPLAY OF BIOPSY TISSUE HANDLING APPARATUS

934 — RECEIVE USER INPUT VIA USER INTERFACE

936 — MODIFY HYBRID IMAGE IN RESPONSE TO USER INPUT RECEIVED THROUGH USER INTERFACE

938 — PRESENT MODIFIED HYBRID IMAGE THROUGH USER INTERFACE

FIG. 9
(CONTINUED)

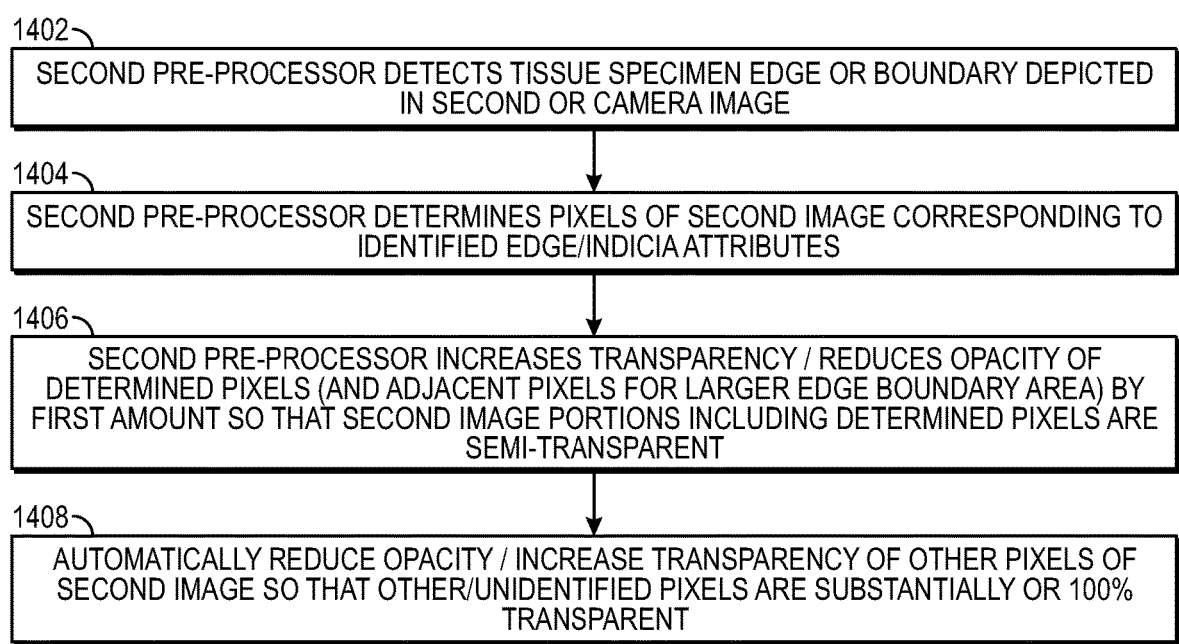

1402
SECOND PRE-PROCESSOR DETECTS TISSUE SPECIMEN EDGE OR BOUNDARY DEPICTED IN SECOND OR CAMERA IMAGE

1404
SECOND PRE-PROCESSOR DETERMINES PIXELS OF SECOND IMAGE CORRESPONDING TO IDENTIFIED EDGE/INDICIA ATTRIBUTES

1406
SECOND PRE-PROCESSOR INCREASES TRANSPARENCY / REDUCES OPACITY OF DETERMINED PIXELS (AND ADJACENT PIXELS FOR LARGER EDGE BOUNDARY AREA) BY FIRST AMOUNT SO THAT SECOND IMAGE PORTIONS INCLUDING DETERMINED PIXELS ARE SEMI-TRANSPARENT

1408
AUTOMATICALLY REDUCE OPACITY / INCREASE TRANSPARENCY OF OTHER PIXELS OF SECOND IMAGE SO THAT OTHER/UNIDENTIFIED PIXELS ARE SUBSTANTIALLY OR 100% TRANSPARENT

FIG. 14

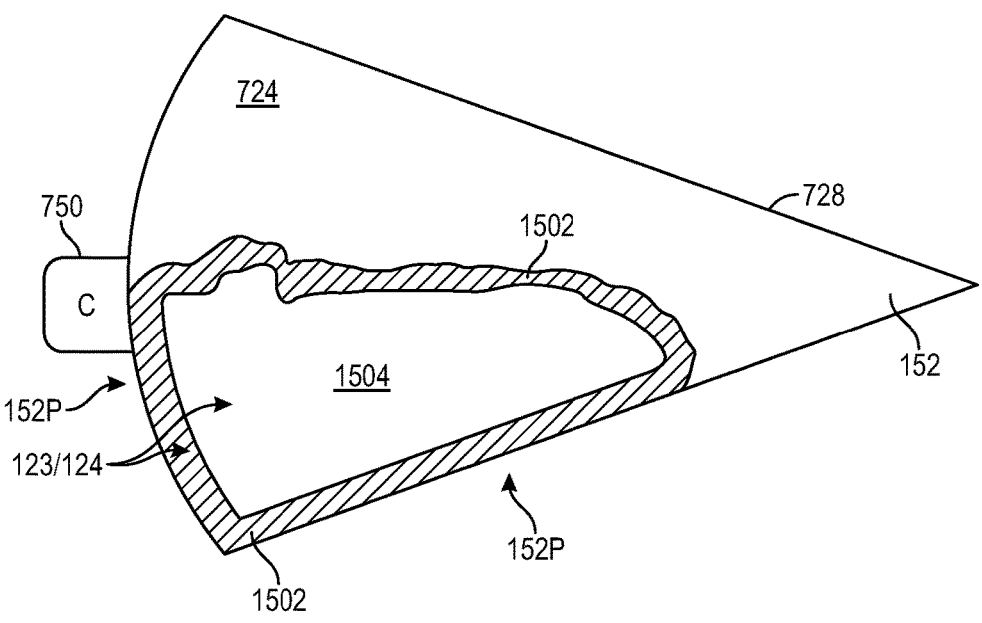

FIG. 15

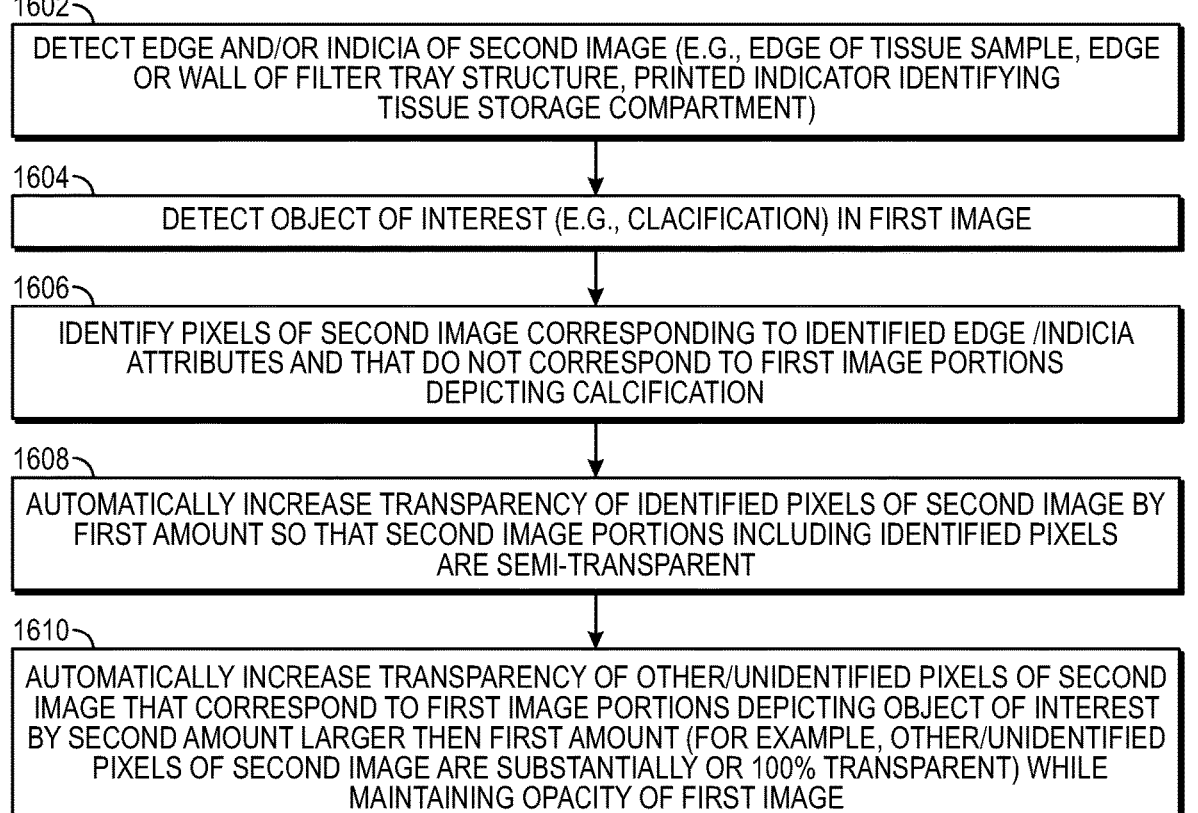

1602 — DETECT EDGE AND/OR INDICIA OF SECOND IMAGE (E.G., EDGE OF TISSUE SAMPLE, EDGE OR WALL OF FILTER TRAY STRUCTURE, PRINTED INDICATOR IDENTIFYING TISSUE STORAGE COMPARTMENT)

1604 — DETECT OBJECT OF INTEREST (E.G., CLACIFICATION) IN FIRST IMAGE

1606 — IDENTIFY PIXELS OF SECOND IMAGE CORRESPONDING TO IDENTIFIED EDGE /INDICIA ATTRIBUTES AND THAT DO NOT CORRESPOND TO FIRST IMAGE PORTIONS DEPICTING CALCIFICATION

1608 — AUTOMATICALLY INCREASE TRANSPARENCY OF IDENTIFIED PIXELS OF SECOND IMAGE BY FIRST AMOUNT SO THAT SECOND IMAGE PORTIONS INCLUDING IDENTIFIED PIXELS ARE SEMI-TRANSPARENT

1610 — AUTOMATICALLY INCREASE TRANSPARENCY OF OTHER/UNIDENTIFIED PIXELS OF SECOND IMAGE THAT CORRESPOND TO FIRST IMAGE PORTIONS DEPICTING OBJECT OF INTEREST BY SECOND AMOUNT LARGER THEN FIRST AMOUNT (FOR EXAMPLE, OTHER/UNIDENTIFIED PIXELS OF SECOND IMAGE ARE SUBSTANTIALLY OR 100% TRANSPARENT) WHILE MAINTAINING OPACITY OF FIRST IMAGE

FIG. 16

TISSUE IMAGING IN PRESENCE OF FLUID DURING BIOPSY PROCEDURE

CROSS-REFERENCE TO RELATED APPLICATIONS

This application is a continuation of U.S. patent application Ser. No. 17/417,642, filed Jun. 23, 2021, now U.S. Pat. No. 11,986,170, which is a National Stage Application of PCT/US2019/067427, filed Dec. 19, 2019, which claims the benefit of U.S. Provisional Patent Application No. 62/784,935, filed Dec. 26, 2018, the entire disclosures of which are incorporated herein by reference in their entireties. To the extent appropriate, a claim of priority is made to each of the above-disclosed applications.

FIELD

The disclosed inventions generally relate to biopsy tissue specimen imaging, and more particularly, to systems and methods for imaging biopsy tissue specimens in fluid in real time during a biopsy procedure.

BACKGROUND

Biopsies are well-known medical procedures involving the removal of tissue from a living body and examining the tissue for diagnostic study, such as determining the presence, cause or extent of a disease. For example, a biopsy of human breast tissue may be performed for diagnosing breast cancer or other diseases. The current standard of care is a percutaneous biopsy, which is performed by inserting a biopsy device having a needle and a cutting device through a small incision and advancing the needle and cutting device to the site of the tissue of interest. The cutting device then cuts a sample of tissue, captures the tissue specimen and removes the tissue specimen through the small incision. Percutaneous biopsy devices have used various means to remove the tissue specimen, such as simply removing the device out through the incision with the captured tissue specimen, or transporting the tissue specimen out through the device where it can be removed or drawn through a tube to a container. One advantage of removing the tissue specimen from the biopsy device is that multiple samples may be taken without having to remove the biopsy device from the patient.

The tissue specimen is typically imaged for verification using X-ray imaging systems. For instance, the tissue specimen may be placed into an X-ray specimen tray or container and then placed into a specimen imaging device for taking an image of the tissue. Automated biopsy and imaging systems for performing a biopsy and imaging a tissue specimen have also been disclosed. One example of a tissue biopsy and handling apparatus is described in U.S. Pat. No. 9,492,130, entitled SYSTEM FOR IMPROVED TISSUE-HANDLING AND IN LINE ANALYSIS OF THE TISSUE, assigned to Hologic, Inc., Marlborough, Massachusetts, the contents of which are incorporated herein by reference as though set forth in full. For example, U.S. Pat. No. 9,492,130 discloses an integrated biopsy analysis system having a biopsy excision tool, a tissue specimen transport mechanism for automatically transporting an excised tissue specimen from the biopsy excision tool to an analysis/imaging unit, and an analysis/imaging system for automatically analyzing tissue specimens such as imaging using an X-ray imaging device. The disclosed system excises tissue specimens and transfers and places the excised tissue specimens into a specimen holder having a plurality of tissue accepting slots for placing a plurality of different tissue specimens. The imaging unit is configured to acquire images of the tissue specimens in the tissue holder, such as by acquiring individual images of each tissue specimen in its respective tissue accepting slot.

SUMMARY

The biopsy and imaging systems described above have some drawbacks. In one example, one or more fluids utilized during or resulting from the biopsy procedure often remains in the imaging field or area imaged by an imaging device and interferes with specimen imaging. For example, one or more of blood, saline and surgical solutions such as anesthetics and other bio-fluids may be deposited into a tissue storage compartment and into the imaging field. These fluids interfere with tissue specimen imaging and reduce the quality of the image. For example, when acquiring an image using an X-ray imaging device, fluids may partially or completely cover or obscure a tissue specimen and/or adhere to the top of or partially or completely cover a tissue specimen. Interfering fluids may have attenuation attributes that are similar to tissue specimens being imaged and obscure specimen edges and boundaries. Thus, an imaged tissue specimen may appear similar to cancerous tissue or tissue having characteristics indicative of cancer, such as a mass, tumor or calcification. Interfering fluid may also appear as a shadow that blocks image portions of interest.

For example, a delivery fluid such as saline may be utilized to transport a tissue specimen through a vacuum tube and blood may be released during the biopsy tissue. Blood and saline may interfere with x-ray imaging and complicate radiologist review and analysis. For example, images generated by an x-ray imaging device may be compromised by fluid obscuring tissue specimen edges or boundaries and this reduced image contrast and sharpness relative to other image elements can reduce the accuracy of identifying and differentiating calcifications, masses, cancerous tissue, etc. These difficulties and shortcomings are compounded as more fluids are present in a tissue specimen compartment and imaging field. It is not uncommon for blood to completely cover a tissue specimen.

Thus, while an x-ray image acquired by known tissue biopsy and handling apparatus may depict certain internal objects of interest or calcifications, parts of the resulting image, external tissue structures and edges or boundaries of the tissue specimen may not be clearly depicted as a result of attenuating or interfering fluids. This can complicate identifying where in the tissue specimen a lesion or calcification or other object of interest such as an implant is located due to attenuated or obscured specimen boundaries. In addition to impairing image quality and the quality of radiologist diagnosis, interfering fluids in the imaging field may also disrupt the review workflow as a result of having to spend extra time on lower quality images that are not be ready for immediate or real time assessment with the result that additional samples may need to be taken and/or additional images may need to be acquired. These complications and inefficiencies may also reduce patient comfort as a result of additional procedures, imaging and time that a patient must remain under compression during the biopsy procedure.

Embodiments of tissue biopsy and handling systems and methods described herein provide for improved in-line tissue specimen imaging in the presence of fluids such as one or more of blood, saline and surgical solutions such as anesthetics and other bio-fluids.

Embodiments of disclosed inventions also provide for improved in-line tissue specimen imaging in the presence of attenuating substances in the field of view of an imaging device during tissue specimen image acquisition.

Embodiments of disclosed inventions also provide for improved tissue specimen image generation and interactive user interfaces of tissue biopsy and handling systems.

Embodiments of disclosed inventions are structured to sever a tissue specimen from a biopsy site of a patient and transport the tissue specimen from the biopsy site with one or more fluids to a tissue storage compartment of the tissue biopsy and handling system. Embodiments perform in-line and real time tissue specimen imaging and examination during the procedure. Various fluids including delivery fluids are present during the process of excising and transporting or aspirating a tissue specimen from the biopsy site to the tissue biopsy and handling system. For example, bodily fluids such as blood resulting from the procedure and a surgical solution such as saline may be present at the location of the biopsy or flow through the tissue biopsy and handling system when severing the tissue specimen and/or drawing the tissue specimen from the tissue biopsy and handling system. Tissue specimens are transported from the biopsy site to the tissue biopsy and handling system through a fluid pathway (e.g., tubing, flow passages, etc.) by vacuum or other mechanical devices and deposited into a specimen tray.

Embodiments of disclosed inventions provide biopsy tissue handling systems and image processing methods utilized thereby for reducing the negative impact that attenuating fluids deposited into a tissue storage compartment and the imaging field have on resulting specimen images. Embodiments not only provide for higher quality specimen images acquired in the presence of fluids, but do so in in-line or in real time during a biopsy procedure while a patient is positioned on a stereotactic biopsy table or breast imaging devices with biopsy procedure capability and provide for more efficient and productive radiologist review.

Embodiments of disclosed inventions utilize multiple imaging modalities and image processing for respective modalities to reduce the impact of interfering or attenuating fluids during specimen imaging. Embodiments of disclosed inventions may also utilize a combination of hybrid image processing and particular specimen tray configurations designed to remove interfering fluid from an imaging field or prevent interfering fluid from entering the imaging field thereby reducing or eliminating the negative impact of fluids on specimen imaging and specimen image analysis in real time during a procedure and while a patient is still positioned on a biopsy table.

Thus, in contrast to merely taking an x-ray and optical images of a tissue specimen and switching between the two images, embodiments solve structural and image processing problems and limitations of tissue biopsy and handling systems and, specifically, improve imaging of specimens in the presence of one or more fluids in real time during a biopsy procedure and processing of specimen images in real time during a biopsy procedure.

According to one embodiment of disclosed inventions, a computer-implemented method executed by a biopsy tissue and handling system includes receiving a severed tissue specimen through a vacuum tube or other mechanical delivery mechanism and into a storage compartment of a specimen tray of a tissue holder assembly of the system. For this purpose, one or more fluids, such as blood, saline or a combination thereof, carries the severed tissue specimen through a lumen defined by the vacuum tube, and the tissue specimen and fluid are deposited together into a tissue storage compartment of a specimen tray. The fluid at least partially covers or contains the severed tissue specimen. Different imaging systems of the tissue biopsy and handling system acquire respective images and/or videos of the severed tissue specimen and fluid in the tissue storage compartment. One imaging system, such as an x-ray imaging system, utilizes electromagnetic radiation outside of a visible spectrum, whereas another imaging system, such as an optical camera imaging system, utilizes electromagnetic radiation that is within the visible spectrum. An image processor of the biopsy tissue handling apparatus receives data of the x-ray and optical images or video frames and generates hybrid image incorporating portions of the x-ray and optical images. Portions of the optical image included in the hybrid image depict an external surface of the severed tissue specimen, such as an edge or periphery of the depicted tissue specimen, more clearly than corresponding x-ray image portions due to the edge or periphery being attenuated or washed out by interfering fluid during x-ray image acquisition. The hybrid image may be constructed by the x-ray image being overlaid with the optical image. As acquired, the optical image is opaque or not transparent. The image processor selectively reduces the optical image transparency. In one embodiment, different portions of the optical image have different semi-transparent transparencies so that certain optical image portions have a first or lower transparency for the edge or periphery so that the edge or periphery is emphasized or more clearly depicted, and another or second optical image portion has higher transparency for the middle or interior portion so that the x-ray image is more clearly viewable through the higher transparency optical image portion compared to the lower transparency optical image portion. Thus, embodiments mitigate or compensate for attenuation of the tissue specimen edge or periphery by interfering fluid that occurred during x-ray image acquisition to provide a more comprehensive and accurate hybrid image with improved edge or periphery definition and improved identification of objects of interest in the tissue specimen with reference to an edge or periphery.

According to another embodiment, a tissue biopsy and handling system comprises a tissue holder assembly, a first imaging system such as an x-ray imaging system, a second imaging system such as an optical camera imaging system, an image processor in communication with the imaging systems, and a display in communication with the image processor. The tissue holder assembly includes a tissue or specimen tray that defines tissue storage compartments and a vacuum tube defining a lumen. The tissue holder and the vacuum tube are arranged and configured to aspirate a severed tissue specimen carried by fluid into the tissue storage compartment with the result that severed tissue specimens are at least partially contained in or covered by fluid in respective tissue storage compartments. The x-ray imaging system is configured to acquire a first, x-ray image or video of a severed tissue specimen and fluid in a tissue storage compartment, and the optical camera imaging system is configured to acquire a second, optical or video image of the severed tissue specimen and fluid in the tissue storage compartment. The image processor is configured or programmed to receive the x-ray image and the optical image and to generate a hybrid image incorporating the x-ray image and the optical image or selected portions thereof. Optical image portions depict an external surface or edge of the severed tissue specimen more clearly than corresponding x-ray image portions attenuated by fluid during acquisition of the x-ray image, and a middle or interior portion of the optical image may have higher transparency so that the x-ray image is more clearly viewable through the higher transparency optical image portion. Thus, embodiments mitigate or compensate for attenuation of the tissue specimen edge or periphery by interfering fluid that occurred during x-ray image acquisition to provide a more comprehensive and accurate hybrid image with improved edge or periphery definition and improved identification of objects of interest in the tissue specimen with reference to an edge or periphery. The hybrid image is presented through an interactive interface through a display in communication with the image processor. Embodiments may involve a static or single hybrid image and/or a live, dynamic or real time hybrid image.

According to one embodiment, the hybrid image is generated by the x-ray image being overlaid with the optical image and the optical image transparency being adjusted so that the x-ray image is at least partially visible through the optical image. Transparency adjustments may be executed to be the same across the optical image. In another embodiment, transparency of selected or determined optical image portions are adjusted to a first transparency, whereas transparency of other selected or determined optical image portions are adjusted to a different, second transparency to provide variable optical image transparency across the optical image. Variable transparency may involve two, three, four and other transparency levels. According to another embodiment, the image processor selects or extracts only certain portions of the optical image, and these selected or extracted portions are adjusted for emphasis as necessary by transparency reduction to be semi-transparent or by the addition of an extraneous graphical data, a marker, indicator or identifier, e.g., along the edge or periphery. The extracted and processed optical image portions are then applied over the x-ray image to form a hybrid image. In this embodiment, only a portion of the optical image is applied over the x-ray image rather than an entire optical image being applied over the x-ray image. Thus, overlaid information used to generate a hybrid image may be in the form of an optical image, selected or extracted portions thereof or generated or generated or graphics by processing thereof, which may involve emphasizing extracted portions and/or by executing graphics processing to emphasize extracted portions or add extraneous indicia for further emphasis.

In one embodiment, the image processor detects an edge or periphery of the severed tissue specimen depicted in the optical image and generates the hybrid image based at least in part upon the x-ray image, the optical image (or extracted and/or processed portions thereof), and the detected edge or periphery of the severed tissue specimen depicted in the optical image (or extracted and/or processed portions thereof). The optical image or portions thereof compensate for attenuation of the edge or periphery depicted in the x-ray image resulting from fluid attenuation during x-ray image acquisition. For example, a portion of the optical image corresponding to an edge or periphery of the depicted tissue specimen may have its transparency adjusted from digital image transparency or 0% transparency to a semi-transparency level that allows for a clearer depiction of the edge or periphery in the optical image to compensate for attenuated edge or periphery portions of the x-ray image while other portions of the optical image are adjusted to have a higher transparency level (e.g., substantially or entirely transparent) so that internal tissue portions and/or calcifications depicted in the x-ray image are visible through or not obscured by the overlaid optical image. As another example, portions of the edge or periphery of the tissue specimen depicted in the optical image are extracted and processed to graphically emphasize the extracted portions, which are then applied over the x-ray image. This may result in a "periphery" or "ring" that is extracted from the optical image and applied over the x-ray image and has partial transparency to compensate for attenuation of the periphery or ring in the underlying x-ray image. With this extracted periphery or ring, no interior or middle portion of the optical image extending across the periphery or ring covers other portions of the x-ray image such that internal portions of the tissue specimen and/or calcifications depicted in the x-ray image are not obscured by the optical image and are clearly visible through the transparent "hole" defined by the extracted ring portion of the optical image.

Thus, with embodiments, a tissue specimen can be seamlessly extracted from a biopsy site, deposited into a specimen tray, imaged and processed to generate a hybrid image with different transparency attributes to compensate for fluid interference or attenuation, particularly for edge or periphery attenuation, and the generated hybrid image can be displayed to a radiologist for real time image review and analysis, and the radiologist or surgeon can quickly determine if additional biopsies and/or images should be acquired, e.g., while a patient is still positioned on a stereotactic table and before the biopsy device has been removed from the patient.

In a single or multiple embodiments, the first or x-ray image is a type of greyscale image, and the second or optical image is a digital color image generated by an optical camera system. Portions of a hybrid image generated according to embodiments depict an external surface (e.g., edge or periphery, and surface contour) of the severed tissue specimen more clearly than corresponding x-ray portions of the hybrid image attenuated, obscured or washed out by one or more fluids that were deposited with the tissue specimen into the tissue storage compartment. The x-ray image may depict both external and internal portions of the severed breast tissue being analyzed and may depict both tissue and calcifications. For example, the x-ray may depict a calcification or lesion within the severed tissue that is not depicted by a digital image generated by a camera system, which is only capable of imaging external surfaces of the severed tissue, and with embodiments, the hybrid image comprises portions of the optical image emphasizing a tissue specimen edge or periphery whereas other optical image portions, such as portions extending between periphery portions, are substantially or completely transparent so as to not obscure the calcification or lesion depicted in the underlying x-ray image.

In a single or multiple embodiments, the tissue or specimen tray in which a severed tissue specimen is deposited is rotatable within the tissue holder assembly, and the specimen tray can be rotated or shifted to positions for loading a severed tissue specimen and to positions for acquiring tissue specimen images by different imaging devices. Imaging devices may be triggered to acquire respective images while the specimen tray is at the same location, or respective images may be acquired at different rotatable positions.

In a single or multiple embodiments, triggering of imaging systems is tied to operation of a mechanical fluid removal structure utilized in conjunction with image processing embodiments. For example, a specimen tray may include a fluid removal structure and x-ray and optical images are acquired by respective x-ray and optical camera imaging devices after a portion of the fluid has been evacuated from the tissue storage compartment by the fluid removal structure. One example of a fluid removal structure is a filter disposed on a base or floor of a tissue storage compartment that allows at least a portion of the fluid that was deposited into the tissue storage compartment to pass from a bottom of the tissue storage compartment through the filter material and to a fluid reservoir positioned below the specimen tray. A fluid removal structure may also be located at a side wall of the tissue storage compartment.

In a single or multiple embodiments, the image processor is located at a remote location relative to the x-ray and optical camera imaging devices, the tissue holder assembly and the display of the tissue biopsy tissue handling system. In these embodiments, the image processor receives the x-ray and optical images at the remote location through a communication network, and a hybrid image is generated by an image processor at the remote location, which may involve execution of machine intelligence on the x-ray and optical images for edge detection. The hybrid image with edge or periphery emphasis generated at a remote location is then transmitted back through the communication network to the tissue biopsy and handling system and presented to the user through the display, which may be in real time during a procedure.

In a single or multiple embodiments, the hybrid image is generated by the x-ray image being overlaid with the second image or selected or extracted portions of the optical image. For this purpose, the optical image or selected or extracted portions thereof is semi-transparent and modified to be semi-transparent so that underlying portions of the x-ray image are visible through the semi-transparent optical image portions while the optical image or selected or extracted portions thereof are also visible. The opacity or transparency of an optical image can be adjusted to be sufficiently transparent and semi-transparent so that an underlying x-ray image is also visible. For example, in embodiments involving application of an optical image over the x-ray image, embodiments may utilize adjustments of a filter or a layer of a digital image acquired by the optical camera system in a similar manner as known image editing programs such as PHOTOSHOP image editing program available from Adobe Inc., San Jose, California. PHOTOSHOP is a registered trademark of Adobe Inc. In other embodiments in which only selected or extracted portions of the optical image used, e.g., edge or periphery portions of a depicted tissue specimen, only the selected or extracted optical image portions are then applied over the x-ray image. For example, a "ring" of selected or extracted optical image portions depicting the tissue specimen periphery may be extracted and applied over the x-ray image. The ring of selected or extracted optical image portions compensate for attenuated portions in the x-ray image and processed for further emphasis if necessary, while not obscuring calcifications or other objects of interest depicted in the x-ray image.

The x-ray and optical images may be processed using one or more noise and/or brightness filters in preparation for or to facilitate generation of a hybrid image based on the x-ray image being overlaid with the optical image or extracted portions thereof. For example, the brightness of the x-ray image may be reduced using a filter so that other portions of the optical image can be accentuated or emphasized while also reducing visual distraction from overly bright areas beyond the tissue specimen such as walls of the specimen tray and exposed surfaces of magnetic components utilized to rotate the specimen tray to different positions. This image processing can also reduce imaged tissue portions that may be ambiguous or erroneously interpreted as a calcification. For example, a first brightness filter may be applied to the x-ray image to identify portions of the x-ray image having a brightness level greater than a pre-determined maximum brightness threshold, and these identified portions are masked or have their brightness reduced. A second brightness filter may also be applied to the x-ray image, and in these embodiments, the second brightness filter identifies portions of the x-ray image having a brightness level less than a second pre-determined minimum brightness threshold (e.g., a darker tray bottom on which a tissue specimen is deposited or filter material thereof), and these x-ray image portions can be masked or their brightness is increased.

In a single or multiple embodiments, tissue specimen edge or periphery based processing of the optical image before generation of the hybrid image involves a pre-determined minimum contrast difference between a portion of the severed tissue specimen and a portion of the specimen tray of the second image. Tissue specimen edge detection may also performed with reference to a structure such as one or more of an outer wall of the specimen tray, an inner or dividing wall that is shared by multiple compartments and engraved or printed indicators for respective tissue storage compartments.

In a single or multiple embodiments, the optical image processing involves reducing an opacity or increasing transparency of the optical image from a first or digital image opacity (100% opaque; 0% transparency) to a second or reduced opacity or increased transparency. In this manner, the second or increased transparency of the optical image results in the optical image (or selected or extracted portions thereof) being semi-transparent such that the optical image (or selected or extracted portions thereof) is visible to the user and corresponding underlying portions of the x-ray image are also visible to the user through the semi-transparent optical image or portions thereof. The transparency of the entire optical image may be increased so that the entire optical image is semi-transparent and visible to the user and the entire underlying x-ray image is visible to the user through the semi-transparent optical image, or extracted portions of an edge or ring may be made semi-transparent. Thus, semi-transparency may extend across the entire optical image or only extracted optical image portions are semi-transparent. In one embodiment, differential or variable transparency adjustments are implemented so that the transparency of optical image portions depicting a periphery or edge of a tissue specimen is increased to be semi-transparent, whereas the transparency of other optical image portions (e.g., middle or interior portions extending across a calcification that is visible in the x-ray image), is further increased to be more transparent than periphery or edge portions of the optical image or completely transparent. Thus, these substantially or completely transparent optical image portions do not obscure corresponding portions of the x-ray image that depict a calcification or other object of interest. In this manner, selective and differential transparency adjustments across the second image allow for calcifications or other objects of interest in the middle or interior portion of the x-ray to be clearly shown without any overlaid optical image, while portions of the optical image that more clearly depict clearly depict an edge of the tissue specimen are semi-transparent and aid in identification of a tissue specimen edge depicted in the x-ray image that was attenuated, blurred or obscured due to interfering fluid during x-ray image acquisition. Semi-transparent portions of the optical image better depict a tissue specimen edge than the underlying x-ray image, to which transparency increases need not be applied, while the x-ray image depicts interior calcifications and objects of interest better than the optical image, thereby providing more accurate and comprehensive image.

In one or more embodiments, image positioning and/or optical image opacity or transparency adjustments can be made in response to user or radiologist input via a computer generated user interface presented through the display of the tissue biopsy and handling system receiving user input through the user interface. For example, an initial hybrid image of an x-ray image overlaid by the optical image or extracted portions thereof can be displayed, and the hybrid image is modified from a hybrid or overlap display mode to an individual or separated display mode in which the x-ray and optical images are separately viewable and the x-ray image is no longer overlaid with the optical image. The user interface may provide a button or element to allow for toggling between these different image display modes. User interface controls may also allow for customized opacity or transparency adjustments in either mode such that in hybrid mode, the optical image as presented on the display may be controllably varied, or varied automatically as a time lapse from opaque to transparent. In furtherance of this controllability, selected sections of the optical image to be subjected to opacity or transparency adjustments can be selected, highlighted or cropped. For example, the user may drag a mouse over portions of the optical image to select or identify an edge or periphery of the optical image, in either hybrid or independent mode, to indicate which portion of the optical image should be processed for opacity reduction for compensation of the edge or periphery depicted by the underlying x-ray image that was attenuated or obscured by interfering fluid. These personalized user interface adjustments may be based on sizing of a square or box or by use of a freehand drawing tool that allows a user of the biopsy tissue handling apparatus draw, e.g., by a mouse of the biopsy tissue handling apparatus or by use of a touch screen, boundaries of a peripheral or outer portion of the optical image to be adjusted to be semi-transparent, and to define other optical image portions to be adjusted to a different transparency level. Drawing tools such as those available from Zillow Group, which allows a user to draw a boundary or circle defining a neighborhood of interest, may be utilized for these purposes.

In a single or multiple embodiments, the optical image, e.g., in the form of a color optical image, depicts a single severed tissue specimen in a single storage compartment, and in other optical images, severed tissue specimens deposited in respective storage compartments are imaged. For example, an x-ray image of a single tissue specimen may be acquired by an x-ray imaging device, whereas the optical image, e.g., due to the field of view of the lens of the optical camera imaging system, may depict respective tissue specimens in respective storage compartments. Additional image processing may include cropping one tissue specimen out from the optical image and rotating or reorienting and adjusting zoom as necessary such that the tissue specimen and specimen tray structure depicted in the x-ray image corresponds to or is registered or aligned with the tissue specimen and specimen tray structure depicted in the optical image. Structural components of the tissue biopsy and handling apparatus may also be used for registration and/or tissue specimen edge detection. For example, one or more of an outer or dividing wall of a specimen tray, a rotational center or spindle of the specimen tray and a label, marker or identifier associated with a tissue compartment, may be utilized for registration since these structural elements are static and depicted in both of the x-ray and optical images.

These imaging processing adjustments may also be performed if the specimen tray is at a first position for acquisition of the x-ray image and then rotated to a second, different position to acquire the optical image. For example, depending on the configuration and arrangement of the imaging devices, an x-ray imaging device may be at a first position to acquire the x-ray image, and then the filter tray is rotated 180 degrees to position the tissue specimen in the field of view of the second imaging device. In other embodiments, the x-ray and optical camera imaging devices are connected or aligned such that it is not necessary to rotate the filter tray and the x-ray and optical images can be acquired by respective first and second imaging devices at the same time or without specimen tray rotation.

Yet other embodiments are directed to how a computer generated user interface is structured to allow for specified user interactions and resulting image modifications and image display modes.

BRIEF DESCRIPTION OF THE DRAWINGS

The foregoing and other aspects of embodiments of the herein disclosed inventions are described in further detail with reference to the accompanying drawings, wherein like reference numerals refer to like elements and the description for like elements shall be applicable for all described embodiments wherever relevant:

FIG. 2 is a flow chart of a method for generating a hybrid image of a tissue specimen according to one embodiment;

FIG. 3 generally depicts how a hybrid image is generated based on images acquired by different imaging devices and transparency adjustments according to one embodiment;

FIGS. 4A-B depict an embodiment of a tissue biopsy and handling system for performing breast biopsy procedures and real time imaging of breast tissue specimens during a biopsy procedure, wherein FIG. 4A illustrates an imaging cabinet in an open position and FIG. 4B illustrates an imaging cabinet in a closed position;

FIG. 9 is a flow diagram provided to illustrate exemplary steps in a process for imaging tissue specimens in the presence of fluids in real time during a biopsy procedure;

FIG. 14 is a flow diagram illustrating exemplary steps of image processing for generation of a hybrid image according to embodiments;

FIG. 15 depicts a tissue specimen and fluid deposited in a tissue storage compartment and how transparency adjustments to an image used to generate a hybrid image can be implemented according to embodiments;

FIG. 16 is a flow diagram illustrating a process to detect an edge or periphery of a tissue specimen in an optical image and resulting transparency modifications to be used in generation of a hybrid image according to embodiments.

DETAILED DESCRIPTION

Figure 1:
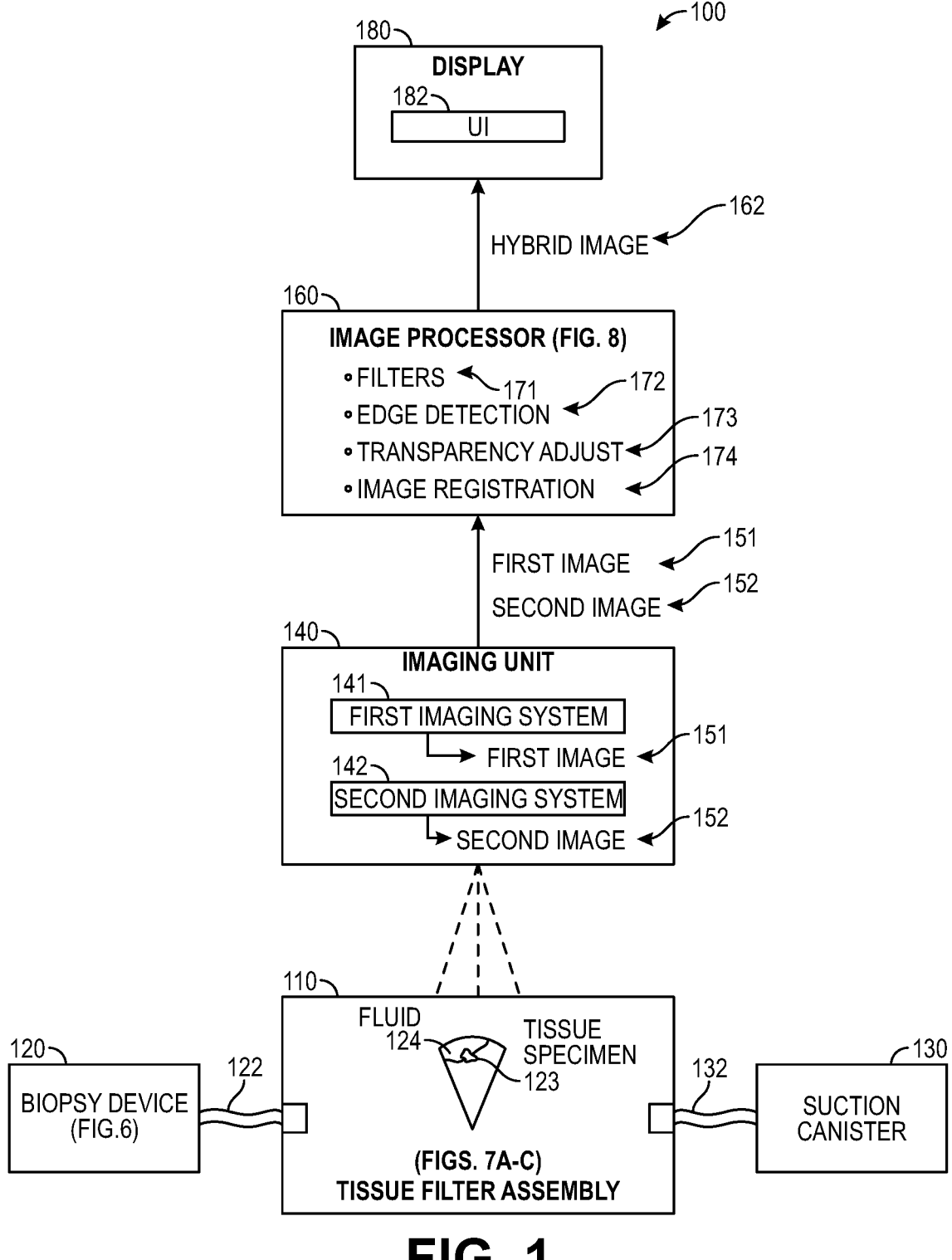
FIG. 1 is a block diagram of a tissue biopsy and handling system constructed according to one embodiment for imaging tissue specimens in the presence of fluids.

Embodiments provide for tissue biopsy and handling systems and associated image processing methods for multi-mode tissue specimen imaging in real time during a biopsy procedure and in the presence of one or more interfering fluids resulting from the procedure or utilized to transport the tissue specimen into a tissue storage compartment of a specimen tray of the tissue biopsy and handling system. In one embodiment, a tissue specimen is severed from a patient, aspirated through a vacuum tube together with a transport and/or bodily fluid such as saline, blood or a combination thereof, and deposited with the fluid into a storage compartment of a specimen tray. X-ray and optical images of the severed tissue specimen and fluid are acquired by the tissue biopsy and handling system while the tissue specimen is at least partially contained within or covered by the fluid (or combination of fluids). The tissue specimen, contained in or partially covered by the fluid, is imaged with different imaging devices, such as x-ray and optical camera imaging devices. Data of an x-ray image acquired by the x-ray imaging device and data of an optical image acquired by the optical camera imaging system are processed to generate a hybrid or fused image that is presented to a radiologist or user of the tissue biopsy and handling system in real-time during the procedure. For example, image acquisition and processing may be performed while the patient remains on a stereotactic table, after the severed tissue specimen has been aspirated through a vacuum tube and deposited into the specimen tray, and before the tissue specimen has been removed from the specimen tray, before the tissue specimen is removed from a housing of the tissue biopsy and handling system, and while the tissue specimen is at least partially or completely covered by fluid.

According to one embodiment, the hybrid image is constructed by adjusting the transparency of the optical image or portions thereof (while not adjusting transparency of the x-ray image), and the x-ray image is overlaid with optical image or extracted and/or processed portions thereof. The underlying x-ray image depicts internal structures such as lesions and calcifications that are not depicted in the optical image, and which may not be visible to the human eye. The overlaid optical image or portions thereof depicts external structures such as tissue specimen edges and surface contours that are attenuated or compromised in the x-ray image as a result of the interfering fluid during x-ray image acquisition. For these purposes, transparency adjustments may be applied to the entire optical image, e.g., evenly across the optical image, selectively applied to only certain portions of the optical image and/or by different amounts across the optical image, or certain portions of the optical image may be extracted and applied over the x-ray image. For example, the original transparency of the optical image may be increased by a first amount for only portions of the optical image depicting edges of the tissue specimen, whereas the transparency of other portions of the optical image that overlay x-ray image portions depicting calcifications, lesions or other objects of interest in the x-ray image may be increased to a second amount greater than the first amount or maximized. In other embodiments, an edge or periphery of the tissue specimen is detected and corresponding optical image portions are extracted and processed as needed for emphasis and applied over the x-ray image. In these manners, differential transparency allows for internal calcifications, lesions and other internal structures of the x-ray image to be visible to a radiologist while the transparency of the optical image or extracted portion thereof is maintained or only increased for semi-transparency (and less than the transparency adjustment of the middle or interior portion of the optical image) so that the tissue edges depicted in the optical image are emphasized compared to corresponding sections of the x-ray image. The resulting hybrid image is constructed so that the x-ray image is overlaid with the optical image or extracted portions thereof, internal tissue structures present in the x-ray image but not visible in the optical image or extracted portions thereof are still displayed, and edges of the tissue specimen depicted in the optical image or extracted portions thereof are utilized or emphasized to compensate for corresponding x-ray image portions that were attenuated or compromised by one or more fluids during x-ray imaging.

Referring to FIG. 1, a schematic of a tissue biopsy and handling system 100 (generally, tissue biopsy system 100) constructed according to one embodiment is shown. While the schematic of FIG. 1 shows certain features of tissue biopsy system 100, tissue biopsy system 100 may include components and features of a tissue biopsy system as disclosed in U.S. Pat. No. 9,492,130 B2, the contents of which are incorporated herein by reference as though set forth in full.

The exemplary tissue biopsy system 100 includes a tissue filter or tissue holder assembly 110 (generally, filter assembly 110). Filter assembly 110 is attached to and connected between a biopsy excision tool 120 and a suction canister 130. Biopsy excision tool 120 and filter assembly 110 are in fluid communication with each other via an inlet tube 122. Filter assembly 110 and suction canister 130 are in communication with each other through an evacuation suction tube 132. A vacuum source (not shown in FIG. 1) is in communication with evacuation suction tube 132 and/or suction canister 130 so that activation of vacuum source results in aspiration of a tissue specimen 123 excised by biopsy excision tool 120 and one or more bodily or added fluids 124 through inlet tube 122 into a tissue storage compartment of a specimen tray of filter assembly 110.

Tissue biopsy system 100 includes an imaging unit 140 that is positioned relative to filter assembly 110 so that excised tissue specimen 123 and fluid(s) 124 deposited into filter assembly 110 are positioned in respective fields of view of respective first and second imaging devices 141, 142 of imaging unit 140. Reference is made to a first or x-ray imaging device 141 and x-ray image 151 generated thereby, and a second or optical camera imaging device 142 such as a High Definition (HD) digital camera optical imaging device and optical image 152 generated thereby. X-ray and optical camera imaging devices 141, 142 may generate images or an image may be acquired by capturing a frame of a live video 1202 (as depicted in FIG. 12C) via frame capture button 1203 of UI 182. X-ray imaging device 141 utilizes photons within an energy range of about 10 keV to about 100 keV and wavelengths of about ~0.01 nm to ~10 nm, and optical imaging device 142 utilizes the visible spectrum (~400 nm to 700 nm). For ease of explanation, reference is made to a first or x-ray imaging device 141 and a second or optical camera imaging device 142.

Imaging unit 140 is in communication with an image processor 160 that receives inputs including data of x-ray and optical images 151, 152. Image processor 160 is configured to generate an output in the form of a hybrid image 162 based on respective processing of x-ray and optical images 151, 152. For example, image processor 160 may perform registration 174 of x-ray and optical images 151, 152, execute one or more filters 171 to x-ray image 151, detect edges or periphery portions 172 of optical image 152 to determine which portion of optical image 152 is subjected to opacity or transparency adjustments 173 to compensate for fluid 124 interference during x-ray image 151 acquisition and registration 174 of x-ray and optical images 151, 152. Image processor 160 is also in communication with a display 180 of tissue biopsy system 100 for display of hybrid image 162 to a user or operator of tissue biopsy system 100.

Referring to FIG. 2, with tissue biopsy system 100 illustrated in FIG. 1, at 202, after tissue specimen 123 and fluid 124 have been deposited into a tissue storage compartment of a specimen tray of filter assembly 110, x-ray imaging device 141 is activated to acquire x-ray image 151 of severed tissue specimen 123 at least partially contained in or covered by fluid 124. A portion of severed tissue specimen 123 may be covered by fluid 124, or there may be sufficient fluid 124 to completely cover severed tissue specimen 123. At 204, optical camera imaging device 142 is activated to acquire optical image 152 of severed tissue specimen 123 at least partially contained in or covered by fluid 124. At 206, and with further reference to FIG. 3, image processor 160 generates hybrid image 162 incorporating data of x-ray and optical images 151, 152. According to one embodiment, hybrid image 162 is generated by x-ray image 151 being overlaid with optical image 152. According to another embodiment, hybrid image 162 is generated by x-ray image 151 being overlaid with selected or extracted portions of optical image 152. At 208, hybrid image 162 is presented to user via a computer generated interactive user interface (UI) 182 through display 180 of tissue biopsy system 100. With this system configuration and image processing and as generally illustrated in FIG. 3, portions of optical image 152 depict external edges and surfaces of severed tissue specimen 123 more clearly than corresponding portions of x-ray image 151 that were attenuated by fluid

124 during x-ray image 151 acquisition, while x-ray image 151 portions depict internal structures of severed tissue specimen 123 more clearly than optical image 152. Opaque optical image 152 does not depict any internal structure of tissue specimen 123.

Figure 4A:
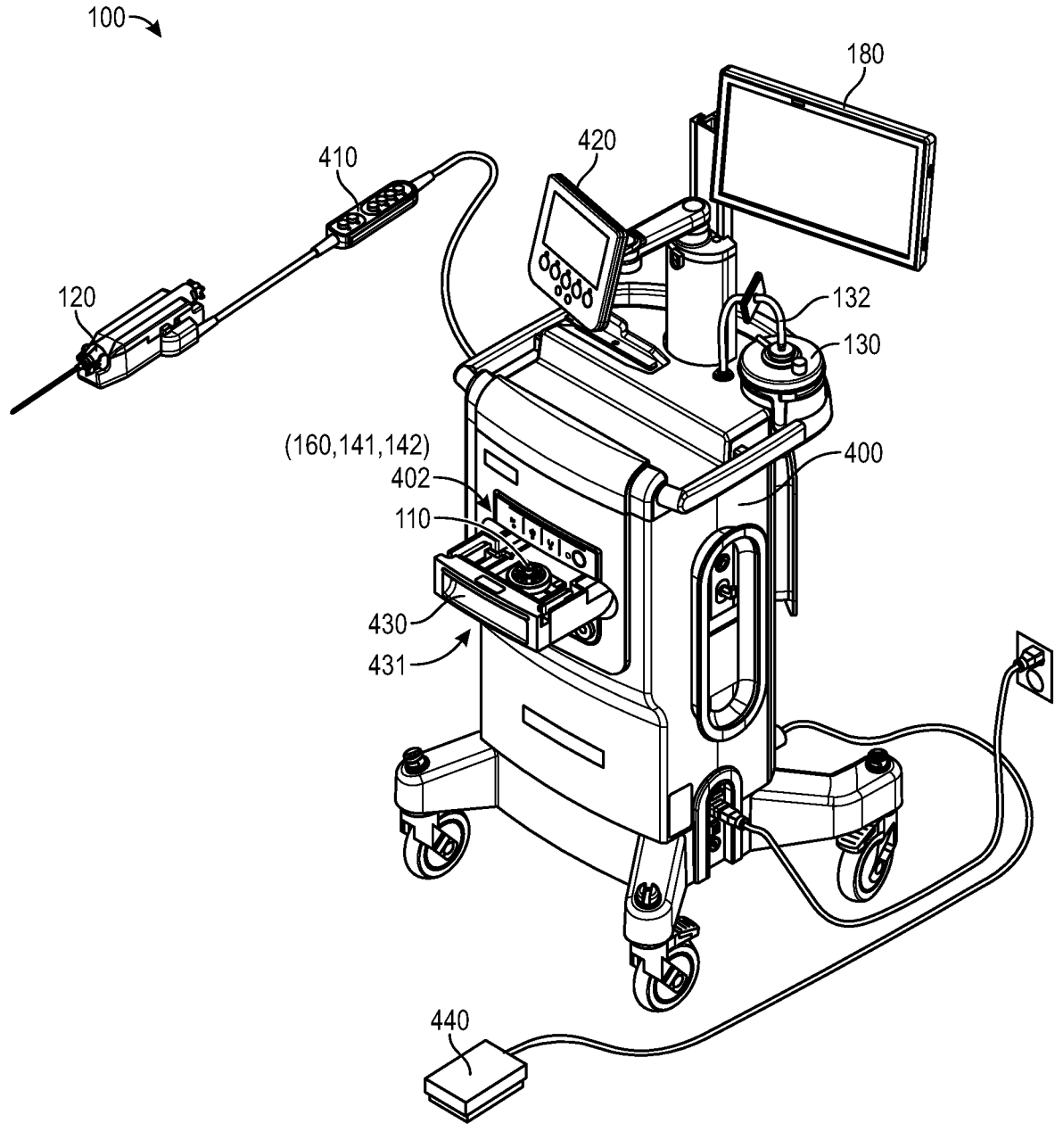
Figure 4B:
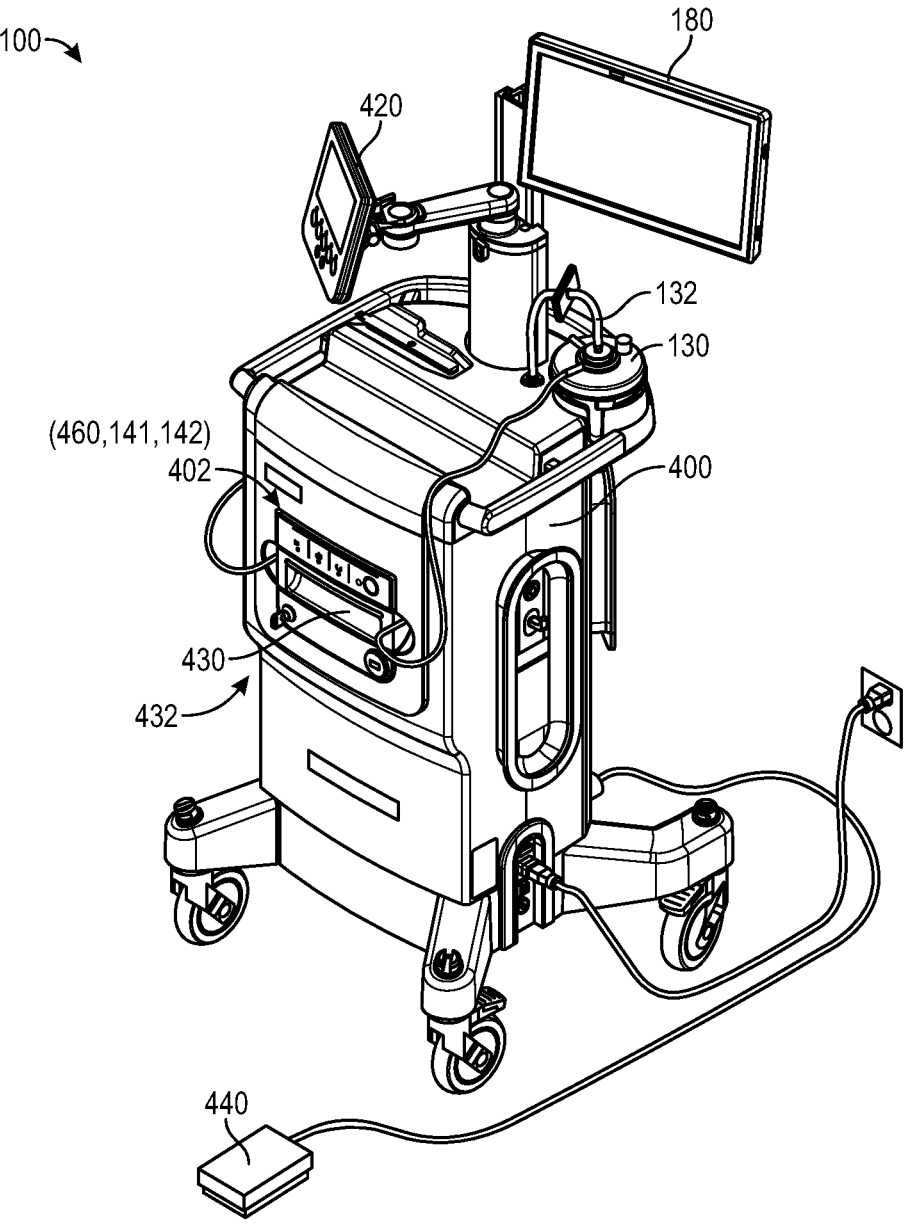

Referring to FIGS. 4A-B, an exemplary tissue biopsy system 100 incorporating embodiments for real-time imaging of tissue specimens 123 and fluid 124 to generate hybrid image 162 is illustrated. In the illustrated embodiment, exemplary tissue biopsy system 100 includes a main housing or cabinet 400 that includes an imaging cabinet 402 and a filter drawer 430. Filter drawer 430 can slide within imaging cabinet 402 between an open positon 431 (shown in FIG. 4A) and a closed position 432 (shown in FIG. 4B). In open position 431, filter drawer 430 is ejected or pulled out by radiologist to extend outwardly from imaging cabinet 402 thereby permitting insertion and removal of filter assembly 110. Filter drawer 430 is pushed or inserted into imaging cabinet 402 and into closed position 432 in which x-ray and optical camera imaging devices 151, 152 (located inside of imaging cabinet 402) are positioned relative to filter assembly 110 such that severed tissue specimen 123 and fluid 124 contained in filter assembly 110 are positioned in respective fields of view of respective x-ray and optical camera imaging devices 141, 142.

According to one embodiment, x-ray and optical camera imaging devices 141, 142 of imaging cabinet 430 are arranged so that tissue specimen 123 and fluid 124 are simultaneously in fields of view of x-ray and camera imaging devices 141, 142. In another embodiment, x-ray and optical camera imaging devices 141, 142 are arranged so that the x-ray image 151 is acquired with x-ray imaging device 141, and then filter assembly 110 containing tissue specimen 123 and fluid 124 is moved or rotated to position tissue specimen 123 and fluid 124 in the field of view of optical camera imaging device 142, which then acquires the optical image 152. Thus, x-ray and optical camera imaging devices 141, 142 may be fixed and arranged to acquire x-ray and optical images 151, 152 while filter assembly 110 is in particular position, or filter assembly 110 may be rotated for serial image acquisition by respective x-ray and optical camera imaging systems 141, 142. The position of one or more of the x-ray and camera imaging devices 141, 142 may also be adjusted within imaging cabinet 402, but for ease of explanation and not limitation, reference is made to filter assembly 110 being rotatable to place tissue specimen 123 and fluid 124 in respective fields of view of respective x-ray and camera imaging devices 141, 142 in imaging cabinet 402.

In the illustrated embodiment shown in FIG. 4A, biopsy excision tool 120 is in communication with a remote control 410 that is operable by radiologist to activate and control the mode of operation and other controls of biopsy excision tool 120. FIGS. 4A-B also illustrate suction canister 130 and associated evacuation suction tube 132 in communication with filter assembly 110 through main housing 400. Suction canister 130 may be a disposable canister that serves for collection, retention and disposal of waste generated during the biopsy procedure including for one or more fluids 124 such as excess saline and/or blood aspirated through filter assembly 110. Tissue biopsy system 100 may also include a footswitch 440 that allows the surgeon to manually activate and/or control the biopsy excision tool 120, and system mode or control status and/or system mode or control parameters can be displayed or adjusted via technologist control display 420.

Figure 5A:
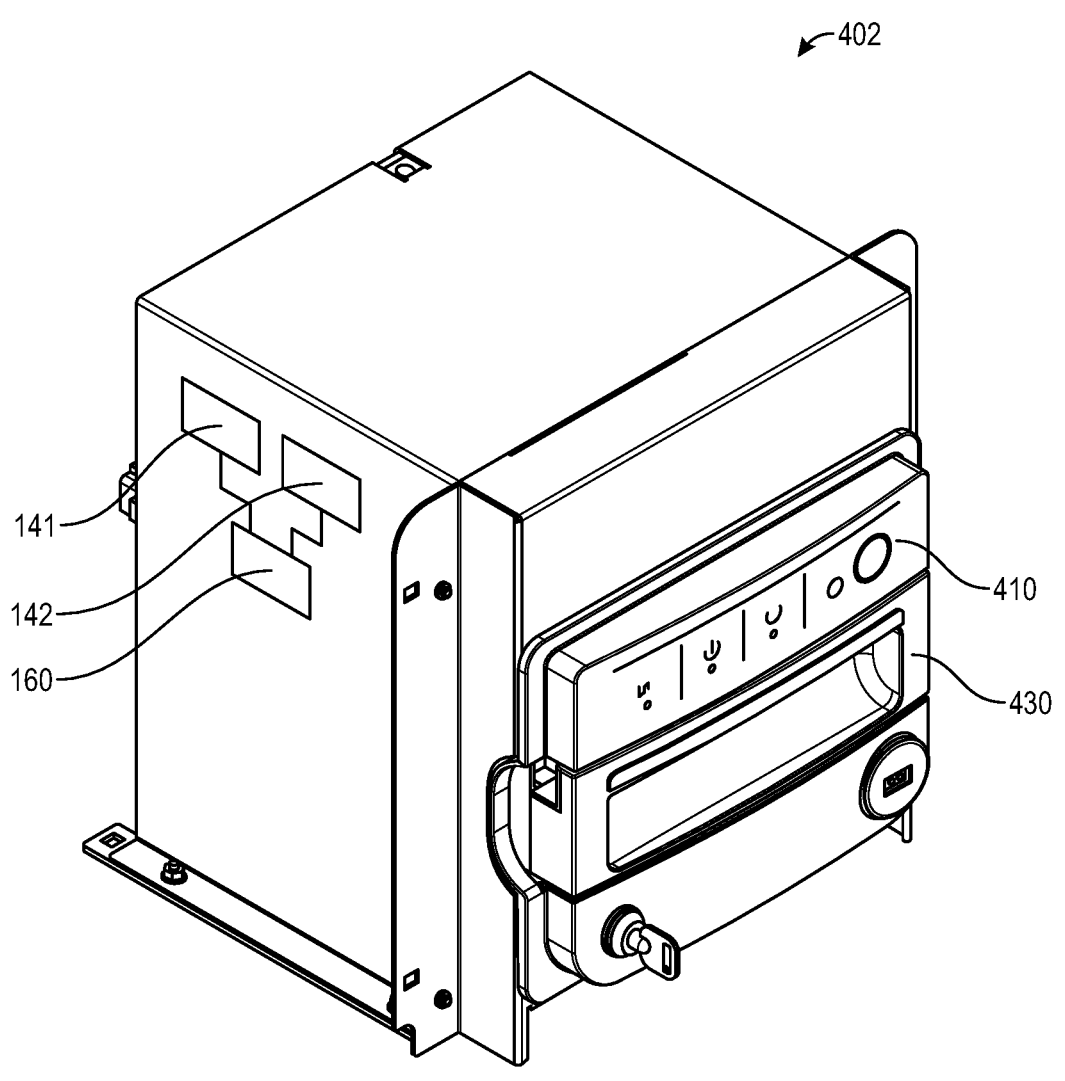
FIGS. 5A-B depicts an embodiment an imaging cabinet of a tissue biopsy and handling system constructed according to one embodiment.
Figure 5B:
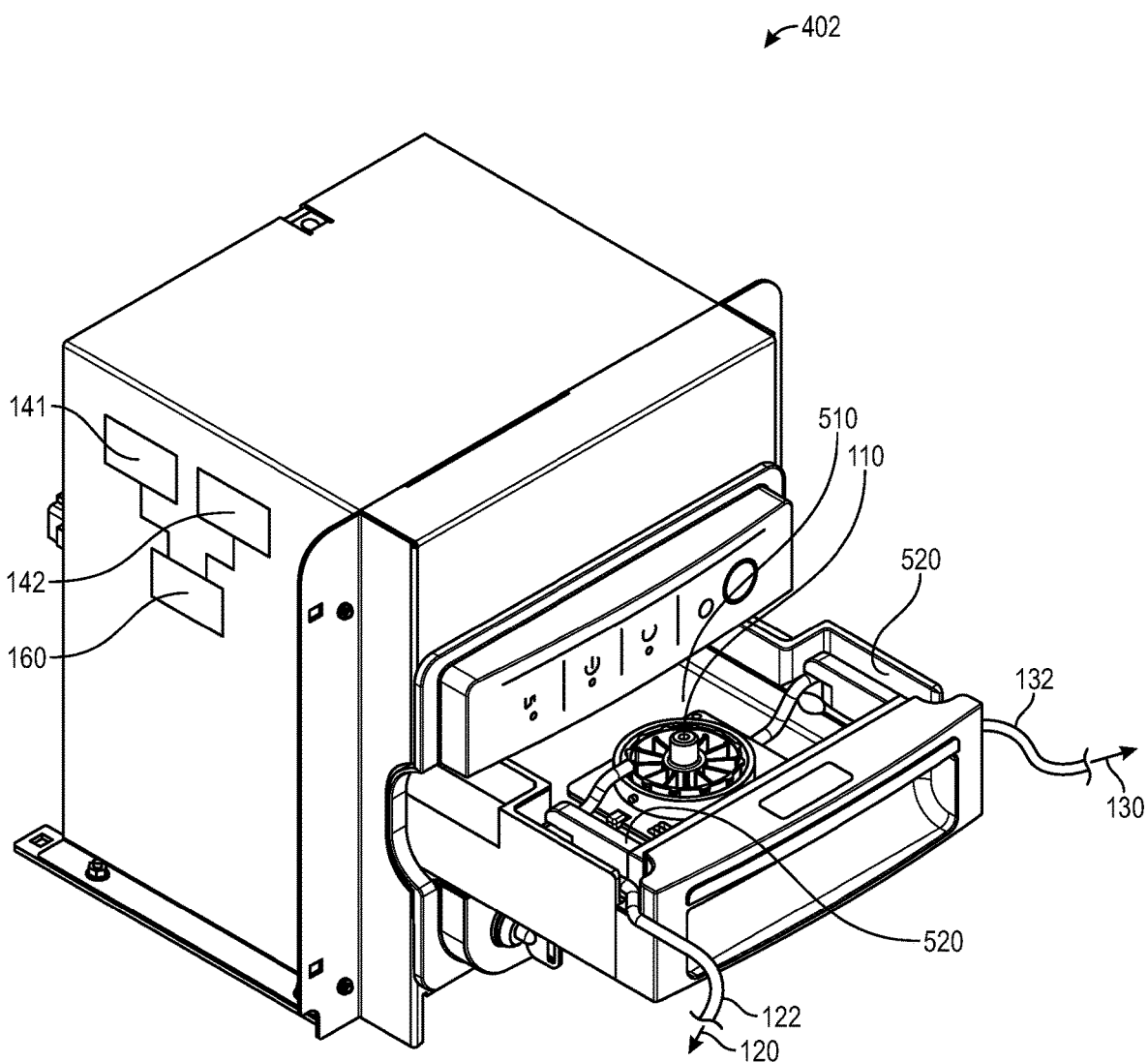

FIGS. 5A-B illustrate in further detail how imaging cabinet 402 of tissue biopsy system 100 can be configured for embodiments. In the illustrated embodiment, filter assembly 110 defining respective tissue storage compartments is removably inserted into filter drawer 430, which is slidably inserted into and removed from imaging cabinet 402. Filter assembly 110 is structured so that tissue storage compartments are positioned to be in communication with and between biopsy excision tool 120 via inlet tube 122 and suction canister 130 via evacuation suction or outlet tube 132. During use, tissue specimen 123 and fluid 124 excised by biopsy excision tool 120 are aspirated through inlet tube 122 and deposited into tissue storage compartments of filter assembly 110. Excess fluid 124 may be aspirated through evacuation suction tube 132 and into suction canister 130.

Imaging cabinet 402 includes or houses x-ray imaging device 141 and optical camera imaging device 142 as generally illustrated in FIGS. 5A-B, which depict x-ray and camera imaging devices 141, 142 in phantom and positioned above filter drawer 430 so that tissue specimens 123 and fluid 124 are positioned in respective fields of view of respective x-ray and camera imaging devices 141, 142. Image processor 160 may also be included in imaging cabinet 160 as generally illustrated in FIGS. 5A-B, but embodiments are not so limited. For example, image processor 160 or components thereof may be located remotely relative to tissue biopsy system 100 to allow for remote image processing and execution of machine intelligence and object detection within tissue specimens 123, but for ease of explanation, reference is made to real-time imaging and parallel acquisition of x-ray and optical images 151, 152.

Figure 12A:
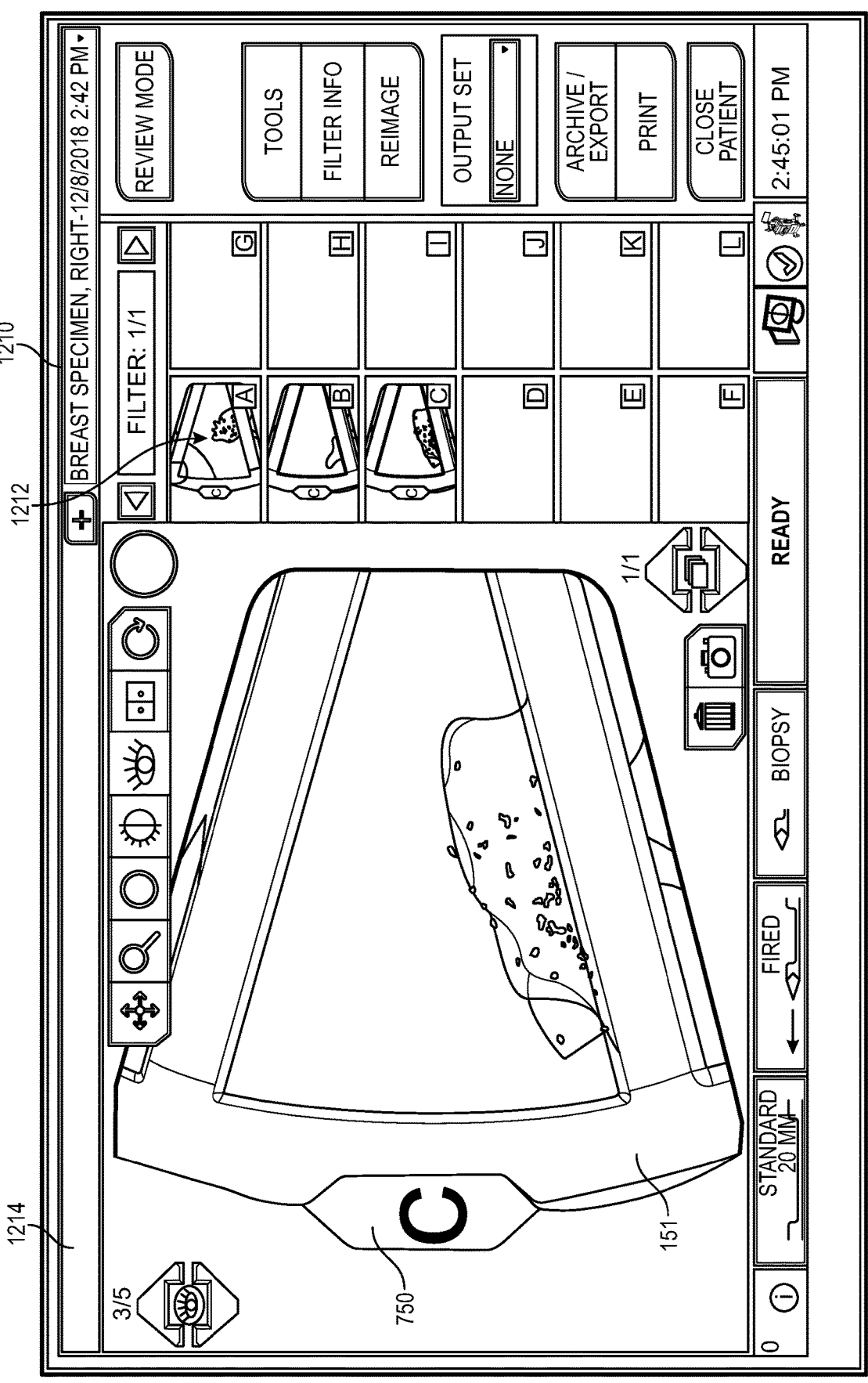
FIGS. 12A-C depict computer generated user interfaces that are presented by a tissue biopsy and handling system during acquisition of images using x-ray and optical camera imaging systems.
Figure 12B:
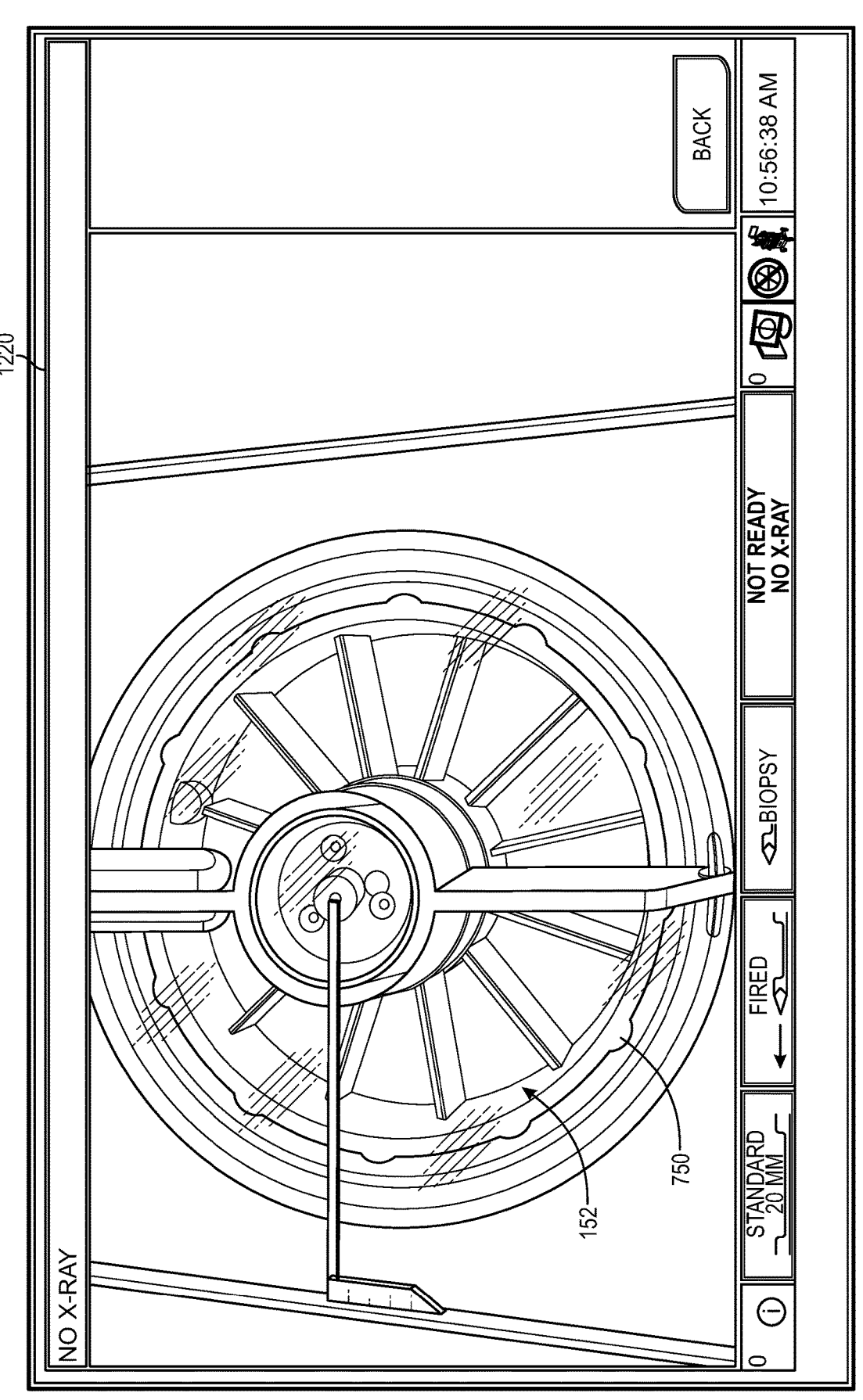
Figure 12C:
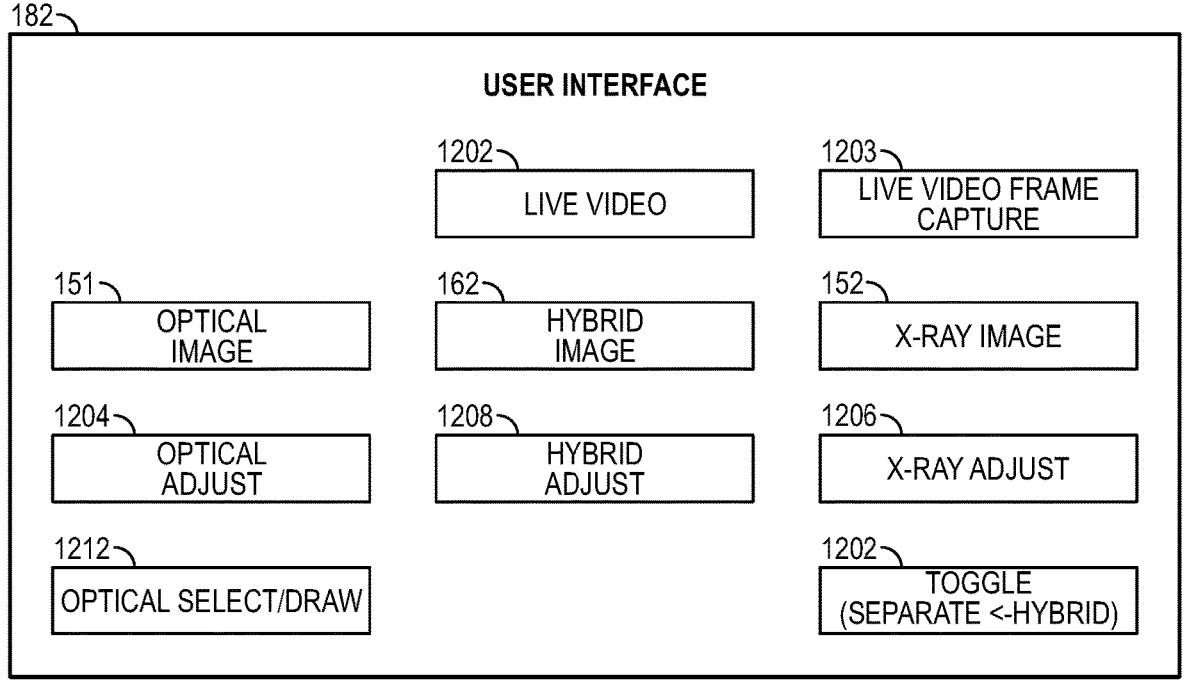

In embodiments involving first imaging device 141 in the form of an x-ray imaging device, imaging cabinet 402 includes a detector plate 510 for detecting emitted x-rays and generating x-ray image 151 (shown in FIG. 12A and depicted in UI 182 shown in FIG. 12C). X-ray and optical camera imaging devices 141, 142, imaging cabinet 402 and filter drawer 430 may be configured so that tissue specimen 123 and fluid 124 are in respective fields of view of respective x-ray and optical camera imaging devices 141, 142 while at a particular position, and in other embodiments, filter assembly 110 may be rotated or placed in a first position so that tissue specimen 123 and fluid 124 are in a first field of view of x-ray imaging device 151, and then rotated to place tissue specimen 123 and fluid 124 in a second field of view of optical camera imaging device 152.

Filter drawer 430 defines tubing channels 520 for inlet tube 122 and outlet or suction tube 132. Vacuum source (not shown) is in communication with suction or outlet tube 132 and/or suction canister 130 so that activation of vacuum source results in aspiration of tissue specimen 123 and fluid 124 through inlet tube 122 and into a tissue storage compartment of filter assembly 110. Waste or extra fluid may be aspirated through evacuation suction tube 132 into suction canister 130.

Referring again to FIGS. 4A-B, and with continuing reference to FIGS. 5A-B, imaging cabinet 402 includes a control panel 460 with buttons or UI elements (for control panels in the form of a touchscreen) to allow a user to select or adjust various operating parameters of biopsy system 100 such as imaging parameters or filters 171, and display 180 is provided to present hybrid image 162 generated according to embodiments through UI 182.

For example, image processor 160 may execute one or more filters 171 such as a noise filter, a brightness filter, or a mask for same, to x-ray image 151, and image processor 160 may execute edge or periphery detection 172 on optical image 152 to determine which portions of optical image 152 should be further processed with transparency adjustments 173. Image processor 160 is also in communication with computer display 180 of tissue biopsy system 100 to process user interactions via UI 182, e.g., to process user request for image modifications.

Figure 6:
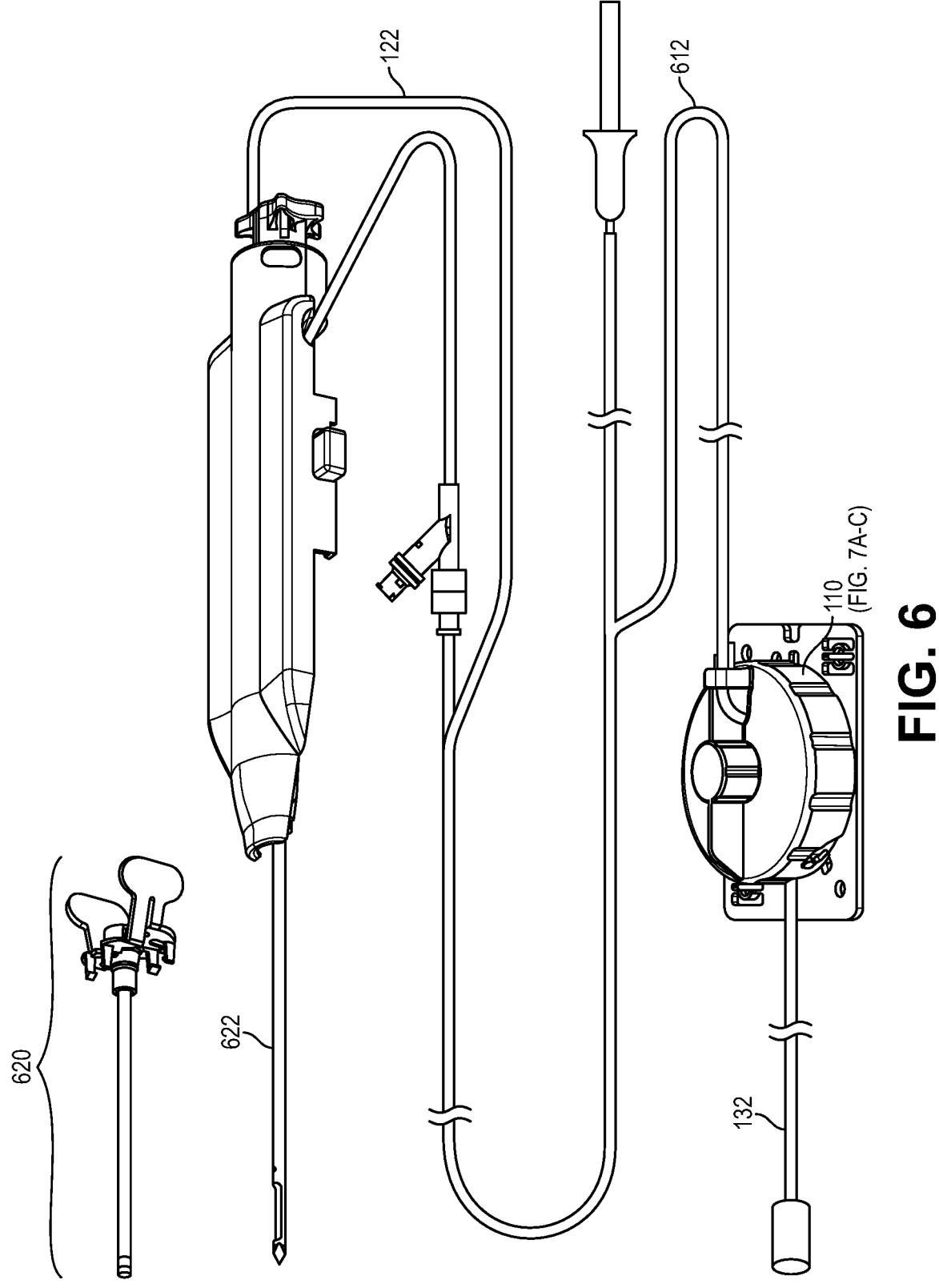
FIG. 6 depicts an example of a tissue biopsy and handling system that may be utilized to sever a tissue specimen in further detail and a tubing assembly through which fluids such as saline and blood may flow during a biopsy procedure.
Figure 7A:
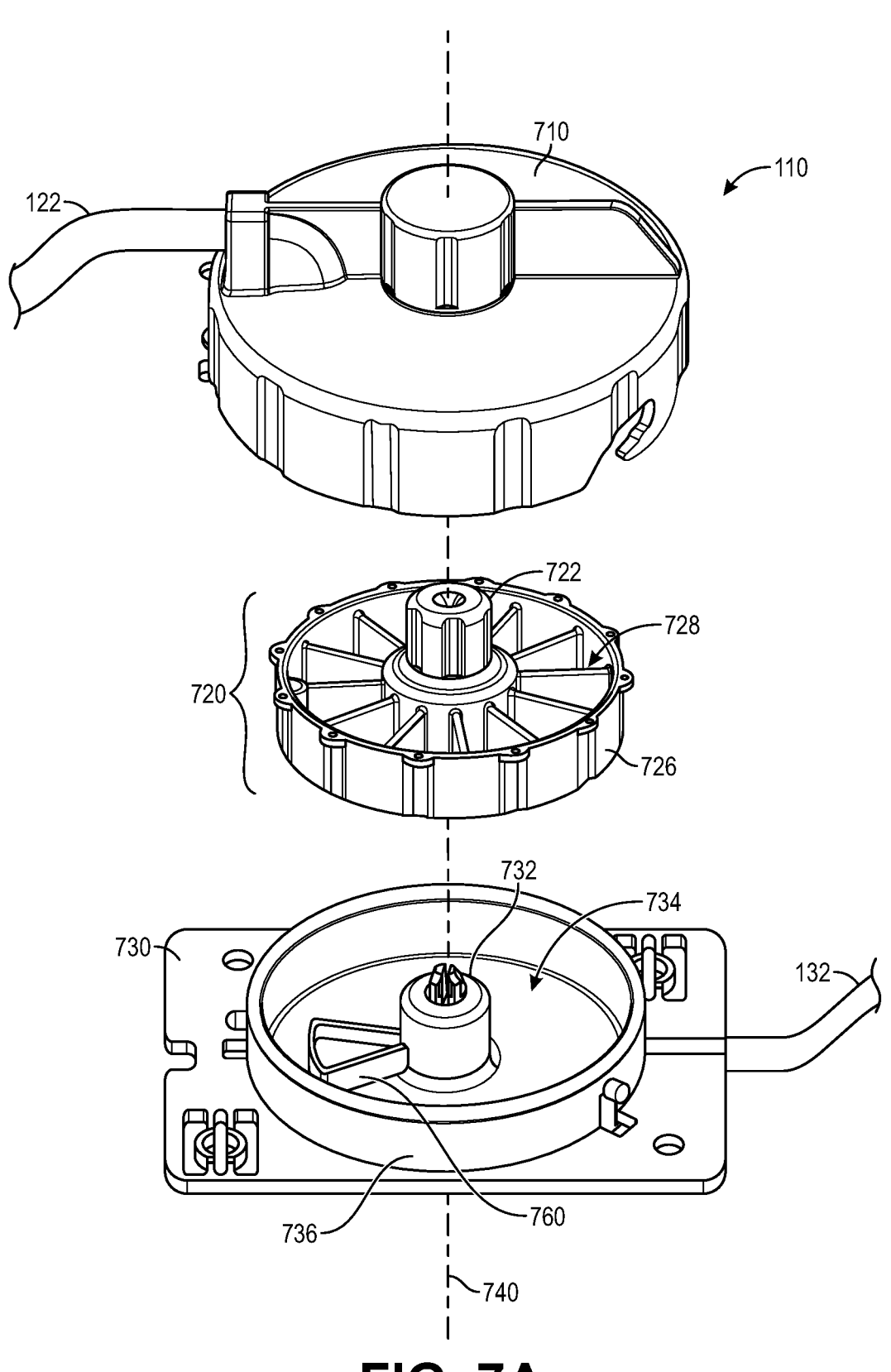
FIGS. 7A-C depict an example of a filter assembly of a tissue biopsy and handling system in further detail and including tissue storage compartments in which tissue specimens and fluids are deposited during a biopsy procedure, and FIG. 7D generally illustrates how a filter assembly may be positioned within fields of view of x-ray and optical camera imaging devices according to embodiments.
Figure 7B:
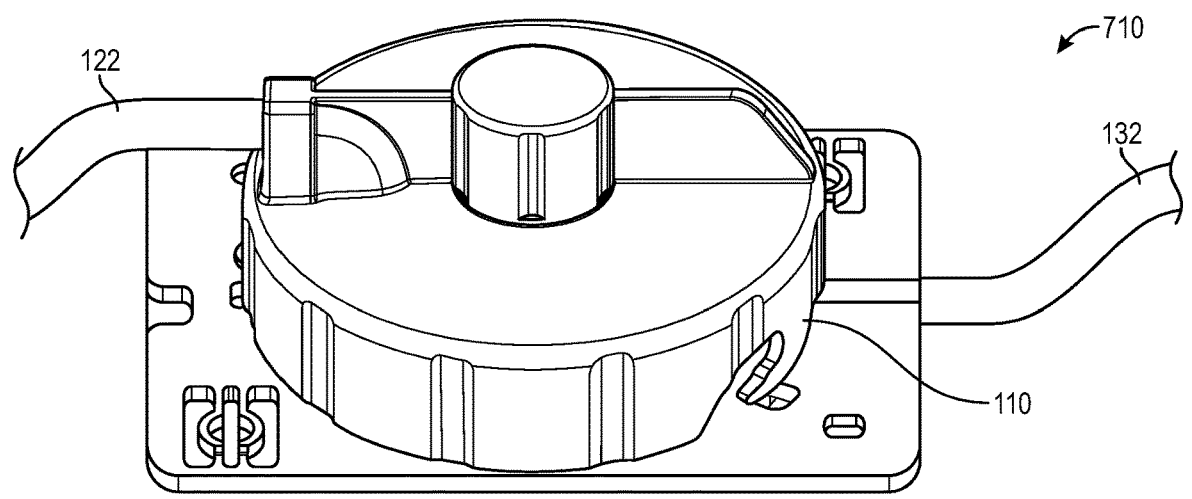
Figure 7C:
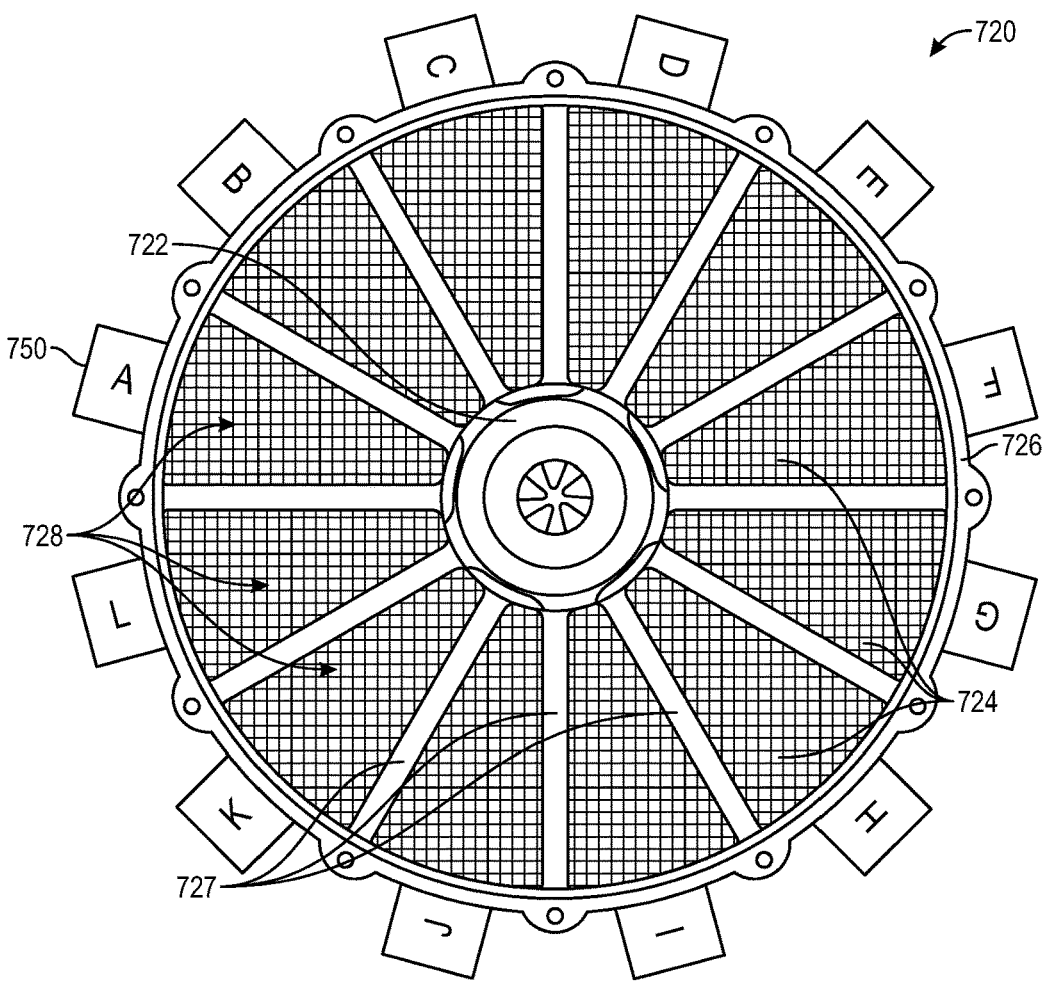
Figure 7D:
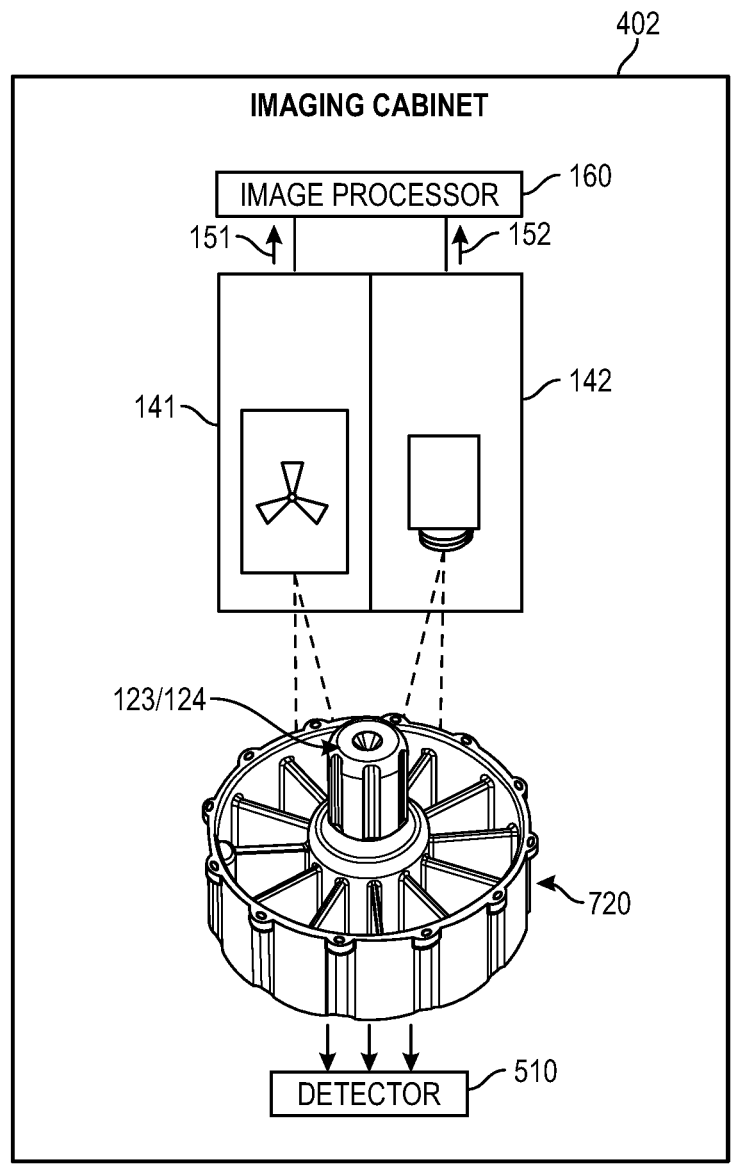

Referring to FIG. 6 and with further reference to FIGS. 7A-C, an exemplary biopsy excision tool 120 and filter assembly 110 are shown. A distal end of biopsy excision tool 120 includes an introducer 620 for insertion of a biopsy needle 622 that is attached to a driver of the biopsy excision tool 120 and is configured for tissue extraction. For these purposes, a proximal end of biopsy excision tool 120 is in communication with a saline/aspiration tubing assembly 610 comprising inlet tube 122 for delivery of saline fluid 124 and delivery of fluid to filter assembly 110. An exemplary saline/aspiration tubing assembly 610 as shown in FIG. 6 may include a suction line 612 through which tissue specimen 123 excised by needle 622 of biopsy excision tool 120 is aspirated together with fluid 124 such as saline that is introduced via one or more inlet values or saline lines 614. Excised tissue specimen 123 and fluid(s) 124 are aspirated through suction line 612 that is in communication with an inlet into filter assembly 110. An outlet of filter assembly 110 is in fluid communication with suction canister 130 via evacuation suction tube 132.

FIGS. 7A-C illustrate an exemplary configuration of filter assembly 110 that is in fluid communication between biopsy excision tool 120 and suction canister 130. Filter assembly 110 includes a housing or cover 710 and a base 730. Cover 710 removably attaches onto base 730 to define an interior or chamber in which a tissue specimen holder or tray, or filter holder or tray 720 (generally, specimen tray 720) is enclosed. Base 730 includes a spindle 732 that that receives a hub 722 of specimen tray 720 such that specimen tray 720 is rotatable about the about the spindle 732 and rotatable relative to base 730 and cover 710 about axis 740. In other words, base 730 and cover 710 are stationary and specimen tray 720 rotates within the chamber defined by base 730 and cover 710. Specimen tray 720 may be rotated using any suitable actuator such a magnetic system (not shown in FIGS. 7A-C) in which a magnetic drive system, attracted to magnetic elements disposed on specimen tray 720, rotates specimen tray 720 by magnetic force.

In the embodiment illustrated in FIGS. 7A-C, base 730 includes a bottom member or surface 734 and a cylindrical, circumferential outer sidewall 736 (generally, sidewall 736) extending upwardly from bottom member 734 and having an inner diameter so that specimen tray 720 is rotatable about hub 722 and within inner area defined by sidewall 736. In the embodiment illustrated in FIGS. 7A-C, specimen tray 720 also includes a bottom member or surface 724 and a cylindrical, circumferential sidewall 726 (generally, sidewall 726) extending upwardly from bottom member 724. Specimen tray 720 also includes a plurality of inner or dividing walls 727 (generally, dividing wall 727) extending radially from center or hub 722 to the inner surface of sidewall 726 to define respective tissue storage compartments 728. In the illustrated embodiment, the specimen tray 720 defines 12 tissue storage compartments 728a-1 (generally, tissue storage compartment 728). In the illustrated configuration, specimen tray 720 defines an angular arrangement of storage compartments 728 that are in the shape of "pie" or "wedge" shaped segments, each of which is defined by two dividing walls 727 and an arcuate portion of sidewall 726. Tissue storage compartments 728 are separated, and partially defined, by radially extending dividing walls 727. It will be understood that specimen tray 720 may define other numbers of tissue storage compartments 728 and have other configurations such that FIGS. 7A-C are provided to illustrate one example of how a filter assembly 110 may be structured.

During a biopsy procedure, tissue samples 123 and fluid (s) 124 are aspirated through biopsy needle 622 to in-line tissue storage chamber 728. Tissue chamber indicators 750a-1 (generally, compartment indicators 750) are provided to identify respective tissue storage compartments 728 and respective tissue specimens 123 therein. Indicators 750 may be printed or engraved alpha-numeric indicators. For example, radiopaque ink may be utilized for indicators 750 so that they are visible in x-ray image 151 and optical image 152. In the illustrated embodiment, indicators 750 are alpha indicators in the form of letters A-L to identify respective 12 tissue storage compartments 728A-L.

In certain embodiments, bottom surface 724 of specimen tray 720 includes a porous filter material. Filter material may be a single filter, such as a filter sheet that covers the entire bottom of specimen tray 720 and through which excess fluid 124 flows into suction canister 130. Alternatively, filter material may be individual filters disposed on the bottom of each tissue storage compartment 728.

Certain embodiments may involve initially reducing fluid 124 in tissue storage compartments 728 before tissue specimen 123 imaging, and then embodiments are executed for image processing of tissue specimens 123 in the presence of remaining fluid 124. According to one embodiment, a fluid management device 760 may be disposed in the interior of base 730. Embodiments may involve removal of fluids 124 from tissue storage compartment 728 with a mechanical device in the form of fluid management device 760 in combination with image processing of different x-ray and optical images 151, 152 acquired by different first and second imaging devices 141, 142 to address fluids 124 remaining in tissue storage compartments 728 and that continue to interfere with imaging of severed tissue specimens 123. It will be understood that various mechanical fluid management devices 760 may be utilized and utilized in combination with image processing of embodiments to reduce the amount of fluid 124 that is imaged. Thus, certain fluid management devices 760 are described herein as non-limiting examples how fluids 124 that are subjected to image processing can be reduced and removed from a tissue storage compartment 728. It will also be understood that embodiments may not involve mechanical fluid management devices 760 and instead fluids 124 as deposited in a tissue storage compartment 760 are addressed by image processing according to embodiments as described in further detail below.

In the illustrated embodiment, fluid management device 760 in the form of a "pie" or "wedge" shaped reservoir extending upwardly from bottom surface 734 and located under specimen tray 720. The fluid reservoir may be filled with fluid 124 during a biopsy procedure, and as fluid 124 from specimen tray 720 is removed, fluid 124 in reservoir 760 may overflow into base 730. For this purpose, reservoir wall 760 can have a top edge that is in close proximity, but not touching, the bottom of specimen tray 720 such that the top edge of reservoir wall is close enough to the bottom of specimen tray 720 and fluid 124 is drawn away from storage compartments of 728 of specimen tray 720 as each of the storage compartments is rotated over reservoir 760. Stated in another way, a fluid path is formed between the fluid 124 within the storage compartment 728 and fluid 124 within the reservoir 760. The fluid path allows the fluid 124 within the specimen tray 720 to be drawn out from tissue storage compartment 728 to reservoir 760. Thus, tissue compartments 728 may be configured to remove at least some of the fluid(s) 724 deposited during a biopsy procedure, and image processing is then employed to address remaining interfering fluid 124 that remains after a mechanical fluid management device 760 has been utilized for fluid 124 reduction. Thus, whether by image processor 160 or by image processor 160 in combination with fluid management device 760, embodiments provide a high quality images of tissue specimens 123 that are at least partially contained within or covered by fluid 124 and do so in real time during a biopsy procedure.

Having described various aspects, structure and operation of an exemplary biopsy system 100 and components thereof including mechanical fluid management devices 760 that can be utilized in conjunction with embodiments of processing images of tissue specimens 123 at least partially covered by one or more fluids 124, image processing embodiments are described in further detail with reference to FIGS. 8-17B. For ease of explanation, reference is made to tissue specimens 123 at least partially covered by one or more fluids 124, examples of which may include one or more of blood, saline, anesthetic, bio-fluids, etc., and particular non-limiting examples of blood of the patient released from the biopsy procedure and saline utilized to transport the specimen 123 through biopsy excision tool 120 and inlet tube 122 to tissue storage compartment 728.

Figure 8:
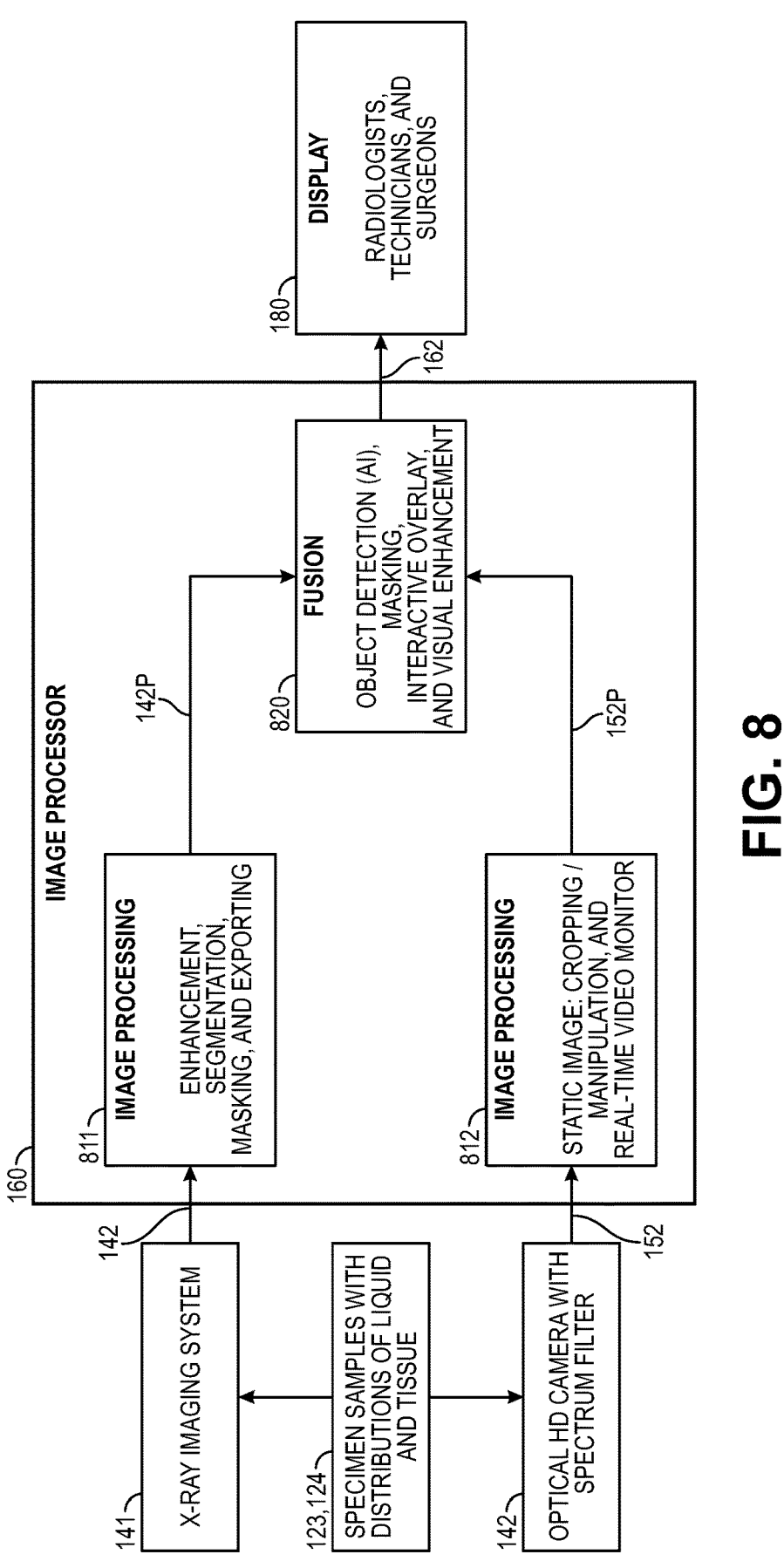
FIG. 8 is a system flow diagram of an image processor of a tissue biopsy and handling system constructed according to one embodiment for imaging tissue specimens in the presence of fluids.

Referring to FIG. 8, one embodiment of image processor 160 of biopsy system 100 includes multiple image processing elements for different imaging devices. For ease of explanation, reference is made to a first imaging device 141 in the form of an x-ray imaging device and to a second imaging device 142 in the form of an optical camera imaging device. According to one embodiment, x-ray imaging device 141 generates x-ray image 151 that depicts external or surface portions of tissue specimen 123 and internal portions of tissue specimen 123 that are not visible to the human eye, whereas optical camera imaging device 142 generates optical image 152 that depicts only external surfaces of or surface portions of tissue specimen 123 visible to the human eye. Thus, optical image 152 does not image internal portions of tissue specimen 123 such as calcifications and lesions that are not visible to the human eye.

In the illustrated embodiment, image processor 160 includes a first pre-processor 811 for x-ray images 151, a second pre-processor 812 for optical images 152 and an image fusion processor 820 in communication with the x-ray pre-processor 811 and optical image pre-processor 812. X-ray image 151 is provided as an input to x-ray image pre-processor 811, and optical image 152 is provided as an input to optical image pre-processor 812. The output generated by x-ray pre-processor 811 and provided as an input to image fusion processor 820 is referred to as a processed x-ray image 151p ("p" referring to processed by x-ray pre-processor 811).

X-ray pre-processor 811 may execute enhancement, segmentation and masking on x-ray image 151 as needed, and the output 151p of x-ray pre-processor 811 is exported as an input to image fusion processor 820. For example, x-ray pre-processor 811 may execute one or more image processing methods to prepare x-ray image 151 for eventual fusion with optical image 152 by emphasizing and enhancing portions of x-ray image 151 that depict tissue specimen 123 rather than adjacent or surrounding physical structures. For example, x-ray pre-processor 811 may involve executing one or more filters 171 on x-ray image 151. Filters 171 may include a noise filter to reduce x-ray image 151 noise and generate a cleaner x-ray image 151. Filters 171 may also include a brightness filter that eliminates portions of x-ray image 151 that have a brightness level exceeding a maximum brightness level to reduce x-ray image 151 bright spots and/or that eliminates portions of x-ray image 151 that have a brightness level that is less than a minimum brightness level to reduce dark spots. Brightness filter 171 may use a pre-determined brightness criteria (one or both of a high brightness and low brightness criteria) to exclude or mask bright and dark portions of x-ray image 151. Remaining portions of x-ray image 151 are less likely to be erroneously interpreted as something else, such as a calcification or other object of interest, rather than an irrelevant bright spot within the x-ray image, and thus more likely to depict a portion of tissue specimen 123 rather than filter assembly 110 walls or other structures that appear as white or bright portions in x-ray image 151.

Thus, by utilizing low and high brightness filters 171, the remaining or processed x-ray image 151$p$ data is more likely to depict tissue specimen 123 rather than non-tissue elements or filter assembly 110 structures such as side walls 726 or dividing walls 727. X-ray pre-processor 811 may also execute brightness adjustments such as reducing the brightness of the x-ray image 151 or portions thereof that have brightness levels greater than a maximum brightness value. These adjustments may be helpful to avoid or reduce false positives and erroneous interpretations of normal tissue as a calcification, lesion or other object of interest. Filters 171 of x-ray pre-processor 811 may also involve segmentation to further differentiate x-ray image 151 portions depicting tissue specimen 123 from adjacent or surrounding structures of specimen tray 120, e.g., by use of one or more of a pixel graph, a brightness or contrast filter, to further distinguish walls, tissue compartments and other structures of filter assembly 110 as well as magnetic components used to rotate the specimen tray 120.

X-ray pre-processor 811 may also utilize template or geometric data of specimen tray 120 structures such as geometric data of tissue storage compartments 728, sidewall 726 and dividing walls 727, and with these known dimensions, centers, and geometric configurations, tissue specimen 123 boundaries within a tissue storage compartment 728, whether placed in a middle of a tissue storage compartment 728 or in contact with a wall, to distinguish portions of tissue specimen 123 from adjacent or surrounding physical structures. It will be understood that x-ray pre-processor 811 may employ various filters 171 and x-ray image 151 processing to enhance or improve portions of x-ray image 151 and provide processed x-ray image 151$p$ as an input to image fusion processor 820.

Second or optical pre-processor 812 is executed on optical image 152 and executes different image processing methods than x-ray pre-processor 811. Optical pre-processor 812 receives optical image 152 as an input and executes one or more image processing methods to generate a processed optical image 152$p$. Optical pre-processor 812 prepares optical image 152 or selected or extracted portions thereof for eventual fusion with processed x-ray image 151$p$. For ease of explanation, reference is made to x-ray image 151 and optical image 152 provided as inputs to image fusion processor 820.

Optical pre-processor 812 may crop optical image 152 so that dimensions or view of optical image 152 are the same as dimensions or view of x-ray image 151, or dimensions or view of tissue specimen 123 depicted in optical image 152 are the same as dimensions or view of tissue specimen 123 depicted in x-ray image 151. Cropping of optical image 152 may be needed to compensate for the field of view of the lens of camera imaging device 142 utilized. While embodiments are described with reference to cropping one of the images generated by one of the imaging devices, cropping may not be necessary, or both of the x-ray and optical images 151, 152 can be cropped as needed for image registration 174.

For example, x-ray image 151 may be an image of tissue specimen 123 and fluid 124 within a single tissue storage compartment 728, whereas multiple tissue specimens 123 and fluid 124 in respective tissue compartments 728 are depicted in optical image 152 due to the field of view provided by camera lens and positioning of camera imaging device 141 relative to tissue storage compartments 728. Optical pre-processor 812 may process optical image 152 to include a single tissue storage compartment 728 or to dimensionally and spatially for register x-ray image 151 and optical image 152.

Optical pre-processor 812 also performs tissue edge detection 172 within optical image 152 based on tissue specimen 123 in tissue storage compartment 728, a geometric structure and dimensions of specimen tray 720 and wall components thereof, and/or tissue storage compartment 728 identifiers or indicia such as a printed or engraved number or letter associated with a tissue storage compartment 728. Edge detection 172 may be used for registration of x-ray image 151 and optical image 152. Optical pre-processor 812 may also address interfering elements such as bubbles in saline/blood fluid 124, e.g., by use of an infrared filter, which may be applied to a lens of optical camera imaging system 142 to further enhance and differentiate tissue specimen 123 from interfering fluids 124. Machine intelligence and training of a neural network may also be employed by optical pre-processor 812 for tissue edge or boundary detection and for boundary or edge detection in view of bubbles in saline/blood fluid 124.

Edge detection 172 may be used for determining how optical image 152 or portions thereof are processed (e.g., by transparency adjustment 173) or extracted for graphical processing and generation of hybrid image 162. In one embodiment, optical image 152 transparency is adjusted so that portions of optical image 152 corresponding to detected edges or periphery is modified to be semi-transparent, whereas other optical image 152 portions that do not depict edge or periphery are modified to have an even higher transparency level to be substantially or entirely transparent. Optical image transparency adjustments 173 may be applied to contiguous optical image 152 portions or separated portions or pixels. For example, transparency adjustments 173 may be made to all edges, or the entire periphery of tissue specimen depicted in optical image 152, or transparency adjustments 173 may be made to only certain edge or periphery sections of tissue specimen 123 depicted in optical image 152 such as edge or periphery sections that are not adjacent to a specimen tray 720 wall since an edge of a tissue specimen 123 abutting a wall is more clearly defined compared to an edge of a tissue specimen 123 that does not contact a specimen tray 720 wall. As another example, transparency adjustments 173 in optical image 152 may be made for corresponding sections of x-ray image 151, e.g., certain x-ray image 151 portions having brightness and/or contrast levels less than a desired or pre-determined contrast and/or brightness levels.

According to another embodiment, optical pre-processor 812 receives optical image 152 as input and selects or extracts only certain portions of the optical image 152 corresponding to the detected edge or periphery of tissue specimen 123 depicted in optical image 152, and extracted or selected portions may form a "ring" type structure. While a tissue specimen periphery or boundary has an irregular shape and most likely is not in the shape of a circle, reference is made to a ring structure to refer to the tissue specimen periphery for ease of explanation. Selected or extracted optical image 152 portions may be adjusted for emphasis as necessary by transparency reduction to be semi-transparent. According to another embodiment, optical pre-processor 812 detects an edge or periphery of tissue specimen 123 and executes graphical processing to generate graphical representations or extraneous markers or identifiers for the detected edge or periphery. Thus, optical pre-processing may involve or output optical image 152, portions of optical image 152 and generated graphical representations based on respective portions of optical image 152. For ease of explanation, reference is made to optical image 152 or portions thereof, which is defined to include image portions and graphical representations corresponding to same.

With continuing reference to FIG. 8, the resulting processed x-ray image 151p and processed optical image 152p or extracted and processed optical image 152p or generated graphical data are received by image fusion processor 820 as an input. For ease of explanation, reference is made to image fusion processor 820 receiving x-ray image 151 and optical image 152 as inputs, noting that pre-processing described above may be applied to one or both of these images. Image fusion processor 820 applies processed optical image 152 or portions thereof over processed x-ray image 151 to form hybrid image 162. Depending on the type of optical pre-processing 812 employed, hybrid image 162 may be generated as a "stack" of x-ray image 151 and optical image 152, a stack of x-ray image 151 and a selected portion of optical image 152 (e.g., a ring type image based on edge detection), a stack of x-ray image 151 and a graphical representation generated based on detected edges of tissue specimen 123 depicted in optical image 152, or as a single image in which extracted or selected optical image 15 portions or graphical representations based thereon replace corresponding portions of x-ray image 151. In other words, image fusion processor 820 may apply optical image 152 or portions thereof over x-ray image 151 or modify x-ray image 151 to replace or integrate optical image 152 portions into x-ray image 152, and hybrid image 162 is constructed by x-ray image 151 and optical image 152 or portions thereof being registered to or aligned with each other.

The resulting hybrid image 162 compensates for fluid 124 attenuation of the edge or periphery depicted in x-ray image 151 during x-ray image 151 acquisition. For example, a portion of the optical image 152 corresponding to an edge or periphery of the depicted tissue specimen 123 may have its transparency adjusted from digital image transparency or 0% transparency to a semi-transparency level that allows for a clearer depiction of the edge or periphery in optical image 152 to compensate for attenuated edge or periphery portions of x-ray image 151 while other portions of optical image 151 are adjusted to have a higher transparency level (e.g., substantially or entirely transparent) so that internal tissue specimen 123 portions depicted in x-ray image 151 are visible through and not obscured by overlaid or integrated optical image 152 or portions thereof. As another example, portions of the edge or periphery of tissue specimen 132 depicted in optical image 152 are extracted and processed to graphically emphasize the edge or periphery, and the graphically generated portions are then applied over or integrated within x-ray image 151. This may result in a "periphery" or "ring" that is extracted from optical image 152 and applied over or integrated into x-ray image 151 and has partial transparency to compensate for attenuation of periphery or ring in the underlying x-ray image 151. With this extracted periphery or ring, no interior or middle portion of optical image 151 extends across other portions of x-ray image 151 such that internal portions of tissue specimen 123 depicted in x-ray image 151 are not obscured by optical image 152 and are clearly visible through the transparent "hole" defined by extracted ring portion of optical image 151 or graphically generated portions based on same.

The generated hybrid image 162 is presented to the user through an interactive UI 182 and display 180 of biopsy system 100. Interactive UI 182 allows for user adjustment 1208 of aspects of hybrid image 162 and adjustment 1204, 1206 of individual x-ray and optical images 151, 152 or portions thereof. Image processor 160 may also execute object detection methods on hybrid image 162 and/or on one or more of x-ray image 151, processed x-ray image 151p, optical image 152 and processed optical image 152.

Referring to FIG. 9, a computer-implemented method 900 for tissue specimen 123 excision and image processing in the presence of fluid 124 is described in further detail with reference to the exemplary biopsy system 100 components and operability and processing described above. It will be understood that various processing shown in FIG. 9 may be repeated or configured for biopsy procedures of multiple tissue specimens 123 into respective tissue storage compartments 728 of specimen tray 720.

Figure 10A:
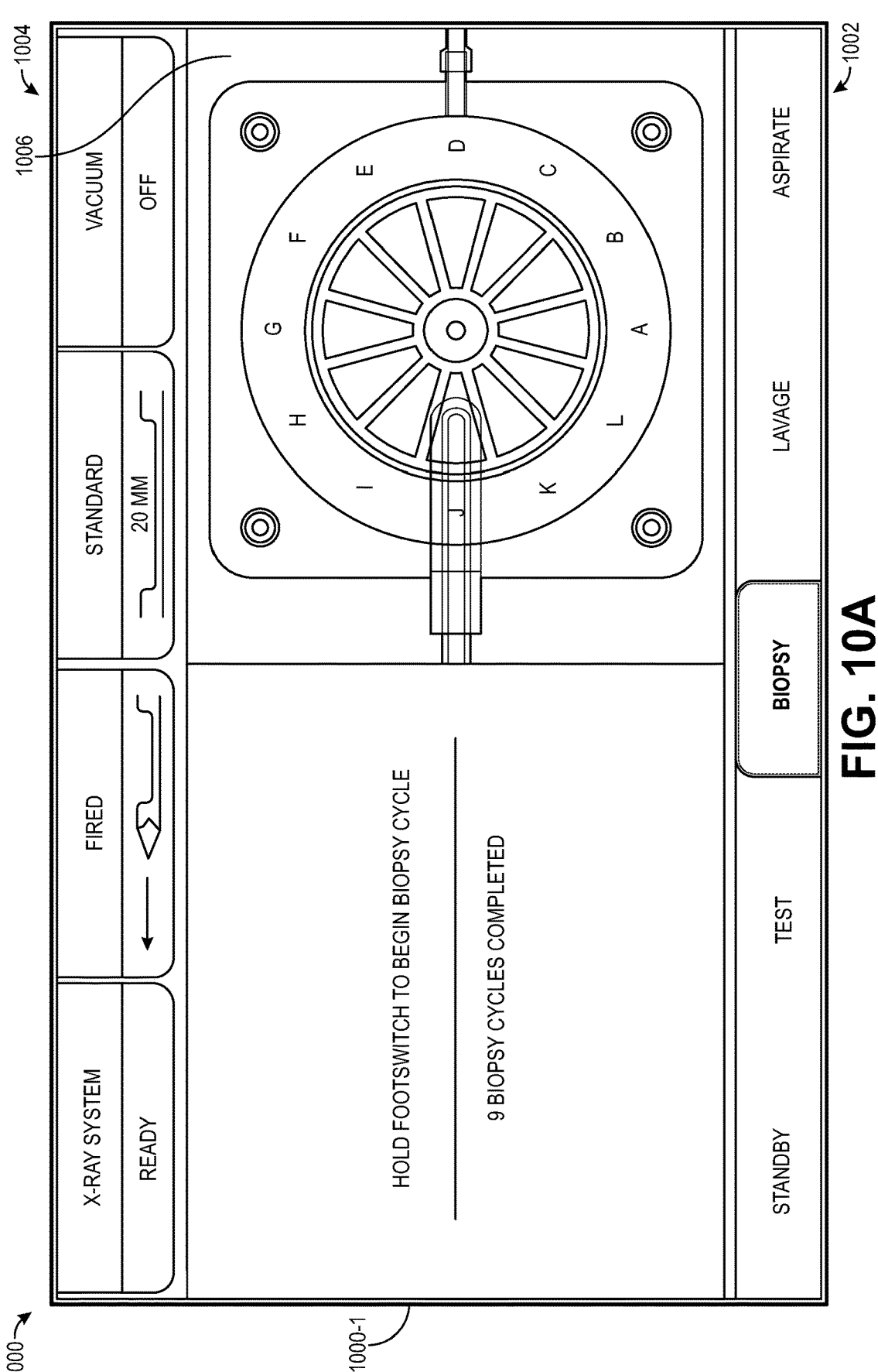
FIGS. 10A-B depict examples of computer generated user interfaces presented by a tissue biopsy and handling system for different stages of a tissue specimen biopsy.
Figure 10B:
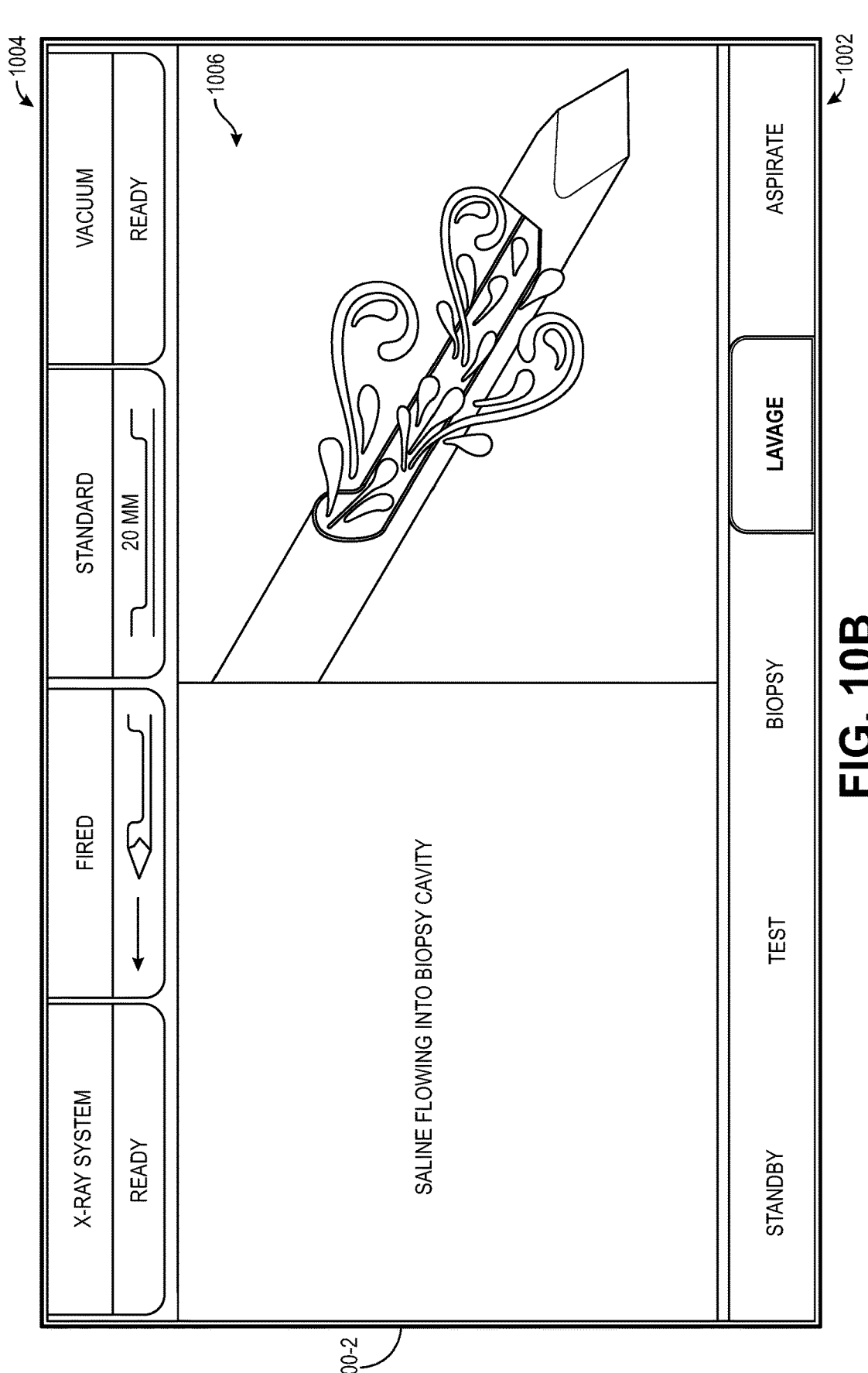

At 902, a vacuum source is activated and specimen transport fluid 124 such as saline is introduced into biopsy excision tool 120 via one or more tubes of tubing assembly 610 in preparation for a tissue specimen biopsy procedure. Fluid 123 flow and aspiration may be activated by initiation of a cutting cycle in response to user input via remote control 410 and/or footswitch 440. For example, in interactive computer generated UI 1000 depicted in FIG. 10A, a first UI screen 1000-1 includes tabs 1002 for mode selection (such as "biopsy"), status indicators 1004 (e.g. vacuum off), and a graphical depiction 1006 of which tissue storage compartment 728 is ready to receive a severed tissue specimen 123 and fluid 124 from biopsy excision tool 120. For example, interactive UI 1000 shown in FIG. 10A depicts biopsy excision tool 120 or associated inlet tube 122 tool in fluid communication with tissue compartment 728 identified by indicia 750 "J." First interactive UI screen 1000-1 also includes an instruction 1008 to the operator to "Hold footswitch to begin biopsy cycle." FIG. 10B depicts a second interactive UI screen 1000-2 including an indicator of saline fluid 124 flow through biopsy excision tool 120.

Referring again to FIG. 9, at 904, biopsy excision tool 920 is activated by the user via remote control 410 and/or footswitch 440 to sever tissue specimen 123 from patient. Severed tissue specimen 123 is aspirated with fluid 124 through biopsy excision tool 120 and into inlet tube 122 or portion of tubing assembly 610 at 906. At 908, severed tissue specimen 123 and fluid 124 are delivered through inlet tube 122 and deposited together into storage compartment 728 of specimen tray 720.

Continuing with reference to FIG. 9, at 910, excess or waste fluid 724, which may be a combination of two or more of blood, saline and other surgical fluids, is aspirated through outlet tube 132 in communication with tissue storage compartment 728 and into suction canister 130. Processing described above may be repeated for additional specimens 123 deposited with fluid 124 into respective tissue storage compartments 728. At 912, if no other tissue specimens 123 are to be severed and deposited into specimen tray 720, delivery fluid 724 and vacuum aspiration can be deactivated to terminate the biopsy procedure and proceed to imaging of tissue specimens 123 and fluid 124 and image processing.

Figure 11A:
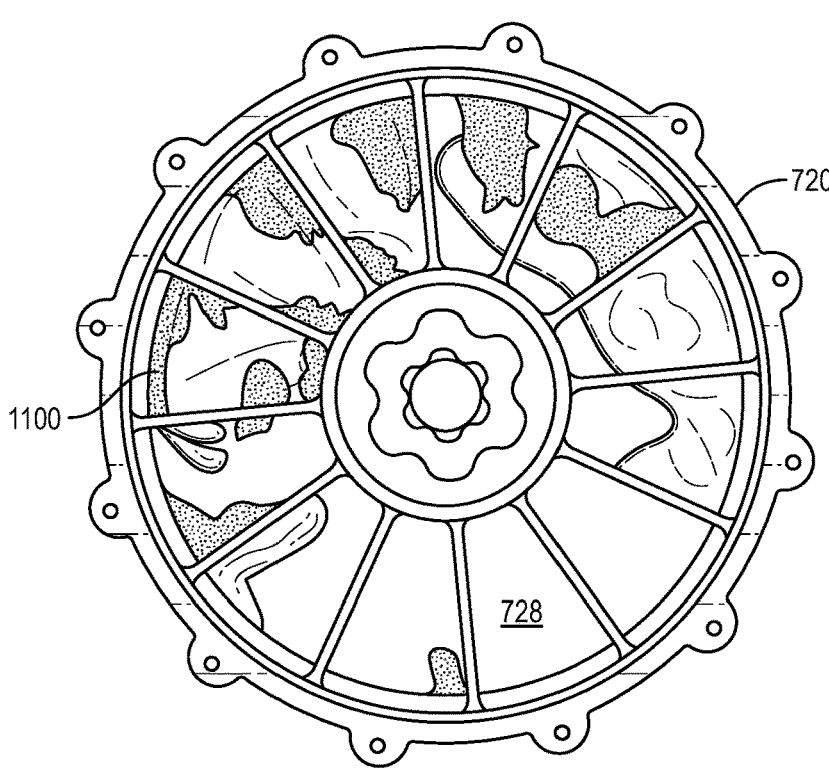
FIGS. 11A-B depict a specimen tray of a filter assembly of a tissue biopsy and handling system and how tissue specimens and fluids including different amounts of blood can be deposited into tissue storage compartments of the specimen tray.
Figure 11B:
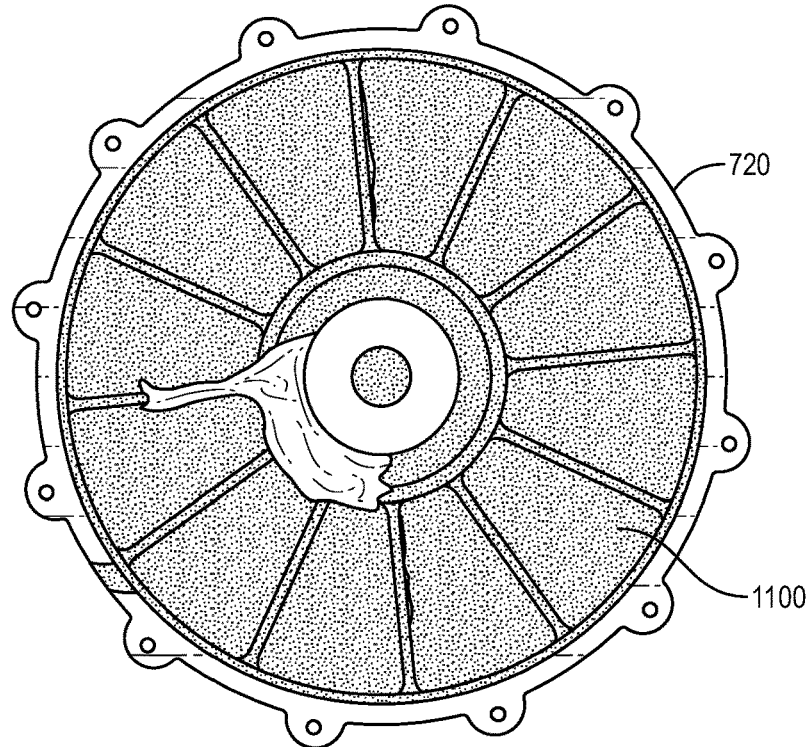

FIGS. 11A-B depict an exemplary specimen tray 720 after tissue specimens 123 have been excised, aspirated together with fluid 124 and deposited into respective storage compartments 728 of specimen tray 720. As depicted in FIG. 11A, tissue specimens 123 have been deposited in nine of the 12 tissue storage compartments 728 of together with fluids 124 including saline and blood 1100. Some tissue storage compartments 728 have more blood 1100 than others, and blood 1100 can significantly impair the visibility of tissue specimens 723 and completely cover tissue specimens 123. FIG. 11B illustrates an example in which a larger amount of blood 1100 was aspirated and deposited into respective tissue storage compartments 728, and so much blood has been deposited such that no tissue specimen 123 is visible. It will be understood that the amount of blood 1100 aspirated with tissue specimens 123 into tissue storage compartments 728 can vary, and that FIGS. 11A-B are provided to illustrate that different amounts of blood 1100 can be deposited, that fluids 124 including blood can partially or completely cover tissue specimens, and it will be understood that a fluid management device 760 can remove at least some of the blood 1100 and other fluids 124 to facilitate specimen imaging.

Referring again to FIG. 9, at 914, severed tissue specimen 123 that was deposited into tissue storage compartment 728 is positioned in the field of view of first or x-ray imaging system 141. This may involve rotating specimen tray 720 and/or moving x-ray imaging system 141 as necessary. At 916, x-ray imaging system 141 is activated to acquire an x-ray image 151 of severed tissue specimen 123 at least partially covered by one or more fluids 124. X-ray image 151 depicts external portions of tissue specimen 123 and internal portions of tissue specimen 123 that are not visible to the human eye. At 918, tissue specimen 123 is positioned in the field of view of optical camera imaging system 142. This may involve rotating specimen tray 720 and/or moving optical camera imaging system 142 as necessary. At 920, optical camera imaging system 141 is activated to acquire optical image 152 of tissue specimen 123 at least partially covered by one or more fluids 124. Optical image 152 depicts an outer surface of tissue specimen 123 and fluid 124 but not internal tissue specimen 123 portions that are not visible to the human eye.

FIG. 12A illustrates an example of a UI 1210 for "x-ray mode" during which x-ray image 152 is acquired and acquired x-ray images 151 of respective tissue specimens 123 may be presented through UI 1210. In the example shown in FIG. 12A, UI 1210 includes thumbnails 1212 of different x-ray images 151 of respective tissue specimens 123 that have been acquired, and a larger window 1212 displays a current x-ray image 151 of current tissue specimen 123 in tissue compartment 728 "C" per indicator or indicia 750 of specimen tray 720. FIG. 12B illustrates an example of a UI 1220 "camera mode" during which optical image 151 of specimens 123 (also depicted in UI 182 shown in FIG. 12C) is acquired and may be presented through UI 1220. FIG. 12B also illustrates an example in which optical camera imaging system 151 has a wider field of view such that cropping of optical images 152 may be required for eventual registration with x-ray image 151.

Figure 13A:
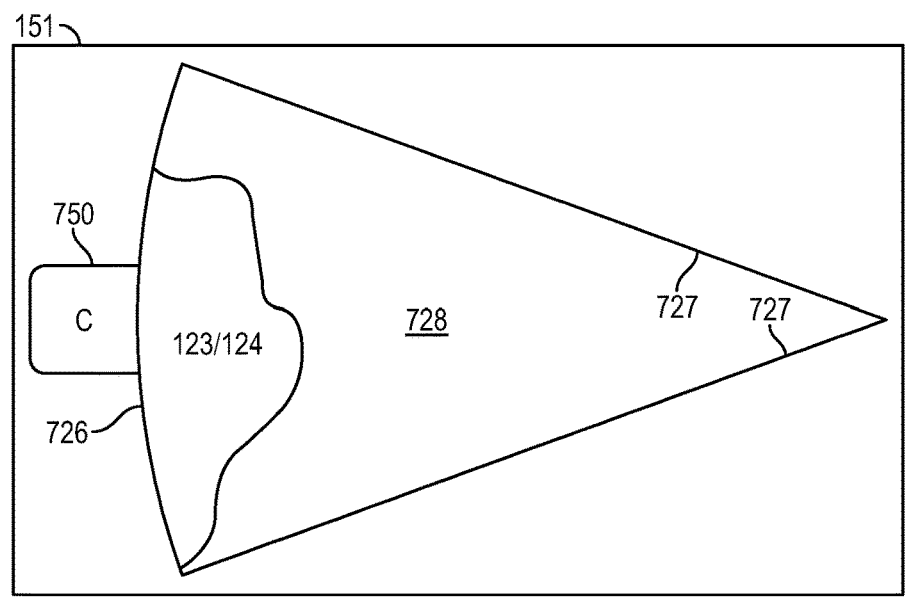
FIGS. 13A-B illustrate how different imaging systems of a tissue biopsy and handling system constructed according to one embodiment can have different fields of view and how resulting images can be processed to prepare for hybrid image generation according to embodiments.
Figure 13B:
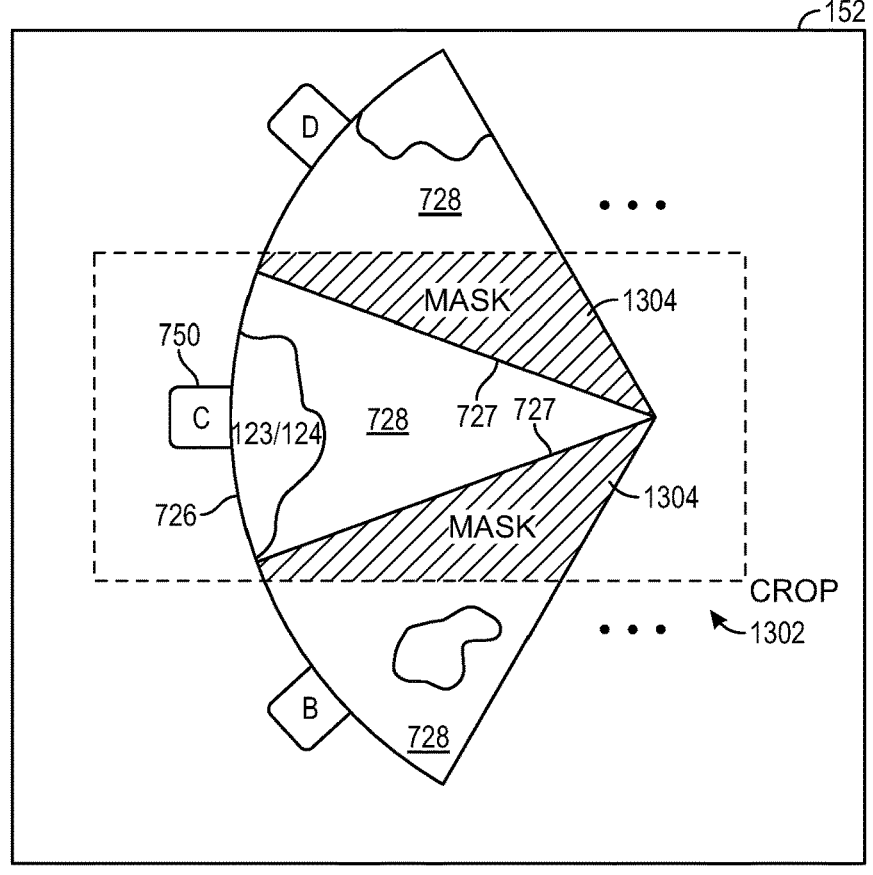

Continuing with reference to FIG. 9 and with further reference to FIGS. 13A-B, at 922, x-ray image 151 and optical image 152 are transmitted or exported by respective first and second imaging devices 141, 142 and received by image processor 160. At 924, image processor 160 executes x-ray and optical image registration 174 if needed. For example, as shown in FIGS. 13A-B, x-ray and optical images 151, 152 may depict different numbers of tissue compartments 728 or different portions of specimen tray 720 such that x-ray and optical images 151, 152 are not registered with each other due to optical camera imaging system 152 capturing a wider field of view than x-ray imaging system 151 or capturing optical image 152 at a different orientation or rotation such that processing results in x-ray and optical images 151, 152 corresponding to each other in terms of size, orientation and field of view. Image registration 174 may involve one or more of cropping one of the images, such as optical image 152, and making adjustments to one or more of zoom and orientation or rotation of specimen tray 720. The result of registration processing 174 is x-ray image 151 and optical image 152 depicting the same field of view of the same tissue specimen 123 and fluid 124 in the same tissue storage compartment 728 and x-ray image 151 and optical image 152 being sized and oriented to generally correspond to each other.

Image registration 174 may involve detection of one or crop attributes that are utilized to determine a common point of reference. This may involve one or more of shape recognition and tissue storage compartment indicia 750 recognition. For example, image processor 160 may analyze x-ray image 151 and optical image 152 for specimen tray 720 structures such as dividing walls 727 or sidewalls 726 having pre-defined shapes, locations or dimensions and tissue storage compartment indicia 750. It will be understood that various structures and landmarks may be utilized for these purposes and can vary with specimen tray 720 configurations such that the examples discussed above are provided as non-limiting examples of attributes that can be used for image registration 174.

For example, referring to FIG. 13A, x-ray image 151 may be an image of tissue specimen 123 and fluid 1234 in a single storage compartment 728 "C", whereas multiple tissue specimens 123 and fluid 124 in respective tissue storage compartments 728 B-D are depicted in optical image 152. Thus, as depicted in FIGS. 13A-B, optical image 152 may have a larger field of view than x-ray image 151 and may thus be cropped 1302 to include only a single tissue storage compartment 728 "C" similar to x-ray image 151. Optical image 152 can also be adjusted for dimensional and rotational or orientation correspondence such that the indicator "C" appears on the left side of x-ray and optical images 151, 152, and the pie or wedge shaped tissue storage compartments 728 are similarly arranged. As shown in FIG. 13B, image registration 174 may also involve a mask 1304 that is applied to eliminate any extraneous image portions, e.g., extraneous portions of optical image 152 that remained after initial cropping such as another other walls, base or filter materials that may remain. Supplemental masking 1304 may or may not be necessary depending on the configuration of the specimen tray 720 and fields of view of respective x-ray and optical camera imaging systems 141, 142. In the illustrated embodiment, dividing walls 727 partially define respective tissue storage compartments 728 such that tissue storage compartments 728 are adjacent to each other, whereas other specimen trays 720 may have other tissue storage compartment 728 configurations (e.g., square or rectangular shape) or be more spaced apart from each other such that supplemental masking 1304 may not be required for clean cropped images that are registered with each other. As an illustrative example, mask 1304 is shown to remove portions of two different storage compartments 728 from the upper right and bottom right corners of a cropped section of optical image 152. Similar processing may be applied to the x-ray image 151 as necessary. Thus, the result is two different images 151, 152 that correspond or substantially correspond to each other in preparation for generation of hybrid image 162.

Continuing with reference to FIG. 9, at 926, x-ray image 151 is provided as an input to first pre-processor 811, and at 928, optical image 152 is provided as an input to second pre-processor 812 at 926. Pre-processing refers to image processing before generation of hybrid image 162 or in preparation for generation of hybrid image 162. First pre-processor 811 and second pre-processor 812 execute different image processing methods on different images. Pre-processing may be applied to one or both or none of x-ray and optical images 151, 152, but for purposes of explanation, and not limitation, embodiments are described with reference to pre-processing 811, 812 of both x-ray and optical images 151, 152.

First pre-processor 811 may execute one or more image processing methods to prepare x-ray image 151 for fusion with optical image 152 or portions thereof or with graphically generated data based on optical image 152 portions by emphasizing and enhancing portions of x-ray image 151 depicting tissue specimen 123 and further differentiating tissue specimen 123 from surrounding or adjacent specimen tray 120 structures and fluid 124. For example, as described above with reference to FIG. 8, first pre-processor 811 may execute one or more filters 171 to reduce x-ray image 151 noise and filter out bright and dark image portions having brightness levels that exceed a maximum brightness level (to reduce bright spots) and/or that are less than a minimum brightness level (to reduce dark spots). Brightness filter 171 may use a pre-determined brightness criteria (one or both of a high brightness and low brightness criteria) to exclude or mask bright and dark portions of the x-ray image 151 such that remaining portions of the x-ray image 151 are more likely to depict tissue specimen 123 rather than specimen tray 720 and other elements that may appear as white or bright portions or black or dark portions or shadows in x-ray image 151. Thus, maximum and minimum brightness filters 171 may be used so that remaining x-ray image 151 data is more likely to depict tissue specimen 123 rather than other non-tissue elements while eliminating bright and dark portions, which may also reduce false positives and erroneously interpretations, e.g., an erroneous interpretation that a bright portion of x-ray image 151 depicts a calcification rather normal tissue. Filters 171 executed by first pre-processor 811 may also involve segmentation to further differentiate x-ray image 151 portions depicting the tissue specimen 123 from adjacent or surrounding structures of specimen tray 720. Segmentation may be performed using one or more of a pixel graph and a contrast filter to differentiate walls, tissue compartments and other specimen tray 720 structures, as well as magnetic components used to rotate specimen tray 720. First pre-processor 811 may also utilize specimen tray 710 templates or geometric data to distinguish tissue specimen 123 from adjacent or surrounding structures. For example, geometric data of dimension, center and location data of walls and surfaces of specimen tray 720 can be utilized to distinguish tissue specimens 123 that abut against or are adjacent to specimen tray 720 walls or surfaces. It will be understood that first pre-processor 811 may employ various image processing techniques to prepare the x-ray image 151 and enhance or emphasize tissue specimen 123 depicted in x-ray image 151.

Second pre-processor 812 executes on optical image 152 and uses different image processing methods than first pre-processor 811 for x-ray image 151. Second pre-processor 812 executes one or more image processing methods such tissue edge detection 172 on optical image 152, e.g., to identify boundaries of tissue specimen 123 that was deposited in tissue storage compartment 728. Edge detection may be used to identify tissue specimen 123 boundaries when at least part of tissue specimen 123 rests against a specimen tray 720 structure such as a dividing wall 727 or cylindrical sidewall 726 and to identify tissue specimen 123 boundaries when tissue specimen does not contact any specimen tray structure except for bottom member or surface 724 of specimen tray 720. According to one embodiment, edge detection 172 is performed for second or optical image 152 but not first or x-ray image 151. An edge, boundary or periphery of tissue specimen 123 can be determined, or at least determined in part, based one or more of a geometric structure, outline or layout of specimen tray 720 (e.g., walls, tissue storage compartments and identification indicia and associated relative locations thereof and dimensions such as wall thickness, height and length). Edge detection 172 results are used to generate optical image with improved tissue specimen 123 definition for improved eventual fusion with x-ray image 151.

Second pre-processor 812 may also process optical image 151 for interfering elements such as bubbles in the saline/blood fluid 124. This processing may involve an infrared filter that can be attached to a lens of optical camera imaging system 152 to further enhance and differentiate tissue specimen 123 and edges or boundaries thereof from interfering and surrounding fluids 124. Second pre-processor 812 may also utilize machine intelligence and training of a neural network for tissue edge or boundary detection and for boundary or edge detection in view of bubbles in saline/blood fluid 124, and for these purposes, second pre-processor 812 may communicate with machine learning components through a network such that certain image processing can be performed locally by image processor 160 and other image processing can be performed at a remote location, and the results of which are received through a network.

Second pre-processor 812 may also determine and execute initial opacity or transparency adjustments 173 for second or optical image 152 so that transparency of selected or determined portions of optical image 152 are modified. A digital optical image 152 is opaque, i.e., not transparent. Thus, second pre-processor 812 can execute initial transparency increases from 0% transparency or 100% opaque, and different transparency adjustments can be made to different portions of optical image 152.

For example, referring to FIG. 14, in one embodiment, second pre-processor 812 detects tissue specimen edge at 1402 as describe above (e.g., based on one or more of specimen tray 720 structures or indicia 750), and at 1404, second pre-processor 812 identifies pixels of second or optical image 152 corresponding to identified edge or boundary. Second pre-processor 812 adjusts optical image 152 by increasing transparency 173, or reducing opacity, of identified pixels at 1406. Transparency adjustment 173 may be executed without making any opacity or transparency adjustments to first or x-ray image 151. Transparency adjustment 173 may also be applied to other pixels of optical image 152 that are adjacent to identified pixels of optical image 152 or within a pre-determined distance from identified pixels of optical image 152. The result of transparency adjustment 173 is transformation of a determined portion of optical image 152 from opaque (a digital image generated by camera imaging device has 0% transparency) to semi-transparent. For example, transparency of determined portions of optical image 152 may be increased by 50%, but other transparency adjustments 173 may be utilized. In this manner, transparency adjustments 173 are applied to determined portions of optical image 152 depicting the "edge" or boundary of tissue specimen 123 to increase transparency while those adjusted optical image 152 portions are semi-transparent and remain visible, e.g., with 50% transparency so that they are not 100% transparent to disappear from view.

Continuing with reference to FIG. 14, at 1408, second pre-processor 812 also transforms other portions of second or optical image 152 from opaque (0% transparency) to substantially or entirely transparent. For example, transparency of determined portions of optical image 152 may be increased from 0% to 85-100%, but other transparency adjustments 173 may be utilized and these transparency values are merely illustrative examples. This may be done without making any transparency adjustments to x-ray image 151.

FIG. 15 generally illustrates how second pre-processor 812 can execute variable or differential transparency adjustments across optical image 152 such that certain portions of optical image 152 are semi-transparent 1502, and other portions of optical image 152 are more transparent, or even entirely transparent. Yet other portions of optical image 152, such as those portions beyond the edge or boundary of tissue specimen 123 (illustrated by section of bottom member or surface 724 of specimen tray 720 that does not have any portion of tissue specimen 123) may not have any transparency adjustment 173.

Second pre-processor 812 can implemented transparency adjustments 173 to modify second image 152 or generate image or graphical data in different ways. According to one embodiment, edge detection 172 is performed and optical image 152 transparency is adjusted so that portions of optical image 152 corresponding to detected edges or periphery are modified to be semi-transparent, whereas other optical image 152 portions that do not depict edge or periphery are modified to have an even higher transparency level to be substantially or entirely transparent. As another example, transparency adjustments 173 in optical image 152 may be made for corresponding sections of x-ray image 151, e.g., certain x-ray image 151 portions having brightness and/or contrast levels less than a desired or pre-determined contrast and/or brightness levels. In another embodiment, optical pre-processor 812 selects or extracts only certain portions of the optical image 152 corresponding to the detected edge or periphery of tissue specimen 123 depicted in optical image 152, and extracted or selected portions may form a "ring" type structure, and the "ring" type structure is modified to be semi-transparent. According to another embodiment, optical pre-processor 812 detects an edge or periphery of tissue specimen 123 and executes graphical processing to generate graphical representations or extraneous markers or identifiers for the detected edge or periphery. Thus, optical pre-processing 812 may involve an entire optical image 152 that has been modified with transparency modifications, certain portions of optical image 152 selected based on edge detection and that have been modified with transparency modifications, or generation of graphical representations based on respective portions of optical image 152 depicting an edge or periphery of tissue specimen 123. For ease of explanation, reference is made to optical image 152 or portions thereof, which is defined to include extracted or selected optical image 152 portions and graphical representations based on extracted or selected optical image 152 portions.

Thus, as generally illustrated in FIG. 15, transparency of optical image 152 or portions thereof in the form of an outer ring that highlights the edge or periphery of tissue specimen 123 in optical image 152 are modified to be semi-transparent 1502, whereas other interior portions of optical image 152 that were not determined to correspond to an edge or outer periphery are adjusted to have a higher transparency value and may be entirely transparent 1504. It will be understood that transparency adjustments 173 discussed herein, including 50% (semi-transparent), 85% (substantially transparent) and 100% (entirely transparent) are illustrative and non-limiting examples of transparency adjustments 173 that can be executed by optical pre-processor 812.

Referring to FIG. 16, second pre-processor 812 may also execute transparency adjustments 173, or determine which optical image 152 portions should have transparency increased, based on detected objects of interest such as calcifications in first or x-ray image 151. At 1602, second pre-processor 812 detects an edge or boundary of tissue specimen 123 depicted in second or optical image 152 as described above, and at 1604, second pre-processor detects, or executes an object detection system to detect, one or more objects of interest such as a lesion or calcification in tissue specimen 123 as depicted in first or x-ray image 151. At 1606, second pre-processor 812 identifies a first group of pixels of optical image 152 corresponding to identified edge/indicia attributes (as discussed above) with the constraint that the identified first group of pixels of optical image 152 do not correspond to portions of x-ray image 151 that depict detected calcification or other object of interest. At 1608, second pre-processor 812 increases transparency of the first group of identified pixels of optical image 152 (e.g., from 0% to 50% to be semi-transparent), and at 1610, transparency of other/unidentified pixels of optical image 152 that correspond to portions of x-ray image 151 that depict the detected object of interest, is increased to be substantially transparent (e.g., 85%) or 100% transparent. In other words, the transparency of portions of optical image 152 that correspond to a portion of x-ray image 151 depicting an object of interest can be increased to a level of substantially transparent or entirely transparent rather than remaining opaque or only being modified to a low transparency level.

Figure 17A:
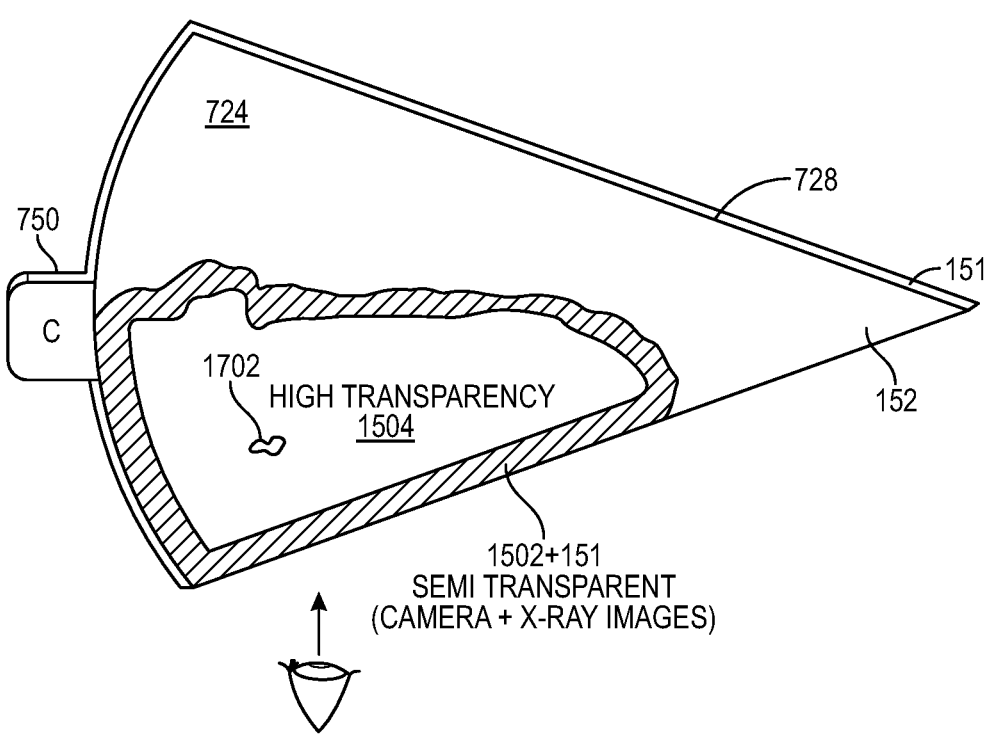
FIGS. 17A-B are provided to generally illustrate how a hybrid image may be generated and are respective top and cross-sectional views of a hybrid image showing how transparencies of selected portions of an optical image may be modified while transparencies of other optical image portions and an underlying x-ray image are not modified.
Figure 17B:
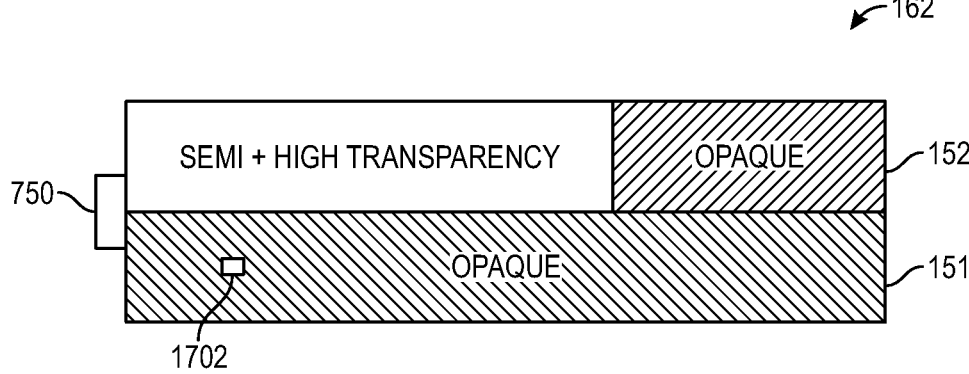

Referring again to FIGS. 3, 9 and 15, and with further reference to FIGS. 17A-B, outputs generated by first pre-processor 811 and second pre-processor 812, indicated as processed x-ray image 151p and processed optical image 152p are provided to image fusion processor 820. Image fusion processor 820 generates hybrid image 162 incorporating portions of x-ray and optical images 151, 152. Hybrid image 162 may be generated by x-ray image 151 being overlaid with optical image 152, overlaid with selected or extracted portions of optical image 152 (e.g., a peripheral ring), by integrating selected or extracted portions of optical image 152 into x-ray image 151 (e.g., by replacing portions of x-ray image 151 with selected or extracted peripheral ring of optical image 152), or by integrating generated graphical data or representations based on selected or extracted portions of optical image 152 into x-ray image 151 (e.g., by replacing portions of x-ray image 151 with generated graphical data or representations).

Selective transparency adjustments 173 to make certain portions of optical image 152 semi-transparent or generating a graphical representation to be semi-transparent 1502 and are applied over or integrated into x-ray image 151 contribute to depicting of edge or outer boundary of tissue specimen 123 more clearly than fluid 124 attenuated edge or outer boundaries depicted in the original x-ray image 141. Other portions 1504 of optical image 152 are modified to have high transparency so that the underlying portions of x-ray image 151 are more easily seen by user. In another embodiment, the x-ray image 151 is visible through the "hole" defined by or extending between extracted or selected semi-transparent optical image 152 or graphical representation. Thus, the resulting differential transparency across different portions 1502, 1504 of hybrid image 162 provides for an "overlaid" or "integrated" image mode in which portions of x-ray and optical images 151, 152 are presented to user so that outer edge or boundary of tissue specimen 123 is depicted by multiple images or multiple types of images rather than only one image and rather than by one image that is obscured by interfering fluid 124.

Embodiments thus compensate for corresponding portions of x-ray image 151 that may have been obscured by interfering fluid(s) 124 since corresponding semi-transparent portions 1502 of overlaid or integrated optical image 152 or portions thereof supplement x-ray image's 151 depiction of outer edge or boundary of tissue specimen 123. In addition to these improvements, other portions 1504 of optical image 152 are, or are adjusted, to be substantially or entirely transparent so that corresponding portions of x-ray image 151, including those portions of x-ray image 151 depicting a detected objects of interest 1702 such as a calcification or lesion, are visible to user without undue interference from optical image 152, optical image 152 portions or generated graphical representations based on same, and without interference from the original output of optical camera imaging system 152, which was 100% opaque so that a detected object of interest 1702 can also be observed. Depending on transparency adjustments executed, certain portions of optical image 152 may essentially disappear while other optical image 152 portions do not so that portions of x-ray image 151 can be as visible as in the absence of or with highly transparent optical image 152, while other portions of hybrid image 162 include optical image 152 portions that are less transparent and more visible.

FIGS. 17A-B generally illustrate how hybrid image 162 may be structured and how differential transparency adjustments can be made across hybrid image 162. It will be understood that transparency labels or descriptors such as opaque (0% transparency), low transparency (up to ~25%), semi-transparent (~25-~75%), substantially transparent or high transparency (greater than ~75%) and entirely transparent (100%) are provided for purposes of explanation and illustration, not limitation, and are provided to describe how embodiments may be implemented and how biopsy specimen imaging can be customized for tissue specimens of different shapes and sizes and customized for different tissue specimen positions within a specimen tray 720 after being excised and deposited therein.

While FIG. 17B generally depicts a cross-sectional view of hybrid image 162 generated by optical image 152 (or 152*p*) being applied over x-ray image 151, it will be understood that hybrid image 162 may be generated and structured in different ways and that embodiments may utilized different methods of image fusion. Hybrid image 162 may be generated by only selected or extracted portions of optical image 152 (e.g., a semi-transparent peripheral ring based on edge detection) being applied over x-ray image 151. Hybrid image 162 may also be generated by semi-transparent selected or extracted portions of optical image 151 being integrated into x-ray image 152 rather than being applied over x-ray image 152. For this purpose, pixels of x-ray image 151 may be replaced by the semi-transparent selected or extracted portions of optical image 151. As another example, hybrid image 162 may be generated by semi-transparent generated graphical representation based on detected edge or periphery of tissue specimen in optical image 152 being applied over x-ray image 152. Hybrid image may also be generated by integrating semi-transparent generated graphical representation into x-ray image 151 rather than being applied over x-ray image 152, e.g., by replacing x-ray image 151 pixels with the generated graphical representation.

Thus, embodiments are able to generate hybrid image 162 that is not only customized to tissue specimens 123 at least partially surrounded or covered by fluid 124 but also customized to a structural configuration of biopsy system 100 components such as specimen trays 720 and walls thereof, while, at the same time, enhancing tissue specimen 123 edges or boundaries that may otherwise be obscured in an x-ray image 151 due to interfering fluid 124 while also executing transparency modifications so that objects of interest 1702 depicted in x-ray image 151 can be viewed through optical image 152. Embodiments also address surgical and bodily fluids such as blood 1100 that have attenuation attributes similar to the tissue specimen 123 being imaged and thus may interfere with specimen imaging. Thus, rather than making generic transparency adjustments, embodiments can intelligently determine which optical image 152 portions should have transparency adjustments, how transparency should be adjusted in view of the particular imaging environment, and how certain portions of an optical image 152 should be modified and applied over or integrated into x-ray image 151.

Referring again to FIG. 9 and with further reference to FIG. 18, at 932, generated hybrid image 162 is presented to the user through interactive UI 182 via display 180 of biopsy system 100. User may interact with UI 182 through an input device such as a keyboard, mouse, touchscreen and the like. UI 182 allows the user to make various other adjustments to hybrid image 162 or to change how hybrid image 162 or x-ray and optical images 151, 152 thereof are presented.

For example, UI 182 can be structured to allow user to further adjust 1204 transparency levels for different portions of second or optical image 152. Transparency adjustments may be executed in response to a user positioning a mouse pointer over a certain optical image 152 portion (e.g., semi-transparent ring or boundary portion 1502 of optical image 152 as shown in FIG. 15), and then actuating a scroll wheel of mouse to increase or decrease the transparency of that portion 1502 while transparency of other portions of optical image 152 and x-ray image 151 remain unchanged. As another example, mouse pointer may be positioned over a certain optical image 152 portion (e.g., high transparency portion 1504 as shown in FIG. 15), and then actuating a scroll wheel of mouse to increase or decrease the transparency of that portion 1504 while transparency of other portions of optical image 152 and x-ray image 151 remain unchanged. This may be useful to increase transparency when attempting to analyze object of interest 1702 in underlying x-ray image 151.

UI 182 may also provide for a global transparency adjustment, which may be based on current respective transparency levels so that transparency differential is maintained, or based on a common transparency level so that transparency adjustments are constant across optical image 152. For example, if the transparency level of "edge" portions 1502 of optical image 152 is 40% and the transparency level of "internal" portions 1504 of optical image 152 is 90%, then applying a global transparency increase of 10% would result in the "edge" portion 1502 transparency being increased to 50% (40+10) and the "internal" portion 1504 transparency being adjusted to 100% (90+10). In other methods, the transparency of edge and inner portions 1502, 1504 may be adjusted but to the same transparency value. UI 182 may also a user to deactivate differential transparency display and adjustments to allow for more user control.

UI 182 may also allow for different views of hybrid image 162 or image components thereof. For example, UI 182 may include a "toggle" button 1210 that can be selected by the operator so that one view is the "hybrid" view in which x-ray image 151 is overlaid with optical image 152 or portions of optical image 152 are integrated into x-ray image, and a second view presents the x-ray image 151 and optical image 152 independently and not in hybrid mode.

Other UI 182 elements 1212 may allow a user to manually draw on second or optical image 152 to draw an image portion for which transparency is to be adjusted, e.g., similar to drawing tools available from Zillow Group and used by home shoppers that allow for use a mouse to draw a circle around a neighborhood of interest With continuing reference to FIG. 9, at 936, image processor 160 receives the user input via UI 812 and modifies hybrid image 162 or other image or transparency adjustments in response to user input, and at 938, the modified hybrid or other image or transparency modification is presented to user through UI 812.

Thus, as described above, embodiments provide for improved tissue specimen imaging, analysis of same and user interactions with same by not only utilizing multiple imaging modalities, but by selectively modifying image transparencies for certain image portions, and for certain images. These intelligent transparency adjustments allow biopsy system 100 to compensate for fluid 124 interference with tissue specimen 123 imaging and inadvertent shadows created in images that may block tissue or objects of interest, while enhancing depiction and display of tissue specimen 123 edges or boundaries while doing so without obscuring detected objects of interest such as calcifications and lesions depicted in x-ray images. Embodiments achieve these significant imaging improvements, but do so in real time during a biopsy procedure such that improved imaging results can be presented to the operator who can make a more accurate and efficient analysis and determine, for example, whether additional tissue specimens should be acquired. Embodiments may be utilized to improve imaging in the presence of one or multiple fluids including one or more of saline and blood, and are particularly useful when imaging tissue specimens coated in blood and fluids that have attenuation attributes that are similar to those of the tissue specimen or objects of interest in the tissue specimen being imaged. Embodiments are also adaptable and configurable for use in various biopsy systems and specimen tray configurations since image processing of embodiments can account for different system component structures and tissue specimens of different shapes and sizes deposited in different ways in such systems. Thus, embodiments are adaptable to various system components configurations and tissue specimens and biopsy procedures, one example of which is a breast biopsy procedure.

Although particular embodiments of the disclosed inventions have been shown and described, it is to be understood that the above description is provided for purposes of explanation and illustration only. Thus, various changes and modifications may be made without departing from the scope of the disclosed inventions. For example, not all of the components depicted and described in the disclosed embodiments are necessary, and various additional embodiments of the disclosed inventions may include any suitable combinations of the described components, and the general shapes and relative sizes of the components may be modified. While the systems and methods have been described with reference to imaging of breast tissue samples acquired during a biopsy procedure, embodiments can also be configured and utilized with any types of tissue specimens. Accordingly, embodiments are intended to exemplify alternatives, modifications, and equivalents that may fall within the scope of the claims.

The invention claimed is:

1. A specimen imaging apparatus, comprising:
a tissue holder assembly defining a tissue storage compartment for a severed tissue specimen;
an x-ray imaging system arranged relative to the tissue storage compartment to acquire an x-ray image of the severed tissue specimen in the tissue storage compartment;
an optical camera imaging system arranged relative to the tissue storage compartment to acquire an optical image of the severed tissue specimen in the tissue storage compartment, wherein the optical image includes an edge of the severed tissue specimen;
an image processor in communication with the x-ray imaging system and the optical camera imaging system, the image processor being configured to receive the x-ray image and the optical image, and generate a hybrid image based at least in part upon the x-ray image and the optical image, and the edge of the severed tissue specimen depicted in the optical image, and wherein the image processor being further configured to detect the edge of the severed tissue specimen depicted in the optical image based on a pre-determined minimum contrast difference between a portion of the severed tissue specimen and a portion of the tissue storage compartment depicted in the optical image; and
a display in communication with the image processor, the hybrid image being presented to a user of the specimen imaging apparatus through the display.

2. The specimen imaging apparatus of claim 1, wherein the severed tissue specimen comprises a severed breast tissue specimen, wherein a calcification in the severed breast tissue specimen is depicted in the x-ray image but not the optical image.

3. The specimen imaging apparatus of claim 1, wherein the tissue holder assembly comprises a tray defining the tissue storage compartment, wherein the tray is rotatable within the tissue holder assembly, the specimen imaging apparatus being configured to rotate the tray from a first position in which the severed tissue specimen has been deposited into the tissue storage compartment to a second position, wherein the x-ray and optical camera imaging systems are configured to acquire the respective x-ray and optical images of the severed tissue specimen while the tray is in the second position.

4. The specimen imaging apparatus of claim 1, the image processor being configured to generate the hybrid image based on the x-ray image being overlaid with the optical image and determined portions of the optical image being semi-transparent so that underlying portions of the x-ray image are at least partially visible through the determined portions of the optical image, wherein a first transparency of a first portion of the optical image depicting the edge of the severed tissue specimen is lower than a second transparency of a second portion of the optical image depicting an interior or middle portion of the severed tissue specimen.

5. The specimen imaging apparatus of claim 1, wherein the edge of the severed tissue specimen depicted in the optical image is detected with reference to a wall of the tissue storage compartment.

6. The specimen imaging apparatus of claim 1, the image processor comprising a first pre-processor and a second pre-processor configured to execute respective pre-processing on the respective x-ray and optical images in preparation for generation of the hybrid image.

7. The specimen imaging apparatus of claim 6, the first pre-processor being configured to execute a first brightness filter on the x-ray image, the first brightness filter being configured to identify portions of the x-ray image having a brightness level greater than a pre-determined maximum brightness threshold, and mask or reduce the brightness of the identified portions of the x-ray image.

8. The specimen imaging apparatus of claim 7, wherein the first brightness filter is configured to mask or reduce brightness of at least one of a portion of the severed tissue specimen depicted in the x-ray image and a structural component of the tissue storage compartment imaged during acquisition of the x-ray image.

9. The specimen imaging apparatus of claim 7, the first pre-processor being further configured to execute a second brightness filter on the x-ray image, the second brightness filter being configured to identify portions of the x-ray image having a brightness level less than a pre-determined minimum brightness threshold, and mask or increase the brightness of the identified portions of the x-ray image having a brightness level less than the pre-determined minimum brightness threshold.

10. The specimen imaging apparatus of claim 9, wherein identified portions of the x-ray image having a brightness level less than the pre-determined minimum brightness threshold depict a bottom surface of the tissue storage compartment onto which the severed tissue specimen is deposited.

11. The specimen imaging apparatus of claim 6, the first pre-processor being configured to execute a noise reduction filter on the x-ray image.

12. The specimen imaging apparatus of claim 6, the second pre-processor being configured to increase a transparency of a portion of the optical image from a first transparency to a second transparency that is greater than the first transparency, wherein the second transparency results in the portion of the optical image being semi-transparent so that the portion of the optical image is visible to the user and underlying portions of the x-ray image are at least partially visible to the user through the semi-transparent portion of the optical image.

13. The specimen imaging apparatus of claim 12, the second pre-processor being configured to increase respective transparencies of respective portions of the optical image such that the optical image comprises different transparency levels.

14. The specimen imaging apparatus of claim 6, the second pre-processor being configured to generate semi-transparent graphical representation of the severed tissue specimen based at least in part upon the edge of the severed tissue specimen, the hybrid image comprising the generated semi-transparent graphical representation.

15. The specimen imaging apparatus of claim 14, wherein the image processor is configured to integrate the generated semi-transparent graphical representation into the x-ray image by replacing pixel data of the x-ray image with pixel data of the generated semi-transparent graphical representation.

16. The specimen imaging apparatus of claim 1, the specimen imaging apparatus being further configured to receive user input through a user interface of the display and modify the user interface in response to the user input by modifying the hybrid image so that the x-ray image is no longer overlaid with the optical image, and the x-ray image and the optical image are separately presented to the user through the user interface.

17. The specimen imaging apparatus of claim 1, wherein the tissue storage compartment is a first tissue storage compartment and the severed tissue specimen is a first severed tissue specimen, the x-ray image includes the first severed tissue specimen deposited in the first tissue storage compartment, and the optical image includes a plurality of severed tissue specimens including the first severed tissue specimen deposited into a plurality of respective tissue storage compartments including the first tissue storge component, the image processor being configured to:

identify a portion of the optical image that corresponds to the first severed tissue specimen deposited in the first tissue storage compartment depicted in the x-ray image;

crop the identified portion of the optical image; and register the x-ray image and the cropped portion of the optical image with reference to a component of the tissue storage compartment, wherein the hybrid image is generated based at least in part upon the registered x-ray and the cropped portion of the optical image.

18. The specimen imaging apparatus of claim 17, wherein the component of the tissue storage compartment is at least one of a wall, a tray defining the tissue storage compartment, an identifier associated with the tissue storage compartment, and a rotational center of the tissue storage compartment.

19. The specimen imaging apparatus of claim 1, wherein the image processor is further configured to detect a lesion, a calcification, or an object of interest within the x-ray image that is not visible within the optical image.

20. A specimen imaging apparatus, comprising:

a tissue holder assembly defining a tissue storage compartment for a severed tissue specimen;

an x-ray imaging system arranged relative to the tissue storage compartment to acquire an x-ray image of the severed tissue specimen in the tissue storage compartment;

an optical camera imaging system arranged relative to the tissue storage compartment to acquire an optical image of the severed tissue specimen in the tissue storage compartment, wherein the optical image includes an edge of the severed tissue specimen;

an image processor in communication with the x-ray imaging system and the optical camera imaging system, the image processor being configured to receive the x-ray image and the optical image, and generate a hybrid image based at least in part upon the x-ray image and the optical image, and the edge of the severed tissue specimen depicted in the optical image, wherein the image processor being further configured to generate the hybrid image based on the x-ray image being overlaid with the optical image and determined portions of the optical image being semi-transparent so that underlying portions of the x-ray image are at least partially visible through the determined portions of the optical image, wherein a first transparency of a first portion of the optical image depicting the edge of the severed tissue specimen is greater than a second transparency of a second portion of the optical image depicting an interior or middle portion of the severed tissue specimen; and a display in communication with the image processor, the hybrid image being presented to a user of the specimen imaging apparatus through the display.

21. A specimen imaging apparatus, comprising:

a tissue holder assembly defining a tissue storage compartment for a severed tissue specimen, wherein the tissue storage compartment is a first tissue storage compartment and the severed tissue specimen is a first severed tissue specimen;

an x-ray imaging system arranged relative to the tissue storage compartment to acquire an x-ray image of the severed tissue specimen in the tissue storage compartment, the x-ray image includes the first severed tissue specimen deposited in the first tissue storage compartment;

an optical camera imaging system arranged relative to the tissue storage compartment to acquire an optical image of the severed tissue specimen in the tissue storage compartment, wherein the optical image includes an edge of the severed tissue specimen, and the optical image includes a plurality of severed tissue specimens including the first severed tissue specimen deposited into a plurality of respective tissue storage compartments including the first tissue storge component;

an image processor in communication with the x-ray imaging system and the optical camera imaging system, the image processor being configured to receive the x-ray image and the optical image, and generate a hybrid image based at least in part upon the x-ray image and the optical image, and the edge of the severed tissue specimen depicted in the optical image, and wherein the image processor being further configured to:

identify a portion of the optical image that corresponds to the first severed tissue specimen deposited in the first tissue storage compartment depicted in the x-ray image;

crop the identified portion of the optical image; and register the x-ray image and the cropped portion of the optical image with reference to a component of the tissue storage compartment, wherein the hybrid image is generated based at least in part upon the registered x-ray and the cropped portion of the optical image; and a display in communication with the image processor, the hybrid image being presented to a user of the specimen imaging apparatus through the display.

* * * * *